US011535599B2

(12) United States Patent
Tanaka et al.

(10) Patent No.: US 11,535,599 B2
(45) Date of Patent: Dec. 27, 2022

(54) BENZISOXAZOLE DERIVATIVE

(71) Applicant: Sumitomo Pharma Co., Ltd., Osaka (JP)

(72) Inventors: Tomoyuki Tanaka, Osaka (JP); Yoshiaki Isobe, Osaka (JP); Hiroyuki Kitano, Osaka (JP); Hiroaki Tanaka, Osaka (JP); Shun Narai, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 17/701,539

(22) Filed: Mar. 22, 2022

(65) Prior Publication Data

US 2022/0289694 A1    Sep. 15, 2022

Related U.S. Application Data

(63) Continuation of application No. 17/623,527, filed as application No. PCT/JP2021/025403 on Jul. 6, 2021.

(30) Foreign Application Priority Data

Jul. 7, 2020 (JP) ................................ 2020-117236

(51) Int. Cl.
  *C07D 261/20* (2006.01)
  *A61P 25/16* (2006.01)
  *A61P 25/14* (2006.01)
  *A61P 25/02* (2006.01)

(52) U.S. Cl.
  CPC ............ *C07D 261/20* (2013.01); *A61P 25/02* (2018.01); *A61P 25/14* (2018.01); *A61P 25/16* (2018.01); *C07B 2200/13* (2013.01)

(58) Field of Classification Search
  CPC ........ C07D 261/20; A61P 25/02; A61P 25/14; A61P 25/16; C07B 2200/13
  See application file for complete search history.

(56) References Cited

U.S. PATENT DOCUMENTS

| 4,172,896 | A | 10/1979 | Uno |
| 6,342,515 | B1 | 1/2002 | Masuda et al. |
| 2018/0271838 | A1 | 9/2018 | Ohno |

FOREIGN PATENT DOCUMENTS

| JP | 53-77057 | 7/1978 |
| JP | 3-7226 | 1/1991 |
| WO | WO 4172596 A | 6/1994 |
| WO | WO 99/33465 | 8/1999 |

OTHER PUBLICATIONS

Kenji Shirakura et al., Journal of Japanese Society of Hospital Pharmacists (Jun. 1, 2009), vol. 45, No. 6, pp. 830-831 with the English Translation.

PCTISA210 International Search Report.
Perchalski, R.J. et al, "Biotransformation and excretion: metabolite identification: other mass spectrometric methods", Journal of Clinical Pharmacology, 1966, vol. 26, No. 6, pp. 435-442. English Translation.
Database Registry, 2014, RN 1596612-84-8. Retrieved from STN international [online]; retrieved on Jul. 26, 2021.
Suzuki, S. et al., "Zonisamide blocks T-type calcium channel in cultured neurons of rat cerebral cortex", Epilepsy Research, 1992. vol. 12, No. 1pp. 21-27. English Translation.
William A. Catterall et al., "International Union of Pharmacology. XLVII. Nomenclature and Structure-Function Relationships of Voltage-Gated Sodium Channels", Pharmacological Reviews 57(4) 397-409 (2005).
Joseph G.McGivern et al., "Targeting N-type and T-type calcium channels for the treatment of pain", Drug Discovery Today 11(5/6) 245-253 (2006).
Evanthia Nanou et al., "Calcium Channels, Synaptic Plasticity, and Neuropsychiatric Disease", Neuron 98(3) 466-481 (2018).
Q. Ashton Acton, PhD. (Eds.), Ion Channels—Advances in Research and Application. 2013 Edition ScholarlyEditionsTM, Atlanta, Georgia, pp. 1-103.
Ryo Fukumoto et al., "Two Epilepsy Patients Who Developed Renal/Ureteral Stones While Taking Topiramate (Topina®)", Acta Urologica Japonica (2011), 57(3): 125-128. W/English Translation.
Hidenori Maruyama et al., Influences of switchng from dopamine agonist to zonisamide on psychotic and motor symptoms of PD patients with hallucination and delusion,Parkinson's Disease and Movement Disorder Congress, Program and Proceedings vol. 14, p. 96(Feb. 2021). W/English Translation.
Shunsuke Tani et al., "The situation of real clinical prescription for patients with Parkinson's disease exhibiting wearing-off, and the examination of safety and effectivity of 50 mg/day of zonisamide" Neurology(ISSN:2434-3285) vol. 91, No. 3 p. 378-389(Sep. 2019). W/English Translation.

(Continued)

*Primary Examiner* — Robert H Havlin
(74) *Attorney, Agent, or Firm* — Oblon, McClelland, Maier & Neustadt, L.L.P.

(57) ABSTRACT

The present invention relates to a medicament for treating various nervous system diseases or psychiatric diseases, comprising a compound of formula (1) or a pharmaceutically acceptable salt thereof as an active ingredient, wherein $R^1$ is hydrogen, etc., $R^2$ is halogen, etc., $R^3$, $R^4$, $R^5$, and $R^6$ are hydrogen, etc.

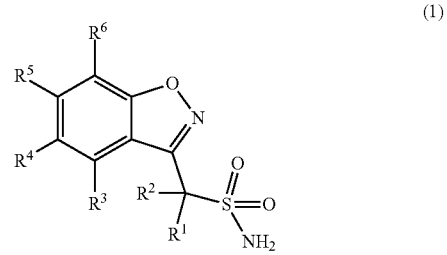

(1)

28 Claims, 15 Drawing Sheets

(56) References Cited

OTHER PUBLICATIONS

Masaaki Tagawa. "Zonisamide as a repositioned drug: Fruit of serendipity", Journal of Pharmacological Sciences(ISSN:1347-8613) vol. 133, 3Suppl. p. S80(Mar. 2017).

Chiaki Migihashi et al., "Interim report of research for achievement of specific use of zonisamide for Parkinson's disease patients (50 mg long-term)", Parkinson's Disease and Movement Disorder Congress, Program and Proceedings vol. 11, p. 90(Oct. 2017).

Chiaki Migihashi et al., Study of safety and efficacy of 50 mg of zonisamide for Parkinson's disease patients with expression of wearing-off phenomenon—Interim report of specific use achievement research regarding long-term use—Journal of New Remedies & Clinics(ISSN:0559-8672), vol. 66, No. 12, p. 1493-1509(Dec. 2017) W/English Translation.

Nami Kawaguchi et al., "Zonisamide (Trerief® tablet 25 mg) specific use achievement research targeted at Parkinson's disease patients—Research related to long-term use", Pharma Medica(ISSN:0289-5803), vol. 32, No. 7, p. 89-99(Jul. 2014). W/English Translation.

Yutaka Murahashi et al.,"Regarding Parkinson's disease therapeutic drug Trerief® (zonisamide)", separate volume, Bio Clinica: vol. 3, No. 1 p. 150-155(May 2014). W/English Translation.

Kenji Shirakura, "Parkinson's disease therapeutic agent Trerief—Additional dose against wearing-off phenomenon—", Medical Science Digest(ISSN:1347-4340), vol. 40(1) p. 42-46(Jan. 2014).—With English Translation.

Tomoaki Matsumoto et al., "Concerning New Parkinson's Therapeutic Agent "Trerief®"", Bio Clinica(ISSN:0919-8237), vol. 26, No. 8, p. 716-720(Aug. 2011).—with English Translation.

Tomoaki Matsumoto et al., "Anti-Parkinson Effects of Trerief®", Sumitomo Kagaku(ISSN:0387-1312) vol. 2010-II p. 62-66(Nov. 2010)—with English Translation.

Kenji Shirakura. "New anti-Parkinson's disease drug Trerief® (zonisamide)", Medical Science Digest(ISSN:1347-4340), vol. 36(14) p. 1203-1206(Dec. 2016).—with English Translation.

Kenji Shirakura et al., "New Drug Prospects 2010 Part II Featured new drug Levodopa incorporation-type Parkinson's disease therapeutic drug General name: Zonisamide Trerief® tablet", Medicine and drug journal(ISSN:0287-4741), vol. 46 special number, p. 269-273(Jan. 2010).

Kenji Shirakura, "World Medicine from Japan (34) Levodopa incorporation-type Parkinson's disease therapeutic drug Trerief® development story", IRYO(ISSN:0021-1699)vol. 63. No. 10, p. 680-682(Oct. 2009).—With English Translation.

Kenji Shirakura, "Levodopa incorporation-type Parkinson's disease therapy drug Zonisamide tablet (Trerief® tablet)", Journal of the Chiba Pharmaceutical Association, vol. 55, No. 10 p. 960-963(Oct. 2009).

Kenji Shirakura et al., "[Introduction of new medicine] Levodopa incorporation-type Parkinson's disease therapeutic drug Zonisamide (Trerief® tablet)", Journal of Japanese Society of Hospital Pharmacists (ISSN:1341-8815), vol. 45, No. 6, p. 830-831(Jun. 2009).

Saori Tsujii, "Protective effect of zonisamide on endoplasmic reticulum stress-induced nerve cell death", The regional meeting of the Japanese Pharmacological Society (Nippon Yakurigaku Zasshi) 142(5): 10-10, 2013. w/ English Translation.

Yoshio Tsuboi et al., "Zonisamide improves wearing-off without worsening dyskinesia of Parkinson's disease patients: Post hoc analysis of clinical trial data", Parkinson's Disease and Movement Disorder Congress, Program and Proceedings (2021) vol. 15, pp. 102.—With English Translation.

Takashi Abe et al."Effects of switching from dopamine agonists to zonisamide on psychiatric and motor symptoms in patients with Parkinson's disease,",Clinical Neurology(Web) (2021) vol. 61, No. 7, pp. 449-455(J-Stage.

Hidenori Maruyama et al., "Zonisamide improves wearing off without worsening dyskinesia of PD: post hoc analysis of clinical trial data", Annual Meetings of the Japanese Society of Neurology, Program and Proceedings (2021) vol. 62, pp. 414.—With Ergjish Translation.

Takashi Abe et al., "Influences of shifting from dopamine agonist to zonisamide on mental and motor conditions of PD patients", Annual Meetings of the Japanese Society of Neurology, Program and Proceedings (2020), vol. 61, pp. 486.—with English Translation.

Hirotaka Iwaki et al., "Companson of zonisamide with non-levodopa, anti-Parkinson's disease drugs in the incidence of Parkinson's disease-relevant symptoms", Journal of the Neurological Sciences(2019), vol. 402, pp. 145-152.

Chiaki Migihashi et al., "Evaluation of Safety and Efficacy of Zonisamide 50 mg in Parkinson's Disease Patients with Wearing-off Phenomenon—Interim Reports of the Long Term Special Drug Use Result Survey". Journal of New Remedies & Clinics (Dec. 10, 2017), vol. 66, No. 12, pp. 1493-1509.—With English Translation.

Miho Murata et al., "Consolidated Analysis of Placebo-Controlled Double-Blind Study of Zonisamide in Parkinson's Patients", Annual Meetings of the Japanese Society of Neurology, Program and Proceedings, (2014) vol. 55, pp. 515. With English Translation.

Miho Murata et al., "Effect of Zonisamide in Shortening the Off Period: A Domestic Multicenter Joint Double-Blind Study", Parkinson's Disease and Movement Disorder Congress, Program and Proceedings, (2013) vol. 7, pp. 75.W/ English Translation.

Masuda Y. et al., "Evidence against a Significant Implication of Carbonic Anhydrase Inhibitory Activity of Zonisamide in its Anticonvulsive Effects", Arzneimittel-Forschung, (Mar. 1994) vol. 44, No. 3, pp. 267-269.

Masuda Y. et al., "Inhibitory Effect of Zonisamide on Human Carbonic Anhydrase in vitro", Arzneimittel-Forschung, (Apr. 1993) vol. 43, No. 4, pp. 416-417.

Tanaka. Tomoyuki, et al, "N-alkyl-[1,1'-biphenyl]-2-sulfonarnide derivatives as novel broad spectrum anti-epileptic drugs with efficacy equivalent to that of sodium valproate", Bioorganic and Medicinal Chemistry Letters, (2017) vol. 27, No. 17, pp. 4118-4121, Refs: 11 ISSN: 0960-894X: E-ISSN: 1464-3405 CODEN: BMCLE8.

Matsumoto K. et al., "Binding of sulfonamides to erythrocytes and their components", Chemical and Phamiaceuticai Bulletin, (Jul. 1989) vol. 37, No. 7, pp. 1913-1915.

Tsuboi, Yoshio et al.,"Zonisamide improves wearing off in Parkinson's disease without exacerbating dyskinesia: Post hoc analysis of phase 2 and phase 3 clinical trials". Journal of the Neurological Sciences, (Nov. 15, 2021) vol. 430. am. 120026. Refs. 35 ISSN: 0022-510X: E-ISSN: 1878-5883 CODEN: JNSCAG.

Odawara, Toshinari, et al., "Long-Term Efficacy and Safety of Zonisamide for Treatment of Parkinsonism in Patients With Dementia With Lewy Bodies: An Open-Label Extension of a Phase three Randomized Controlled Trial.", American Journal of Geriatric Psychiatry, (2021) . Refs: 32ISSN: 1064-7481; E-ISSN: 1545-7214 CODEN: AJGPE8.

Hasegawa, Kazuko, et al., "Efficacy and Safety of Zonisamide in Dementia with Lewy Bodies Patients with Parkinsonism: A Post Hoc Analysis of Two Randomized, Double-Blind, Placebo-Controlled Trials", Journal of Alzheimer's Disease, (2021) vol. 79, No. 2, pp. 627-637. Refs: 36 ISSN: 1387-2877; E-ISSN: 1875-8908 CODEN: JADIF9.

Tanaka, Tomoyuki et al., "Identification of 2-(2'-fluoro-[1.1'-biphenyl]-2-yl)acetamide as a Sodium Valproate-like broad spectrum anti-epileptic drug candidate", Bioorganic and Medicinal Chemistry Letters, (Jan. 15, 2019) vol. 29, No. 2, pp. 138-142. Refs: 20 ISSN: 0960-894X; E-ISSN: 1464-3405 CODEN: BMCLE8.

Takai, Kentaro et al., "Long-term Efficacy of Zonisamide on Parkinsonism in Dementia with Lewy Bodies: A Post-hoc Analysis of Phase 3 Trial",Neurology, (Apr. 9, 2019) vol. 92. No. 15, Suppl. S, pp. P4.1-012. Meeting Info.: 71st Annual Meeting of the American-Academy-of-Neurology (AAN). Philadelphia, PA, USA. May 4-10, 2019. Amer Acad Neurol.

Nishimaki, Takuya et al., "Long-term efficacy of zonisamide on parkinsonism in dementia with Lewy bodies: A post-hoc analysis of phase III trial", Journal of Parkinson's Disease, (2019) vol. 9, No.

(56) References Cited

OTHER PUBLICATIONS 1, pp. 158. Abstract No. P23.13.Meeting Info. 5th World Parkinson Congress, WPC 2019, Kyoto, Japan, Jun. 4, 2019-Jun. 7, 2019 ISSN: 1877-718X.

Toya, Shunji et al., "Long-term efficacy for parkinsonism and safety of zonisamide in patients with dementia with Lewy bodies: A phase III trial",Journal of Parkinson's Disease, (2019) vol. 9, No. 1, pp. 162. Abstract No. P23.22.Meeting Info: 5th World Parkinson Congress, WPC 2019, Kyoto, Japan. Jun. 4, 2019-Jun. 7, 2019 ISSN: 1877-718X.

Toya, Shunji et al., "Long-Term Efficacy for Parkinsonism and Safety of Zonisamide in Patients with Dementia with Lewy Bodies: A Phase III Trial", Neurology, (Apr. 9, 2019) vol. 92, No. 15, Suppl. S, pp. P4.1-011, Meeting Info.: 71st Annual Meeting of the American-Academy-of-Neurology (AAN). Philadelphia, PA, USA. May 4-10, 2019. Amer Acad Neurol. CODEN: NEURAI, ISSN: 0028-3878. E-ISSN: 1526-632X.

Nomoto, M. et al., "Comparison of zonisamide with non-levodopa, anti-Parkinson's disease drugs in the incidence of Parkinson's disease-relevant symptoms", Journal of the Neurological Sciences, (Oct. 15, 2019) vol. 405, Supp. Supplement, pp. 24-25. Meeting Info: World Congress of Neurology (WCN 2019). Dubai, United Arab Emirates, Oct. 27, 2019-Oct. 31, 2019 ISSN: 0022-510X: E-ISSN: 1878-5883.

Hasegawa, K. et al., "Zonisamide Improves Parkinsonism in dementia with lewy bodies (DLB): A randomized double-blind placebocontrolled phase 3 study",Parkinsonism and Related Disorders, (Jan. 2018) vol. 46, Supp. Supplement 2, pp. e26. Abstract No. OP-5-11, Meeting Info: 22nd World Congress of the International Association of Parkinsonism and Related Disorders. Ho Chi Minh City, Viet Nam. Nov. 12, 2017-Nov. 15, 2017 ISSN: 1873-5126.

Murata, Miho et al., "Adjunct zonisamide to levodopa for DLB parkinsonism: A randomized double-blind phase 2 study", Neurology, (Feb. 20, 2018) vol. 90, No. 8, pp. e664-e672. E-ISSN: 1528-632X.

Nishimura, Yuhei et al., "Overcoming obstacles to drug repositioning in Japan", Frontiers in Pharmacology, (Oct. 11, 2017) vol. 8, No. OCT, am. 729.Refs: 53 E-ISSN: 1663-9812.

Tanaka, Tomoyuki et al., "Simple N,N-dimethyl phenylsulfonamides show potent anticonvulsant effect in two standard epilepsy models", Bioorganic and Medicinal Chemistry Letters, (2017) vol. 27, No. 1, pp. 94-97. Refs: 13 ISSN: 0960-894X: E-ISSN: 1464-3405 CODEN: BMCLE8.

Miyauchl, M. et al., "The effect of zonisamide on abnormal muscle tone during REM sleep in a mouse model of REM sleep behavior disorder", Sleep Medicine, (Dec. 2017) vol. 40, Supp. Supplement 1, pp. e229.Abstract No. Board #075: P6—Wednesday.Meeting Info: 14th World Sleep Congress, Prague, Czech Republic. Oct. 7, 2017-Oct. 11, 2017 ISSN: 1878-5506.

Murata, M. et al., "Zonisamide improves DLB parkinsonism: A randomized double-blind placebo-controlled phase 3 study", Journal of the Neurological Sciences. (Oct. 2017) vol. 381, Supp. Supplement 1, pp. 185-186. Abstract No. 504. Meeting Info: 23rd World Congress of Neurology, WCN 2017, Kyoto, Japan, Sep. 16, 2017-Sep. 21, 2017 ISSN: 1878-5883.

Odawara, T. et al., "Influence of zonisamide on cognition and BPSD of dementia with lewy bodies : A post-hoc analysis of dementia with Lewy bodies PH2 study", Neurodegenerative Diseases, (2017) vol. 17, Supp. Supplement 1, pp. 1496. Abstract No. ADPD7-0096. Meeting Info: 13th International Conference on Alzheimer's and Parkinson's Diseases, AD/PD 2017. Vienna, Austria. Mar. 29, 2017-Apr. 2, 2017 ISSN: 1660-2862.

Murata, Miho et al., "Randomized placebo-controlled trial of zonisamide in patients with Parkinson's disease", Neurology and Clinical Neuroscience, Neuroscience, (Jan. 1, 2016) vol. 4, No. 1 , pp. 10-15, Refs: 14 E-ISSN: 2049-4173.

Odawara, Toshinari et al., "Zonisamide improves parkinsonism without psychiatric deterioration in patients with DLB: A double-blind randomized placebo-controlled study", . American Journal of Geriatric Psychiatry, (Mar. 2016) vol. 24, No. 3, Supp. Supplement 1, pp. S160-S161. Abstract No. NR 30.Meeting Info: 2016 Annual Meeting of the American Association of Geriatric Psychiatry, AAGP 2016. Washington, DC, United States. Mar. 17, 2016-Mar. 20, 2016 ISSN: 1545-7214.

Tanaka, Tomoyuki et al., "Discovery of benzothiazine derivatives as novel, orally-active anti-epileptic drug candidates with broad anticonvulsant effect", Bioorganic and Medicinal Chemistry Letters, (Jul. 22, 2015) vol. 25, No. 20, pp. 4518-4521. Refs: 10 ISSN: 0960-694X; E-ISSN: 1464-3405 CODEN: BMCLE8.

Murata, Miho et al., "Zonisamide improves wearing-off in Parkinson's disease: A randomized, double-blind study", Movement Disorders. (Sep. 1, 2015) vol. 30, No. 10, pp. 1343-1350. Refs: 28 ISSN: 0885-3185; E-ISSN: 1531-8257 CODEN: MOVDEA.

Zhu, Gang et al., "Rats harboring S284L Chrna4 mutation show attenuation of synaptic and extrasynaptic GABAergic transmission and exhibit the nocturnal frontal lobe epilepsy phenotype", . Journal of Neuroscience, (Nov. 19, 2008) vol. 28, No. 47, pp. 12465-12476. Refs: 48 ISSN: 0270-6474: E-ISSN: 0270-6474 CODEN: JNRSDS.

Kaminski P et al., "Development of a fluorescence polarization immunoassay for zonisamide" Clinical Chemistry, (Jun. 2003) vol. 49, No. 6, Part 2, Supp. [S], pp. A122-A122. ISSN: 0009-9147.

Miura, Yoshiki et al., "Clobazam shows a different antiepileptic action profile from clonazepam and zonisamide in Ihara epileptic rats", Epilepsy Research, (2002) vol. 49, No. 3, pp. 189-202. Refs: 34 ISSN: 0920-1211 CODEN: EPIRE8.

Someya T et al., "Establishment of enzyme immunoassay for measuring serum sultopride levels" Ther.Drug Monit. (23, No. 3, 277-81, 2001) 5 Fig. 1 Tab. 13 Ref.ODEN: TDMODV ISSN: 0163-4356.

Akaike K. et al., "Regional accumulation of 14C-zonisamide in rat brain during kainic acid-induced limbic seizures", Epilepsia (41, Suppl. 7, 37, 2000) CODEN: EPILAK ISSN: 0013-9580.

Amano S. et al., "Effects of antiepileptics on two different types of seizures in a novel epileptic mutant rat (Ihara's genetically epileptic rat: IGER)", Epilepsia (40, Suppl. 2. 132, 1999) CODEN: EPILAK ISSN: 0013-9580.

Miura Y et al., "Effects of antiepileptics on two different types of seizures in a novel epileptic mutant rat (IGER)", Jpn.J.Pharmacol. (79, Suppl. 1, 228P, 1999) CODEN: JJPAAZ ISSN: 0021-5198.

Masuda, Yoshinobu et al., "Zonisamide: Pharmacology and clinical efficacy in epilepsy", CNS Drug Reviews. (Winter 1998) vol. 4, No. 4, pp. 341-360. Refs: 110 ISSN: 1080-563X CODEN: COREFS.

Masuda Y. et al., "The novel anticonvulsant zonisamide prevents dopaminergic neurodegeneration induced by MTPT", Jpn.J. Pharmacol. (76, Suppl. I, 119P, 1998) CODEN: JJPAAZ ISSN: 0021-5198.

Minato, Hisao et al., "Protective effect of zonisamide, an antiepileptic drug, against transient focal cerebral ischemia with middle cerebral artery occlusion-reperfusion in rats", Epilepsia, (Sep. 1997) vol. 38, No. 9, pp. 975-980. Refs: 33 ISSN: 0013-9580 CODEN: EPILA.

Buchanan, R. A. et al., "Zonisamide drug interactions", Epilepsia, (1997) vol. 38, No. Suppl. 8, pp. 107. print. Meeting Info.: Annual Meeting of the American Epilepsy Society Boston, Massachusetts, USA Dec. 7-10, 1997 American Epilepsy Society. CODEN: EPILAK. ISSN: 0013-958.

Browne T R. et al., "Zonisamide efficacy in long-term studies", Epilepsia (38, Suppl. 8, 108, 1997) CODEN: EPILAK ISSN: 0013-958.

Padgett C S et al., "Zonisamide efficacy and dose response", Epilepsia (38, Suppl. 8, 107, 1997) CODEN: EPILAK ISSN: 0013-9580.

Mimaki T. et al., "Regional Distribution of C-14 Zonisamide in Rat-Brain", Epilepsy Research, (Mar. 1994) vol. 17, No. 3, pp. 233-236.ISSN: 0920-1211.

Seino M et al., "Zonisamide", Epilepsy Research, (1991) Supp. [3], pp. 169-174. ISSN: 0920-1211.

Kaibe, K. et al., "Competitive binding enzyme immunoassay for zonisamide, a new antiepileptic drug. with selected paired-enzyme labeled antigen and antibody", Clinical Chemistry, (1990) vol. 36, No. 1, pp. 24-27. ISSN: 0009-9147 CODEN: CLCHAU.

Hori, M. et al., "General pharmacology of the novel antiepileptic compound zonisamide. Part 1. Effects on central nervous system",

(56) References Cited

OTHER PUBLICATIONS

Arzneimittel-Forschung (Germany), (1987) vol. 37, pp. 1124-1130. 25 Refs. CODN: ARZNAD. ISSN: 0004-4172.

Ito, T. et al., Effects of zonisamide (AD-810) on tungstic acid gel-induced thalamic generalized seizures and conjugated estrogen-induced cortical spike-wave discharges in cats, Epilepsia, (1986) vol. 27, No. 4, pp. 367-374, ISSN: 0013-9580 CODEN: EPILAK.

Uno, Hitoshi et al., "Studies on 3-substituted 1,2-benzisoxazole derivatives. VII. Catalytic reduction of 3-sulfamoylmethyl-1,2-benzisoxazole and reactions of the resulting products", Chemical & Pharmaceutical Bulletin (1982), 30(1), 333-5 CODEN: CPBTAL: ISSN: 0009-2363.

Uno, H. et al., "Syntheses of 2-sulfamoylmethylbenzoxazole derivatives and determination of their anticonvulsant activities", Chemical and Pharmaceutical Bulletin, (1981) vol. 29, No. 8, pp. 2359-2361. ISSN: 0009-2363 CODEN: CPBTAL.

Kamei, C. et al., "Effects of 3-sulfamoylmethyl-1,2-benzisoxazole (AD-810) and some antiepileptics on the kindled seizures in the neocortex, hippocampus and amygdala in rats", Archives Internationales de Pharmacodynamie et de Therapie, (1981) vol. 249, No. 1, pp. 164-176. ISSN: 0003-9780 CODEN: AIPTAK.

Masuda, Y et al., "Differential antagonisms of anticonvulsants to various components of maximal seizures induced by electroshock or pentylenetetrazol in mice", Journal of Pharmacobio-Dynamics, (1980) vol. 3, No. 10, pp. 526-531, ISSN: 0386-846X CODEN: JOPHDO.

Masuda, Y. et al., "3-Sulfamoylmethyl-1,2-benzisoxazole, a new type of anticonvulsant drug. Pharmacological profile", Arzneimittel-Forschung (Germany), (1980) vol. 30, pp. 477-483. 20 Refs. CODEN: ARZNAD. ISSN: 0004-4172.

Masuda, Y. et al., "3-Suifamoylmethyl-1,2-benzisoxazole, a new type of anticonvulsant drug. Pharmacological profile", Japanese Journal of Pharmacology, (1979) vol. 29, No. Suppl., pp. 30P. ISSN: 0021-5198 CODEN: JJPAAZ.

Ito, T. et al., "3-Suifamoylmethyl-1,2-benzisoxazole, a new type of anticonvulsant drug: Electroencephalographic profile", Japanese Journal of Pharmacology, (1979) vol. 29, No. Suppl., pp. 30P. ISSN: 0021-5198 CODEN: JJPAAZ.

Ritsuko Hanajima et al., "Zonisamide for Treating Parkinson's Disease", 2020 NeuroPsychopharmacotherapy pp. 1-9.

Masahiko Suzuki. et al., "Prescription pattern of anti-Parkinson's disease drugs in Japan based on a nationwide medical claims database", eNeurologicalSci 20 (2020) 100257; pp. 1-7.

Theresa A. Zesiewicz, MD, et al., "A Double-Blind Placebo-Controlled Trial of Zonisamide (Zonegran) in the Treatment of Essential Tremor; *Movement Disorders*", vol. 22, No. 2, 2007; pp. 279-282.

William G. Ondo, MD; "Zonisamide for Essential Tremor"; Clinical Neuropharmacolog, vol. 30, No. 6 Nov.-Dec. 2007; pp. 349-349.

Shuhei Morita, et al., "Effect of zonisamide on essential tremor: a pilot crossover study in comparison with arotinolol"; Parkinisonism and Related Disorders 11 (2005) 101-103.

Adrian Handforth, MD, et al; "Zonisamide for Essential Tremor: An Evaluator-Blinded Study"; Movement Disorders, vol. 24, No. 3, 2009;pp. 437-440.

Side view

BENZISOXAZOLE DERIVATIVE

This application is a continuation of U.S. Ser. No. 17/623,527 filed Dec. 28, 2021, pending, which is a 371 application of PCT/JP2021/025403 filed Jul. 6, 2021 and claims benefit of Japanese Application No. 2020-117236 filed Jul. 7, 2020. The contents of each of these applications are incorporated herein by reference in their entirety.

TECHNICAL FIELD

The present invention relates to a benzisoxazole derivative or a pharmaceutically acceptable salt thereof which has calcium channel inhibitory activity, a pharmaceutical composition comprising the derivative as an active ingredient, or a medicament for treating Parkinson's disease, essential tremor, or neuropathic pain.

BACKGROUND ART

Calcium channel on plasma membrane is one of wide variety of superfamilies of voltage-dependent channel proteins, which is a transmembrane subunit protein for controlling the $Ca^{2+}$ influx from extracellular fluid. Voltage-dependent calcium channels in living cells are classified as L-type (Cav.1) and non-L-type (P/Q type, N-type and R-type) (Cav.2) which are activated in high voltage, and T-type (Cav.3) which is activated in low voltage, depending of the opening voltage. It has been reported that L-type channel is expressed in skeletal muscle, heart, endocrine tissue, brain, retina, etc., non-L-type channel is expressed in neuron, and T-type channel is expressed broadly and abundantly in brain (Non-patent Literature 1).

It has been reported that T-type calcium channel is associated with a variety of diseases and disorders including epilepsy, essential tremor, Parkinson's disease, cerebellar ataxia, neuropathic pain (which includes hyperalgesia and allodynia), nociceptive pain, migraine, schizophrenia, autism, bipolar disorder, depressive disorder, anxiety, sleep disorder, cardiac arrhythmia, hypertension, cancer, diabetes, infertility, and sexual dysfunction (Non-patent Literatures 2, 3, and 4). Now there are a lot of medicaments or methods for treating such diseases and disorders, but many patients thereof are not fully satisfied with the effects of the existing medicaments or methods. Thus, it has been desired to develop a new better medicament for the treatment.

Patent Literatures 1 and 2 disclose benzisoxazole derivatives, but their structures are different from that of the compound of formula (1) shown below.

PRIOR ART

Patent Reference

[Patent Literature 1] JP 53(1978)-077057 A
[Patent Literature 2] U.S. Pat. No. 4,172,896 B

Non-Patent Reference

[Non-patent Literature 1] Pharmacological Reviews 57(4) 397-409 (2005)
[Non-patent Literature 2] Drug Discovery Today 11(5/6) 245-253 (2006)
[Non-patent Literature 3] Neuron 98(3) 466-481 (2018)
[Non-patent Literature 4] Q. Ashton Acton, PhD. (Eds.), Ion Channels-Advances in Research and Application. 2013 Edition. Scholarly Edition™, Atlanta, Ga., pp. 1-106.
[Non-patent Literature 5] ACTA UROLOGICA JAPONICA 57, 125-128 (2011)

SUMMARY OF INVENTION

Technical Problem

The purpose of the present invention may be to provide a compound useful as a medicament for treating various nervous system diseases or psychiatric diseases, for example, a medicament for treating Parkinson's disease, a medicament for treating essential tremor, and a medicament for treating neuropathic pain.

Solution to Problem

The present inventors have extensively studied to reach the above purpose, and then have found that a compound of the formula (1) below has T-type calcium channel inhibitory activity, and also antiparkinsonian effect (i.e., effect for potentiating levodopa action and anti-tremor effect) and anti-essential tremor effect, and additionally have found that the compound is useful for chemotherapy-induced peripheral neuropathy. Based upon the new findings, the present invention has been completed. According to the present invention, a benzisoxazole derivative of the formula (1) below (hereinafter, may be also referred to as "the present compound") may be provided.

The present invention is described as follows.
(Item 1)
A compound of formula (1):

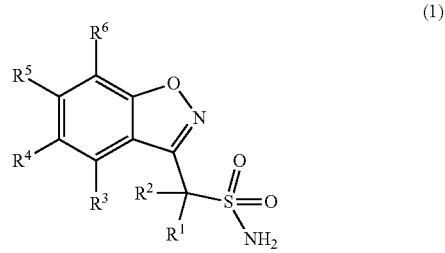

or a pharmaceutically acceptable salt thereof, wherein
$R^1$ is hydrogen, halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy),
$R^2$ is halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), or
$R^1$ and $R^2$ are taken together with the carbon atom to which they are attached to form $C_{3-6}$ cycloalkyl which may be substituted with 1-3 substituents selected independently from the group consisting of halogen, hydroxy, $C_{1-3}$ alkyl, and $C_{1-3}$ alkoxy, and
$R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, C$_{3-6}$ cycloalkyl, and C$_{1-3}$ alkoxy), C$_{3-6}$ cycloalkyl (which may be substituted with 1-3 substituents selected independently from the group consisting of halogen, hydroxy, C$_{1-3}$ alkyl, and C$_{1-3}$ alkoxy), or C$_{1-6}$ alkoxy (which may be substituted with 1-3 substituents selected independently from the group consisting of halogen, hydroxy, C$_{3-6}$ cycloalkyl, and C$_{1-3}$ alkoxy).

(Item 2)

The compound of Item 1 or a pharmaceutically acceptable salt thereof, wherein

R$^1$ is hydrogen, fluorine, C$_{1-6}$ alkyl (which may be substituted with 1-3 substituents selected independently from the group consisting of fluorine, hydroxy, C$_{3-6}$ cycloalkyl, and C$_{1-3}$ alkoxy), or C$_{3-6}$ cycloalkyl (which may be substituted with 1-3 substituents selected independently from the group consisting of fluorine, hydroxy, C$_{1-3}$ alkyl, and C$_{1-3}$ alkoxy), and R$^2$ is fluorine, C$_{1-6}$ alkyl (which may be substituted with 1-3 substituents selected independently from the group consisting of fluorine, hydroxy, C$_{3-6}$ cycloalkyl, and C$_{1-3}$ alkoxy), or C$_{3-6}$ cycloalkyl (which may be substituted with 1-3 substituents selected independently from the group consisting of fluorine, hydroxy, C$_{1-3}$ alkyl, and C$_{1-3}$ alkoxy), or R$^1$ and R$^2$ are taken together with the carbon atom to which they are attached to form C$_{3-6}$ cycloalkyl which may be substituted with 1-3 substituents selected independently from the group consisting of fluorine, hydroxy, C$_{1-3}$ alkyl, and C$_{1-3}$ alkoxy.

(Item 3)

The compound of Item 1 or 2 or a pharmaceutically acceptable salt thereof, wherein R$^3$, R$^4$, R$^5$, and R$^6$ are the same or different and are hydrogen, halogen, cyano, nitro, C$_{1-6}$ alkyl (which may be substituted with 1-3 substituents selected independently from the group consisting of fluorine, hydroxy, C$_{3-6}$ cycloalkyl, and C$_{1-3}$ alkoxy), C$_{3-6}$ cycloalkyl (which may be substituted with 1-3 substituents selected independently from the group consisting of fluorine, hydroxy, C$_{1-3}$ alkyl, and C$_{1-3}$ alkoxy), or C$_{1-6}$ alkoxy (which may be substituted with 1-3 substituents selected independently from the group consisting of fluorine, hydroxy, C$_{3-6}$ cycloalkyl, and C$_{1-3}$ alkoxy).

(Item 4)

The compound of any one of Items 1 to 3 or a pharmaceutically acceptable salt thereof, wherein R$^1$ is hydrogen, fluorine, or C$_{1-6}$ alkyl which may be substituted with 1-3 substituents selected independently from the group consisting of fluorine, hydroxy, and C$_{1-3}$ alkoxy, and R$^2$ is fluorine, or C$_{1-6}$ alkyl which may be substituted with 1-3 substituents selected independently from the group consisting of fluorine, hydroxy, and C$_{1-3}$ alkoxy, or R$^1$ and R$^2$ are taken together with the carbon atom to which they are attached to form C$_{3-6}$ cycloalkyl which may be substituted with 1-3 substituents selected independently from the group consisting of fluorine, hydroxy, C$_{1-3}$ alkyl, and C$_{1-3}$ alkoxy.

(Item 5)

The compound of any one of Items 1 to 4 or a pharmaceutically acceptable salt thereof, wherein R$^3$, R$^4$, R$^5$, and R$^6$ are the same or different and are hydrogen, halogen, or C$_{1-3}$ alkoxy which may be substituted with 1-3 fluorine.

(Item 6)

The compound of Item 1 or a pharmaceutically acceptable salt thereof, wherein

R$^1$ is hydrogen, fluorine, or C$_{1-6}$ alkyl which may be substituted with 1-3 substituents selected independently from the group consisting of fluorine, hydroxy, and C$_{1-3}$ alkoxy, R$^2$ is fluorine, or C$_{1-6}$ alkyl which may be substituted with 1-3 substituents selected independently from the group consisting of fluorine, hydroxy, and C$_{1-3}$ alkoxy, or R$^1$ and R$^2$ are taken together with the carbon atom to which they are attached to form C$_{3-6}$ cycloalkyl which may be substituted with 1-3 substituents selected independently from the group consisting of fluorine, hydroxy, C$_{1-3}$ alkyl, and C$_{1-3}$ alkoxy, and R$^3$, R$^4$, R$^5$, and R$^6$ are the same or different and are hydrogen, halogen, or C$_{1-3}$ alkoxy which may be substituted with 1-3 fluorine.

(Item 7)

The compound of Item 1 or a pharmaceutically acceptable salt thereof, wherein the compound is selected from the following compounds:

1-(benzo[d]isoxazol-3-yl)ethane-1-sulfonamide (Example 1),
2-(benzo[d]isoxazol-3-yl)propane-2-sulfonamide (Example 2),
benzo[d]isoxazol-3-yl-fluoromethane-sulfonamide (Example 3),
benzo[d]isoxazol-3-yl-difluoromethane-sulfonamide (Example 4),
1-(benzo[d]isoxazol-3-yl)cyclopropane-1-sulfonamide (Example 5),
1-(benzo[d]isoxazol-3-yl)propane-1-sulfonamide (Example 6),
1-(benzo[d]isoxazol-3-yl)butane-1-sulfonamide (Example 7),
1-(benzo[d]isoxazol-3-yl)-1-fluoroethane-1-sulfonamide (Example 8),
1-(benzo[d]isoxazol-3-yl)-2-methylpropane-1-sulfonamide (Example 9),
1-(5-methoxybenzo[d]isoxazol-3-yl)ethane-1-sulfonamide (Example 10),
1-(5-fluorobenzo[d]isoxazol-3-yl)ethane-1-sulfonamide (Example 11),
1-(5-chlorobenzo[d]isoxazol-3-yl)ethane-1-sulfonamide (Example 12),
(R)-1-(benzo[d]isoxazol-3-yl)ethane-1-sulfonamide, or
(S)-1-(benzo[d]isoxazol-3-yl)ethane-1-sulfonamide (Example 13 or 14).

[Item 7a]

The compound of Item 1 or a pharmaceutically acceptable salt thereof, wherein the compound is selected from the following compounds:

1-(1,2-benzoxazol-3-yl)ethane-1-sulfonamide (Example 1),
2-(1,2-benzoxazol-3-yl)propane-2-sulfonamide (Example 2),
1-(1,2-benzoxazol-3-yl)-1-fluoromethane-sulfonamide (Example 3),
1-(1,2-benzoxazol-3-yl)-1,1-difluoromethane-sulfonamide (Example 4),
1-(1,2-benzoxazol-3-yl)cyclopropane-1-sulfonamide (Example 5),
1-(1,2-benzoxazol-3-yl)propane-1-sulfonamide (Example 6),
1-(1,2-benzoxazol-3-yl)butane-1-sulfonamide (Example 7),
1-(1,2-benzoxazol-3-yl)-1-fluoroethane-1-sulfonamide (Example 8), 1-(1,2-benzoxazol-3-yl)-2-methylpropane-1-sulfonamide (Example 9),
1-(5-methoxy-1,2-benzoxazol-3-yl)ethane-1-sulfonamide (Example 10),
1-(5-fluoro-1,2-benzoxazol-3-yl)ethane-1-sulfonamide (Example 11),
1-(5-chloro-1,2-benzoxazol-3-yl)ethane-1-sulfonamide (Example 12),
(1R)-1-(1,2-benzoxazol-3-yl)ethane-1-sulfonamide (Example 13), or
(1S)-1-(1,2-benzoxazol-3-yl)ethane-1-sulfonamide (Example 14).

[Item 8]
The compound of Item 1 or a pharmaceutically acceptable salt thereof, wherein the compound is selected from the following compounds:
1-(benzo[d]isoxazol-3-yl)ethane-1-sulfonamide (Example 1),
2-(benzo[d]isoxazol-3-yl)propane-2-sulfonamide (Example 2),
benzo[d]isoxazol-3-yl-fluoromethane-sulfonamide (Example 3),
benzo[d]isoxazol-3-yl-difluoromethane-sulfonamide (Example 4),
1-(benzo[d]isoxazol-3-yl)cyclopropane-1-sulfonamide (Example 5),
1-(benzo[d]isoxazol-3-yl)-1-fluoroethane-1-sulfonamide (Example 8),
(R)-1-(benzo[d]isoxazol-3-yl)ethane-1-sulfonamide, or
(S)-1-(benzo[d]isoxazol-3-yl)ethane-1-sulfonamide (Example 13 or 14).

[Item 8a]
The compound of Item 1 or a pharmaceutically acceptable salt thereof, wherein the compound is selected from the following compounds:
1-(1,2-benzoxazol-3-yl)ethane-1-sulfonamide (Example 1),
2-(1,2-benzoxazol-3-yl)propane-2-sulfonamide (Example 2),
1-(1,2-benzoxazol-3-yl)-1-fluoromethane-sulfonamide (Example 3),
1-(1,2-benzoxazol-3-yl)-1,1-difluoromethane-sulfonamide (Example 4),
1-(1,2-benzoxazol-3-yl)cyclopropane-1-sulfonamide (Example 5),
1-(1,2-benzoxazol-3-yl)-1-fluoroethane-1-sulfonamide (Example 8),
(1R)-1-(1,2-benzoxazol-3-yl)ethane-1-sulfonamide (Example 13), or
(1S)-1-(1,2-benzoxazol-3-yl)ethane-1-sulfonamide (Example 14).

[Item 9]
The compound of Item 1 or a pharmaceutically acceptable salt thereof, wherein the compound is selected from the following compounds:
1-(benzo[d]isoxazol-3-yl)ethane-1-sulfonamide (Example 1),
2-(benzo[d]isoxazol-3-yl)propane-2-sulfonamide (Example 2),
1-(benzo[d]isoxazol-3-yl)cyclopropane-1-sulfonamide (Example 5),
(R)-1-(benzo[d]isoxazol-3-yl)ethane-1-sulfonamide, or
(S)-1-(benzo[d]isoxazol-3-yl)ethane-1-sulfonamide (Example 13 or 14).

[Item 9a]
The compound of Item 1 or a pharmaceutically acceptable salt thereof, wherein the compound is selected from the following compounds:
1-(1,2-benzoxazol-3-yl)ethane-1-sulfonamide (Example 1),
2-(1,2-benzoxazol-3-yl)propane-2-sulfonamide (Example 2),
1-(1,2-benzoxazol-3-yl)cyclopropane-1-sulfonamide (Example 5),
(1R)-1-(1,2-benzoxazol-3-yl)ethane-1-sulfonamide (Example 13), or
(1S)-1-(1,2-benzoxazol-3-yl)ethane-1-sulfonamide (Example 14).

[Item 10]
A pharmaceutical composition comprising the compound of any one of Items 1 to 9 which include Items 7a to 9a, or a pharmaceutically acceptable salt thereof.

[Item 11]
A medicament for treating and/or preventing nervous system diseases or psychiatric diseases which are initiated by abnormality of T-type calcium channel, comprising the compound of any one of Items 1 to 9 which include Items 7a to 9a, or a pharmaceutically acceptable salt thereof as an active ingredient.

[Item 12]
The medicament of Item 11, wherein the nervous system diseases or psychiatric diseases which are initiated by abnormality of T-type calcium channel are various diseases or disorders, including epilepsy; seizure disorder; motor dysfunction (e.g. muscle spasm-related disorder including convulsion; tremor; essential tremor; Huntington's disease; myoclonus; tic; restless legs syndrome; and dystonia); movement disorder including akinesia and stiff-man syndrome, and parkinsonism (which includes Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), episodic and drug-induced parkinsonism, postencephalitic parkinsonism, progressive supranuclear palsy, multiple system atrophy, corticobasal degeneration, dementia with Lewy body, cerebellar ataxia, parkinsonism-ALS dementia complex, and basal ganglia calcification); drug-induced dyskinesia; nociceptive pain (including traumatic pain, migraine, headache, chronic pain (e.g. low back pain, rheumatoid arthralgia, fibromyalgia, osteoarthritis, and the like) and inflammatory pain); neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain); fatigue (e.g. Parkinson fatigue, multiple sclerosis fatigue, fatigue caused by sleep disorder or circadian rhythm disorder, chronic fatigue syndrome including drug-induced parkinsonism, and the like); migraine; schizophrenia; autism; Gilles de la Tourette syndrome; bipolar disorder; depressive disorder; anxiety (including generalized anxiety disorder, panic disorder, and obsessive-compulsive disorder); sleep disorder (including insomnia, hypersomnia, narcolepsy, and REM sleep disorder); cardiac arrhythmia; hypertension; cancer; diabetes; infertility; and sexual dysfunction.

[Item 12a]
The medicament of Item 11, wherein the nervous system diseases or psychiatric diseases which are initiated by abnormality of T-type calcium channel are various diseases or disorders, including epilepsy; seizure disorder; motor dysfunction (e.g. muscle spasm-related disorder including convulsion; tremor; essential tremor; Huntington's disease; myoclonus; tic; restless legs syndrome; and dystonia); movement disorder including akinesia and stiff-man syndrome, and parkinsonism (which includes Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), episodic and drug-induced parkinsonism, postencephalitic parkinsonism, progressive supranuclear palsy, multiple system atrophy, corticobasal degeneration, dementia with Lewy body, cerebellar ataxia, parkinsonism-ALS dementia complex, and basal ganglia calcification); levodopa-induced dyskinesia in Parkinson's disease; drug-induced dyskinesia; nociceptive pain (including traumatic pain, migraine, headache, chronic pain (e.g. low back pain, rheumatoid arthralgia, fibromyalgia, osteoarthritis, and the like), inflammatory pain); neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain); fatigue (e.g. Parkinson fatigue, multiple sclerosis fatigue, fatigue caused by sleep disorder or circadian rhythm disorder, chronic fatigue syndrome including drug-induced parkinsonism, and the like); migraine; schizophrenia; autism; Gilles de la Tourette syndrome; bipolar disorder; depressive disorder; anxiety (including generalized anxiety disorder, panic disorder, and obsessive-compulsive disorder); sleep disorder (including insomnia, hypersomnia, narcolepsy, and REM sleep disorder); sleep disorder in depressive disorder; cardiac arrhythmia; hypertension; cancer; diabetes; infertility; and sexual dysfunction.

[Item 13]

The medicament of Item 11, wherein the nervous system diseases or psychiatric diseases which are initiated by abnormality of T-type calcium channel are Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), essential tremor, or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, hyperalgesia or allodynia associated with neuropathic pain).

[Item 13a]

The medicament of Item 11, wherein the nervous system diseases or psychiatric diseases which are initiated by abnormality of T-type calcium channel are Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), levodopa-induced dyskinesia in Parkinson's disease, essential tremor, anxiety (including generalized anxiety disorder), or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain).

[Item 14]

The medicament of Item 11, wherein the nervous system diseases or psychiatric diseases which are initiated by abnormality of T-type calcium channel are tremor in Parkinson's disease, essential tremor, or chemotherapy-induced peripheral neuropathy.

[Item 14a]

The medicament of Item 11, wherein the nervous system diseases or psychiatric diseases which are initiated by abnormality of T-type calcium channel are Parkinson's disease (including tremor, muscle stiffness/muscle rigidity, akinesia/bradykinesia, and impairment of postural reflex), essential tremor, or chemotherapy-induced peripheral neuropathy.

[Item 15]

A method for treating and/or preventing nervous system diseases or psychiatric diseases which are initiated by abnormality of T-type calcium channel, comprising administering a therapeutically effective amount of the compound of any one of Items 1 to 9 which include Items 7a to 9a, or a pharmaceutically acceptable salt thereof to a patient in need thereof.

[Item 16]

Use of the compound of any one of Items 1 to 9 which include Items 7a to 9a or a pharmaceutically acceptable salt thereof, in the manufacture of a medicament for treating and/or preventing nervous system diseases or psychiatric diseases which are initiated by abnormality of T-type calcium channel.

[Item 17]

The compound of any one of Items 1 to 9 which include Items 7a to 9a or a pharmaceutically acceptable salt thereof for use in treating and/or preventing nervous system diseases or psychiatric diseases which are initiated by abnormality of T-type calcium channel.

[Item 18]

A method for treating and/or preventing Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), essential tremor, or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, hyperalgesia or allodynia associated with neuropathic pain), comprising administering a therapeutically effective amount of the compound of any one of Items 1 to 9 which include Items 7a to 9a, or a pharmaceutically acceptable salt thereof to a patient in need thereof.

[Item 18a]

A method for treating and/or preventing Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), levodopa-induced dyskinesia in Parkinson's disease, essential tremor, anxiety (including generalized anxiety disorder), or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain), comprising administering a therapeutically effective amount of the compound of any one of Items 1 to 9 which include Items 7a to 9a, or a pharmaceutically acceptable salt thereof to a patient in need thereof.

[Item 19]

Use of the compound of any one of Items 1 to 9 which include Items 7a to 9a or a pharmaceutically acceptable salt thereof, in the manufacture of a medicament for treating and/or preventing Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), essential tremor, or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, hyperalgesia or allodynia associated with neuropathic pain).

[Item 19a]

Use of the compound of any one of Items 1 to 9 which include Items 7a to 9a or a pharmaceutically acceptable salt thereof, in the manufacture of a medicament for treating and/or preventing Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), levodopa-induced dyskinesia in Parkinson's disease, essential tremor, anxiety (including generalized anxiety disorder), or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain).

[Item 20]

The compound of any one of Items 1 to 9 which include Items 7a to 9a or a pharmaceutically acceptable salt thereof for use in treating and/or preventing Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), essential tremor, or neuropathic pain(zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, hyperalgesia or allodynia associated with neuropathic pain).

[Item 20a]

The compound of any one of Items 1 to 9 which include Items 7a to 9a or a pharmaceutically acceptable salt thereof for use in treating and/or preventing Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), levodopa-induced dyskinesia in Parkinson's disease, essential tremor, anxiety (including generalized anxiety disorder), or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain).

[Item 21]

A method for treating and/or preventing tremor in Parkinson's disease, essential tremor, or chemotherapy-induced peripheral neuropathy, comprising administering a therapeutically effective amount of the compound of any one of Items 1 to 9 which include Items 7a to 9a, or a pharmaceutically acceptable salt thereof to a patient in need thereof.

[Item 21a]

A method for treating and/or preventing Parkinson's disease (including tremor, muscle stiffness/muscle rigidity, akinesia/bradykinesia, and impairment of postural reflex), essential tremor, or chemotherapy-induced peripheral neuropathy, comprising administering a therapeutically effective amount of the compound of any one of Items 1 to 9 which include Items 7a to 9a, or a pharmaceutically acceptable salt thereof to a patient in need thereof.

[Item 22]

Use of the compound of any one of Items 1 to 9 which include Items 7a to 9a or a pharmaceutically acceptable salt thereof, in the manufacture of a medicament for treating and/or preventing tremor in Parkinson's disease, essential tremor, or chemotherapy-induced peripheral neuropathy.

[Item 22a]

Use of the compound of any one of Items 1 to 9 which include Items 7a to 9a or a pharmaceutically acceptable salt thereof, in the manufacture of a medicament for treating and/or preventing Parkinson's disease (including tremor, muscle stiffness/muscle rigidity, akinesia/bradykinesia, and impairment of postural reflex), essential tremor, or chemotherapy-induced peripheral neuropathy.

[Item 23]

The compound of any one of Items 1 to 9 which include Items 7a to 9a or a pharmaceutically acceptable salt thereof for use in treating and/or preventing tremor in Parkinson's disease, essential tremor, or chemotherapy-induced peripheral neuropathy.

[Item 23a]

The compound of any one of Items 1 to 9 which include Items 7a to 9a or a pharmaceutically acceptable salt thereof for use in treating and/or preventing Parkinson's disease (including tremor, muscle stiffness/muscle rigidity, akinesia/bradykinesia, and impairment of postural reflex), essential tremor, or chemotherapy-induced peripheral neuropathy.

[Item 24]

A medicament for treating a disease associated with abnormality of T-type calcium channel, comprising the compound of any one of Items 1 to 9 which include Items 7a to 9a, or a pharmaceutically acceptable salt thereof, which is used in combination with at least one drug selected from the drug-group classified as drugs for treating Parkinson's disease, drugs for treating essential tremor, or drugs for treating neuropathic pain.

[Item 25]

A medicament comprising the compound of any one of Items 1 to 9 which include Items 7a to 9a, or a pharmaceutically acceptable salt thereof with at least one drug selected from the drug-group classified as drugs for treating Parkinson's disease, drugs for treating essential tremor, or drugs for treating neuropathic pain.

[Item 26]

A medicament for treating nervous system disease or psychiatric disease, comprising the compound of any one of Items 1 to 9 which include Items 7a to 9a, or a pharmaceutically acceptable salt thereof, which is used in combination with at least one drug selected from the drug-group classified as drugs for treating Parkinson's disease, drugs for treating essential tremor, or drugs for treating neuropathic pain.

(Item 27)

A process for preparing a compound of formula (2):

or a pharmaceutically acceptable salt thereof, wherein $R^{1A}$ is hydrogen, halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), $R^{2A}$ is halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), provided that $R^{1A}$ and $R^{2A}$ are different, and $R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, hydroxy, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy), which comprises Steps 1 to 3 below, (Step 1) reacting a compound of formula (3):

or a salt thereof, wherein $R^{1A}$, $R^{2A}$, $R^3$, $R^4$, $R^5$, and $R^6$ are as defined above, and a compound of formula (4a) or (4b):

$$R^7\text{—SH} \quad (4a)$$

$$R^7\text{—S—S—}R^7 \quad (4b)$$

or a salt thereof, wherein $R^7$ is a leaving group selected from 2-(methoxycarbonyl)ethyl, mesitylenecarbonyloxymethyl, 2-benzothiazolyl (the benzene ring of which may be substituted with 1-3 substituents selected independently from the group consisting of halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{1-6}$ alkoxy (which may be substituted with 1-3 substituents selected independently from the group consisting of halogen, hydroxy, $C_{3-6}$ cycloalkyl, and $C_{1-3}$ alkoxy), hydroxy, cyano, nitro, amino (which may be substituted with 1-2 $C_{1-3}$ alkyl), carboxylic acid, carbamoyl (the amino moiety of which may be substituted with 1-2 $C_{1-3}$ alkyl), and $C_{1-6}$ alkoxycarbonyl), 2-pyridyl, 2-pyrimidinyl, or 2-(trimethylsilyl)ethyl, which can release a sulfinic acid salt in the reaction to prepare a compound of formula (5):

or a salt thereof, wherein $R^{1A}$, $R^{2A}$, $R^3$, $R^4$, $R^5$, $R^6$, and $R^7$ are as defined above, (Step 2) oxidizing the compound of formula (5) or a salt thereof to prepare a compound of formula (6):

or a salt thereof, wherein $R^{1A}$, $R^{2A}$, $R^3$, $R^4$, $R^5$, $R^6$, and $R^7$ are as defined above, and (Step 3) removing $R^7$ from the compound of formula (6) or a salt thereof and sulfonamidating the site to prepare the compound of formula (2) or a pharmaceutically acceptable salt thereof.

(Item 28)

The process of Item 27, which further comprises the following step;

(Step 4a) optically-selectively hydrolyzing a compound of formula (7):

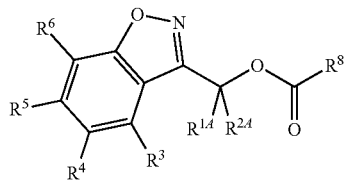

(7)

or a salt thereof, wherein $R^{1A}$, $R^{2A}$, $R^3$, $R^4$, $R^5$, and $R^6$ are as defined in Item 27, and $R^8$ is $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{1-6}$ alkoxy, or $C_{1-6}$ alkylcarbonyloxymethoxy, with a hydrolase selected from lipase, esterase, amidase, or protease to prepare the compound of formula (3).

(Item 29)

The process of Item 27, wherein $R^{1A}$ is hydrogen, which further comprises the following step;

(Step 4b) optically-selectively reducing a compound of formula (8):

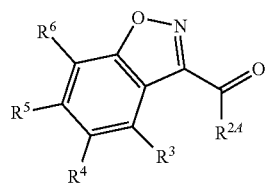

(8)

or a salt thereof, wherein $R^{2A}$, $R^3$, $R^4$, $R^5$, and $R^6$ are as defined in Item 27, with reductase and a coenzyme selected from NADH or NADPH to prepare the compound of formula (3).

(Item 30)

The process of any one of Items 27 to 29, wherein $R^7$ is 2-benzothiazolyl.

(Item 31)

The process of Item 28 or 30, wherein $R^8$ is methyl, and the hydrolase is lipase.

(Item 32)

The process of Item 29 or 30, wherein $R^{2A}$ is methyl, and the reductase is carbonyl reductase or alcohol dehydrogenase.

(Item 33)

A process for preparing a compound of formula (2):

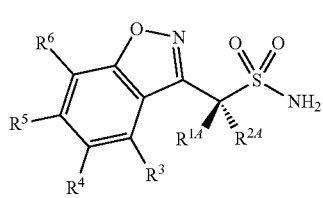

(2)

or a pharmaceutically acceptable salt thereof, wherein $R^{1A}$ is hydrogen, halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), $R^{2A}$ is halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), provided that $R^{1A}$ and $R^{2A}$ are different, and $R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, hydroxy, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy), which comprises Steps 1 to 2 below, (Step 1) reacting a compound of formula (9):

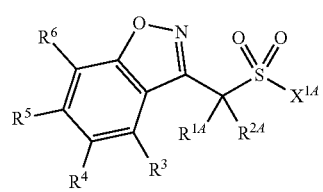

(9)

or a salt thereof, wherein $R^{1A}$, $R^{2A}$, $R^3$, $R^4$, $R^5$, and $R^6$ are as defined above, and $X^{1A}$ is halogen, and an optically-active compound of formula (10):

(10)

or a salt thereof, wherein $P^{1A}$ is 2-indanol-1-yl, 2-phenylethan-1-ol-2-yl, or 3-methylbutan-1-ol-2-yl, $P^{2A}$ is hydrogen or benzyl (the benzene ring of which may be substituted with 1-5 substituents selected independently from the group consisting of halogen, $C_{1-6}$ alkyl, and $C_{1-6}$ alkoxy, and dividing the prepared diastereomers to prepare a compound of formula (11):

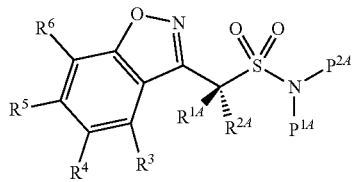

(11)

or a salt thereof, wherein $R^{1A}$, $R^{2A}$, $R^3$, $R^4$, $R^5$, $R^6$, $P^{1A}$, and $P^{2A}$ are as defined above, and (Step 2) deprotecting the compound of formula (11) or a salt thereof to prepare the compound of formula (2) or a pharmaceutically acceptable salt thereof.

(Item 34)

The process of Item 33, wherein $R^{1A}$ is hydrogen, and $R^{2A}$ is methyl.

(Item 35)

The process of Item 33 or 34, wherein $P^{1A}$ is 2-indanol-1-yl, and $P^{2A}$ is hydrogen.

(Item 36)

A process for preparing a compound of formula (2-1):

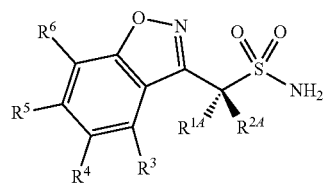

(2-1)

or a pharmaceutically acceptable salt thereof, wherein $R^{1A}$ is hydrogen, halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), $R^{2A}$ is halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), provided that $R^{1A}$ and $R^{2A}$ are different, and $R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, hydroxy, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy), which comprises Steps 1 to 3 below, (Step 1) reacting a compound of formula (3-1):

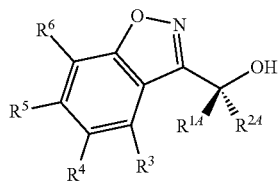

(3-1)

or a salt thereof, wherein $R^{1A}$, $R^{2A}$, $R^3$, $R^4$, $R^5$, and $R^6$ are as defined above, and a compound of formula (4a) or (4b):

$R^7$—SH　　(4a)

$R^7$—S—S—$R^7$　　(4b)

or a salt thereof, wherein $R^7$ is a leaving group selected from 2-(methoxycarbonyl)ethyl, mesitylenecarbonyloxymethyl, 2-benzothiazolyl (the benzene ring of which may be substituted with 1-3 substituents selected independently from the group consisting of halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{1-6}$ alkoxy (which may be substituted with 1-3 substituents selected independently from the group consisting of halogen, hydroxy, $C_{3-6}$ cycloalkyl, and $C_{1-3}$ alkoxy), hydroxy, cyano, nitro, amino (which may be substituted with 1-2 $C_{1-3}$ alkyl), carboxylic acid, carbamoyl (the amino moiety of which may be substituted with 1-2 $C_{1-3}$ alkyl), and $C_{1-6}$ alkoxycarbonyl), 2-pyridyl, 2-pyrimidinyl, or 2-(trimethylsilyl)ethyl, which can release a sulfinic acid salt in the reaction to prepare a compound of formula (5-1):

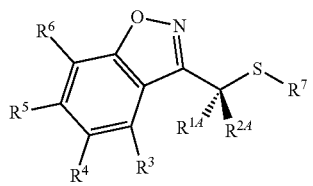

(5-1)

or a salt thereof, wherein $R^{1A}$, $R^{2A}$, $R^3$, $R^4$, $R^5$, $R^6$, and $R^7$ are as defined above, (Step 2) oxidizing the compound of formula (5-1) or a salt thereof to prepare a compound of formula (6-1):

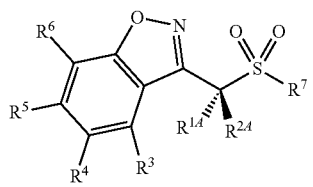

(6-1)

or a salt thereof, wherein $R^{1A}$, $R^{2A}$, $R^3$, $R^4$, $R^5$, $R^6$, and $R^7$ are as defined above, and (Step 3) removing $R^7$ from the compound of formula (6-1) or a salt thereof and sulfonamidating the site to prepare the compound of formula (2-1) or a pharmaceutically acceptable salt thereof.

[Item 37]

The process of Item 36, which further comprises the following step;

(Step 4a) optically-selectively hydrolyzing a compound of formula (7):

(7)

or a salt thereof, wherein $R^{1A}$, $R^{2A}$, $R^3$, $R^4$, $R^5$, and $R^6$ are as defined in Item 36, $R^8$ is $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{1-6}$ alkoxy, or $C_{1-6}$ alkylcarbonyloxymethoxy, with a hydrolase selected from lipase, esterase, amidase, or protease to prepare the compound of formula (3-1).

(Item 38)

The process of Item 36, wherein $R^{1A}$ is hydrogen, which further comprises the following step;

(Step 4b) optically-selectively reducing a compound of formula (8):

(8)

or a salt thereof, wherein $R^{2A}$, $R^3$, $R^4$, $R^5$, and $R^6$ are as defined in Item 36, with reductase and a coenzyme selected from NADH or NADPH to prepare the compound of formula (3-1).

(Item 39)

The process of any one of Items 36 to 38, wherein is $R^7$ is 2-benzothiazolyl.

(Item 40)

The process of Item 37 or 39, wherein $R^8$ is methyl, and the hydrolase is lipase.

(Item 41)

The process of Item 38 or 39, wherein $R^{2A}$ is methyl, and the reductase is carbonyl reductase or alcohol dehydrogenase.

(Item 42)

A process for preparing a compound of formula (2-1):

(2-1)

or a pharmaceutically acceptable salt thereof, wherein $R^{1A}$ is hydrogen, halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), $R^{2A}$ is halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), provided that $R^{1A}$ and $R^{2A}$ are different, and $R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, hydroxy, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy), which comprises Steps 1 to 2 below, (Step 1) reacting a compound of formula (9):

(9)

or a salt thereof, wherein $R^{1A}$, $R^{2A}$, $R^3$, $R^4$, $R^5$, and $R^6$ are as defined above, and $X^{1A}$ is halogen, and an optically-active compound of formula (10):

(10)

or a salt thereof, wherein $P^{1A}$ is 2-indanol-1-yl, 2-phenylethan-1-ol-2-yl, or 3-methylbutan-1-ol-2-yl, $P^{2A}$ is hydrogen or benzyl (the benzene ring of which may be substituted with 1-5 substituents selected independently from the group consisting of halogen, $C_{1-6}$ alkyl, and $C_{1-6}$ alkoxy, and dividing the prepared diastereomers to prepare a compound of formula (11-1):

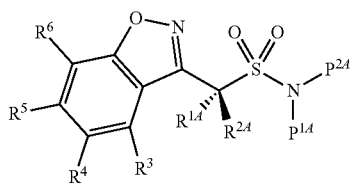
(11-1)

or a salt thereof, wherein $R^{1A}$, $R^{2A}$, $R^3$, $R^4$, $R^5$, $R^6$, $P^{1A}$, and $P^{2A}$ are as defined above, and (Step 2) deprotecting the compound of formula (11-1) or a salt thereof to prepare the compound of formula (2-1) or a pharmaceutically acceptable salt thereof.

(Item 43)

The process of Item 42, wherein $R^{1A}$ is hydrogen, and $R^{2A}$ is methyl.

(Item 44)

The process of Item 42 or 43, wherein $P^{1A}$ is 2-indanol-1-yl, and $P^{2A}$ is hydrogen.

(Item 45)

A process for preparing a compound of formula (2-2):

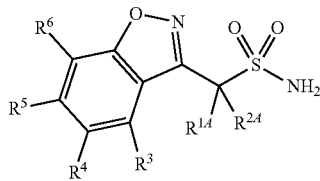
(2-2)

or a pharmaceutically acceptable salt thereof, wherein $R^{1A}$ is hydrogen, halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), $R^{2A}$ is halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), provided that $R^{1A}$ and $R^{2A}$ are different, $R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy), which comprises Steps 1 to 3 below, (Step 1) reacting a compound of formula (3-2):

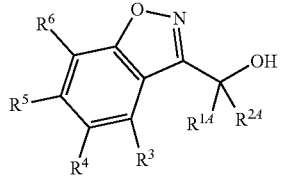
(3-2)

or a salt thereof, wherein $R^{1A}$, $R^{2A}$, $R^3$, $R^4$, $R^5$, and $R^6$ are as defined above, and a compound of formula (4a) or (4b):

$$R^7\text{—SH} \quad (4a)$$

$$R^7\text{—S—S—}R^7 \quad (4b)$$

or a salt thereof, wherein $R^7$ is a leaving group selected from 2-(methoxycarbonyl)ethyl, mesitylenecarbonyloxymethyl, 2-benzothiazolyl (the benzene ring of which may be substituted with 1-3 substituents selected independently from the group consisting of halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{1-6}$ alkoxy (which may be substituted with 1-3 substituents selected independently from the group consisting of halogen, hydroxy, $C_{3-6}$ cycloalkyl, and $C_{1-3}$ alkoxy), hydroxy, cyano, nitro, amino (which may be substituted with 1-2 $C_{1-3}$ alkyl), carboxylic acid, carbamoyl (the amino moiety of which may be substituted with 1-2 $C_{1-3}$ alkyl), and $C_{1-6}$ alkoxycarbonyl), 2-pyridyl, 2-pyrimidinyl, or 2-(trimethylsilyl)ethyl, which can release a sulfinic acid salt in the reaction to prepare a compound of formula (5-2):

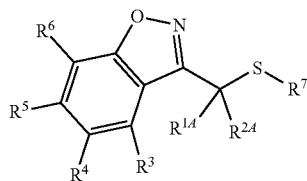
(5-2)

or a salt thereof, wherein $R^{1A}$, $R^{2A}$, $R^3$, $R^4$, $R^5$, $R^6$, and $R^7$ are as defined above, (Step 2) oxidizing the compound of formula (5-2) or a salt thereof to prepare a compound of formula (6-2):

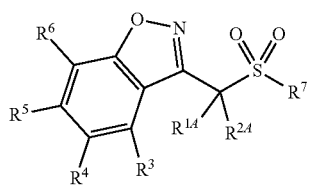
(6-2)

or a salt thereof, wherein $R^{1A}$, $R^{2A}$, $R^3$, $R^4$, $R^5$, $R^6$, and $R^7$ are as defined above, and (Step 3) removing $R^7$ from the compound of formula (6-2) or a salt thereof and sulfonamidating the site to prepare the compound of formula (2-2) or a pharmaceutically acceptable salt thereof.

(Item 46)

The process of Item 45, which further comprises the following step;

(Step 4a) hydrolyzing a compound of formula (7):

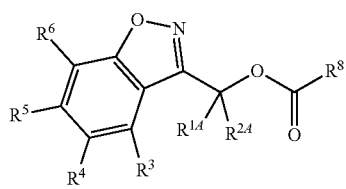

(7)

or a salt thereof, wherein $R^{1A}$, $R^{2A}$, $R^3$, $R^4$, $R^5$, and $R^6$ are as defined in Item 45, and $R^8$ is $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{1-6}$ alkoxy, or $C_{1-6}$ alkylcarbonyloxymethoxy with an acid or a base to prepare the compound of formula (3-2).

(Item 47)

The process of Item 45, wherein $R^{1A}$ is hydrogen, which further comprises the following step;

(Step 4b) reducing a compound of formula (8):

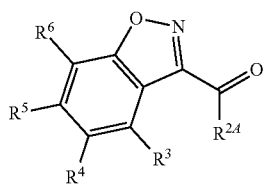

(8)

or a salt thereof, wherein $R^{2A}$, $R^3$, $R^4$, $R^5$, and $R^6$ are as defined in Item 45
with a reducing agent to prepare the compound of formula (3-2).

(Item 48)

The process of any one of Items 45 to 47, wherein $R^7$ is 2-benzothiazolyl.

(Item 49)

The process of any one of Items 45 to 48, wherein $R^{1A}$ is hydrogen, and $R^{2A}$ is methyl.

(Item 50)

A process for preparing a compound of formula (2-2):

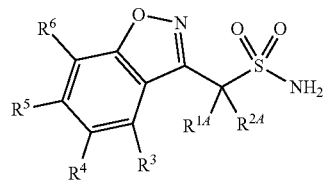

(2-2)

or a pharmaceutically acceptable salt thereof, wherein $R^{1A}$ is hydrogen, halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), $R^{2A}$ is halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy), provided that $R^{1A}$ and $R^{2A}$ are different, $R^3$, $R^4$, BS, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, hydroxy, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy), which comprises Steps 1 to 2 below, (Step 1) reacting a compound of formula (9):

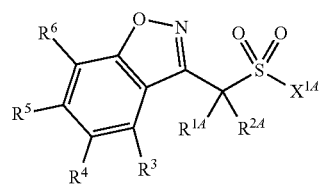

(9)

or a salt thereof, wherein $R^{1A}$, $R^{2A}$, $R^3$, $R^4$, $R^5$, and $R^6$ are as defined above, and $X^{1A}$ is halogen, and a compound of formula (10-2):

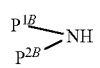

(10-2)

or a salt thereof, wherein $P^1B$ and $P^{2B}$ are the same or different and are hydrogen or a nitrogen-protecting group to prepare a compound of formula (11-2):

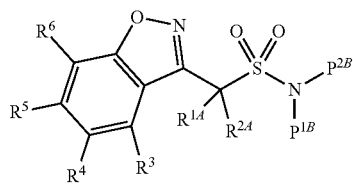

(11-2)

or a salt thereof, wherein $R^{1A}$, $R^{2A}$, $R^3$, $R^4$, $R^5$, $R^6$, $P^{1B}$, and $P^{2B}$ are as defined above, (Step 2) deprotecting the compound of formula (11-2) or a salt thereof to prepare the compound of formula (2-2) or a pharmaceutically acceptable salt thereof, provided that the step is not needed when $P^{1B}$ and $P^{2B}$ are both hydrogen.

(Item 51)

The process of Item 50, wherein $R^{1A}$ is hydrogen, and $R^{2A}$ is methyl.

[Item 52]

(1R)-1-(1,2-Benzoxazol-3-yl)ethane-1-sulfonamide in crystalline form of form I which is characterized by a powder x-ray diffraction pattern having diffraction angle (2θ°) peaks of 5.7°±0.2 and 17.3°±0.2°.

[Item 53]

(1R)-1-(1,2-Benzoxazol-3-yl)ethane-1-sulfonamide in crystalline form of form I which is characterized by a powder x-ray diffraction pattern having four or more diffraction angle (2θ°) peaks selected from 5.7°±0.2, 14.1±0.2°, 17.3°±0.2°, 19.1°±0.2°, 19.3±0.2°, 21.6°±0.2°, 22.5±0.2°, 23.1°±0.2°, 23.3°±0.2°, and 26.5°±0.2°.

[Item 54]

(1R)-1-(1,2-Benzoxazol-3-yl)ethane-1-sulfonamide in crystalline form of form II which is characterized by a powder x-ray diffraction pattern having diffraction angle (2θ°) peaks of 8.7°±0.2° and 17.6°±±0.2°.

[Item 55]

(1R)-1-(1,2-Benzoxazol-3-yl)ethane-1-sulfonamide in crystalline form of form II which is characterized by a powder x-ray diffraction pattern having four or more diffraction angle (2θ°) peaks selected from 8.7°±0.2°, 13.5°±0.2°, 15.5°±0.2°, 17.6°±0.2°, 20.3°±0.2°, 21.6°±0.2°, 22.6°±0.2°, 26.2°±0.2°, 26.8°±0.2°, and 35.2°±0.2°.

[Item 56]

(1R)-1-(1,2-Benzoxazol-3-yl)ethane-1-sulfonamide in crystalline form of form III which is characterized by a powder x-ray diffraction pattern having diffraction angle (2θ°) peaks of 11.1°±0.2° and 20.3°±0.2°.

[Item 57]

(1R)-1-(1,2-Benzoxazol-3-yl)ethane-1-sulfonamide in crystalline form of form III which is characterized by a powder x-ray diffraction pattern having four or more diffraction angle (2θ°) peaks selected from 11.1°±0.2°, 13.8°±0.2°, 17.0°±0.2°, 20.3°±0.2°, 21.4°±0.2°, 22.1°±0.2°, 22.4°±0.2°, 24.8°±0.2°, 26.3°±0.2°, and 27.9°±0.2°.

Effect of the Invention

The present compound has T-type calcium channel inhibitory activity, and thereby it is useful as a medicament for treating and/or preventing various nervous system diseases or psychiatric diseases, for example, epilepsy, essential tremor, Parkinson's disease, cerebellar ataxia, levodopa-induced dyskinesia in Parkinson's disease, drug-induced dyskinesia, neuropathic pain (including hyperalgesia and allodynia), nociceptive pain, migraine, schizophrenia, autism, bipolar disorder, depressive disorder, anxiety, sleep disorder, sleep disorder in depressive disorder, cardiac arrhythmia, hypertension, cancer, diabetes, infertility, sexual dysfunction, etc. In addition, the present compound has potentiating effect of levodopa-induced hyperactivity which is different from the activity derived from monoamine oxidase B (hereinafter, referred to as "MAOB") inhibitory action. And, a preferred compound of the present invention has lower risk of nephrolithiasis because the action inhibiting carbonic anhydrase is attenuated. Thus, for highly safe treatment for Parkinson's disease, the present compound is useful as a combination drug with levodopa preparation. In addition, the present compound inhibited the onset of dyskinesia in a levodopa-induced dyskinesia model, thus the present compound is useful as a medicament for treating and/or preventing Parkinson's disease, which is highly safe unlike existing drugs for combination with levodopa. In addition, the present compound exhibited effectivity for Parkinson's disease tremor model and essential tremor model, thus the present compound is useful as a medicament for treating and/or preventing Parkinson's disease tremor, essential tremor, as well as parkinsonism developed in nervous system diseases or psychiatric diseases. Furthermore, the present compound exhibited antiallodynic effect for oxaliplatin-induced pain model, thus the present compound is also useful as a medicament for treating and/or preventing neuropathic pain (in particular, pain and allodynia in chemotherapy-induced peripheral neuropathy).

BRIEF DESCRIPTION OF DRAWINGS

FIG. 1-1 is a figure when viewed from the front of the benzisoxazole ring.

FIG. 1-2 shows X-ray crystal structure of Example 13 compound, which was obtained in Example 15. FIG. 1-2 is a figure when viewed from the lateral of the benzisoxazole ring.

FIG. 2 shows X-ray powder diffraction pattern of Example 13 (form I), which was obtained in Example 23. The x-axis indicates 2θ value, and the y-axis indicates intensity.

DESCRIPTION OF EMBODIMENTS

Figure 1:
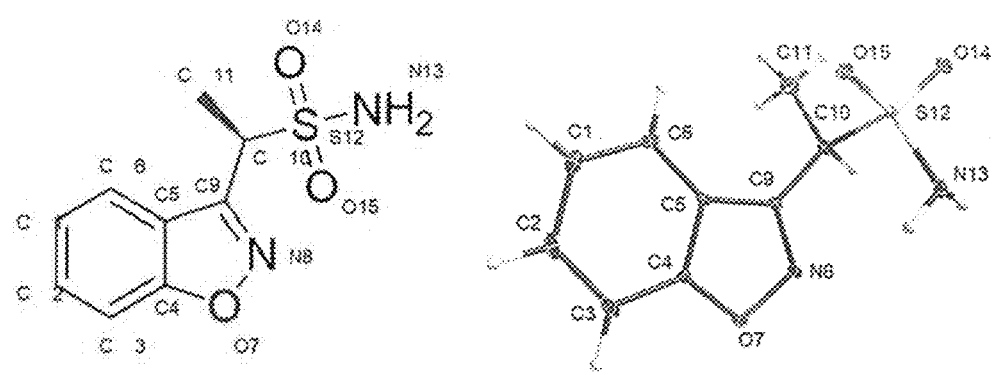
FIG. 1-1 shows X-ray crystal structure of Example 13 compound, which was obtained in Example 15.

Hereinafter, terms used herein are explained as follows.

Unless otherwise specified, the definition of each substituent group also extends over the case that the substituent group is partially included in another substituent group or the case that the substituent group is a substituent attached to another substituent group.

The "halogen atom" includes, for example, fluorine, chlorine, bromine, and iodine. It is preferably fluorine or chlorine, and more preferably fluorine.

The "$C_{1-6}$ alkyl" means straight or branched chain saturated hydrocarbon group having 1 to 6 carbon atoms, and the "$C_6$ alkyl" means alkyl having 6 carbon atoms. The same is applied to the case of the other carbon numbers. The $C_{1-6}$ alkyl includes preferably "$C_{1-4}$ alkyl", more preferably "$C_{1-3}$ alkyl". The "$C_{1-3}$ alkyl" includes, for example, methyl, ethyl, propyl, 1-methylethyl, and the like. The "$C_{1-4}$ alkyl" includes, for example, butyl, 1,1-dimethylethyl, 1-methylpropyl, 2-methylpropyl, and the like, besides the examples listed in the said "$C_{1-3}$ alkyl". The "$C_{1-6}$ alkyl" includes, for example, pentyl, 2-methylbutyl, 3-methylbutyl, 2,2-dimethylpropyl, 1-ethylpropyl, 1,1-dimethylpropyl, 4-methylpentyl, 3-methylpentyl, 2-methylpentyl, 1-methylpentyl, hexyl, and the like, besides the examples listed in the said "$C_{1-4}$ alkyl".

The "$C_{3-6}$ cycloalkyl" means cyclic alkyl having 3 to 6 carbon atoms, which may have a partially-bridged structure. The "$C_{3-6}$ cycloalkyl" includes preferably "$C_{3-5}$ cycloalkyl". The "$C_{3-5}$ cycloalkyl" includes, for example, cyclopropyl, cyclobutyl, cyclopentyl, and the like. The "$C_{3-6}$ cycloalkyl" includes, for example, cyclohexyl and the like, besides the examples listed in the said "$C_{3-5}$ cycloalkyl".

The "$C_{1-6}$ alkoxy" means oxy group substituted with the above "$C_{1-6}$ alkyl". The "$C_{1-6}$ alkoxy" includes preferably "$C_{1-4}$ alkoxy", more preferably "$C_{1-3}$ alkoxy". The "$C_{1-3}$ alkoxy" includes, for example, methoxy, ethoxy, propoxy, 1-methylethoxy, and the like. The "$C_{1-4}$ alkoxy" includes, for example, butoxy, 1,1-dimethylethoxy, 1-methylpropoxy, 2-methylpropoxy, and the like, besides the examples listed in the said "$C_{1-3}$ alkyl". The "$C_{1-6}$ alkoxy" includes, for example, pentyloxy, 3-methylbutoxy, 2-methylbutoxy, 2,2-dimethylpropoxy, 1-ethylpropoxy, 1,1-dimethylpropoxy, 4-methylpentyloxy, 3-methylpentyloxy, 2-methylpentyloxy, 1-methylpentyloxy, hexyloxy, and the like, besides the examples listed in the said "$C_{1-4}$ alkyl".

The "$C_{1-6}$ alkoxycarbonyl" means carbonyl group substituted with the above "$C_{1-6}$ alkoxy". The "$C_{1-6}$ alkoxycarbonyl group" includes preferably "$C_{1-4}$ alkoxycarbonyl", more preferably "$C_{1-3}$ alkoxycarbonyl". The "$C_{1-3}$ alkoxycarbonyl" includes, for example, methoxycarbonyl, ethoxycarbonyl, propoxycarbonyl, 1-methylethoxycarbonyl, and the like. The "$C_{1-4}$ alkoxycarbonyl" includes, for example, butoxycarbonyl, 1,1-dimethylethoxycarbonyl, 1-methylpropoxycarbonyl, and 2-methylpropoxycarbonyl, besides the examples listed in the said "$C_{1-3}$ alkoxycarbonyl". The "$C_{1-6}$ alkoxycarbonyl" includes, for example, pentyloxycarbonyl, 3-methylbutoxycarbonyl, 2-methylbutoxycarbonyl, 2,2-dimethylpropoxycarbonyl, 1-ethylpropoxycarbonyl, 1,1-dimethylpropoxycarbonyl, 4-methylpentyloxycarbonyl, 3-methylpentyloxycarbonyl, 2-methylpentyloxycarbonyl, 1-methylpentyloxycarbonyl, hexyloxycarbonyl, and the like, besides the examples listed in the said "$C_{1-4}$ alkoxycarbonyl".

The "$C_{1-6}$ alkylcarbonyloxymethoxy" means carbonyloxymethoxy group substituted with the above "$C_{1-6}$ alkyl". The "$C_{1-6}$ alkylcarbonyloxymethoxy group" includes preferably "$C_{1-4}$ alkylcarbonyloxymethoxy", more preferably "$C_{1-3}$ alkylcarbonyloxymethoxy". The "$C_{1-3}$ alkylcarbonyloxymethoxy" includes, for example, methylcarbonyloxymethoxy, ethylcarbonyloxymethoxy, propylcarbonyloxymethoxy, 1-methylethylcarbonyloxymethoxy, and the like. The "$C_{1-4}$ alkylcarbonyloxymethoxy" includes, for example, butoxycarbonyloxymethoxy, 1,1-dimethylethylcarbonyloxymethoxy, 1-methylpropylcarbonyloxymethoxy, and 2-methylpropylcarbonyloxymethoxy, besides the examples listed in the said "$C_{1-3}$ alkylcarbonyloxymethoxy". The "$C_{1-6}$ alkylcarbonyloxymethoxy" includes, for example, pentylcarbonyloxymethoxy, 3-methylbutylcarbonyloxymethoxy, 2-methylbutylcarbonyloxymethoxy, 2,2-dimethylpropylcarbonyloxymethoxy, 1-ethylpropylcarbonyloxymethoxy, 1,1-dimethylpropylcarbonyloxymethoxy, 4-methylpentylcarbonyloxymethoxy, 3-methylpentylcarbonyloxymethoxy, 2-methylpentylcarbonyloxymethoxy, 1-methylpentylcarbonyloxymethoxy, hexylcarbonyloxymethoxy, and the like, besides the examples listed in the said "$C_{1-4}$ alkylcarbonyloxymethoxy".

Preferred $R^1$, $R^2$, $R^3$, $R^4$, $R^5$, and $R^6$ are shown below, but the technical scope of the present invention is not limited to the scope of compounds listed below.

In a preferred embodiment of $R^1$ and $R^2$, $R^1$ is hydrogen, fluorine, $C_{1-6}$ alkyl (which may be substituted with 1-3 substituents selected independently from the group consisting of fluorine, hydroxy, $C_{3-6}$ cycloalkyl, and $C_{1-3}$ alkoxy), or $C_{3-6}$ cycloalkyl (which may be substituted with 1-3 substituents selected independently from the group consisting of fluorine, hydroxy, $C_{1-3}$ alkyl, and $C_{1-3}$ alkoxy), $R^2$ is fluorine, $C_{1-6}$ alkyl (which may be substituted with 1-3 substituents selected independently from the group consisting of fluorine, hydroxy, $C_{3-6}$ cycloalkyl, and $C_{1-3}$ alkoxy), or $C_{3-6}$ cycloalkyl (which may be substituted with 1-3 substituents selected independently from the group consisting of fluorine, hydroxy, $C_{1-3}$ alkyl, and $C_{1-3}$ alkoxy), or $R^1$ and $R^2$ are taken together with the carbon atom to which they are attached to form $C_{3-6}$ cycloalkyl which may be substituted with 1-3 substituents selected independently from the group consisting of fluorine, hydroxy, $C_{1-3}$ alkyl, and $C_{1-3}$ alkoxy.

In a more preferred embodiment of $R^1$ and $R^2$, $R^1$ is hydrogen, fluorine, or $C_{1-6}$ alkyl which may be substituted with 1-3 substituents selected independently from the group consisting of fluorine, hydroxy, and $C_{1-3}$ alkoxy, $R^2$ is fluorine, or $C_{1-6}$ alkyl which may be substituted with 1-3 substituents selected independently from the group consisting of fluorine, hydroxy, and $C_{1-3}$ alkoxy, or $R^1$ and $R^2$ are taken together with the carbon atom to which they are attached to form $C_{3-6}$ cycloalkyl which may be substituted with 1-3 substituents selected independently from the group consisting of fluorine, hydroxy, $C_{1-3}$ alkyl, and $C_{1-3}$ alkoxy.

In an even more preferred embodiment of $R^1$ and $R^2$, $R^1$ is hydrogen, or $C_{1-6}$ alkyl which may be substituted with 1-3 substituents selected independently from the group consisting of fluorine, hydroxy, and $C_{1-3}$ alkoxy, $R^2$ is $C_{1-6}$ alkyl which may be substituted with 1-3 substituents selected independently from the group consisting of fluorine, hydroxy, and $C_{1-3}$ alkoxy, or $R^1$ and $R^2$ are taken together with the carbon atom to which they are attached to form $C_{3-6}$ cycloalkyl which may be substituted with 1-3 substituents selected independently from the group consisting of fluorine, hydroxy, $C_{1-3}$ alkyl, and $C_{1-3}$ alkoxy.

The $C_{3-6}$ cycloalkyl formed by taking $R^1$ and $R^2$ together with the carbon atom to which they are attached includes, for example, the following (2a)-(2d), and preferably (2a) or (2b), more preferably (2a).

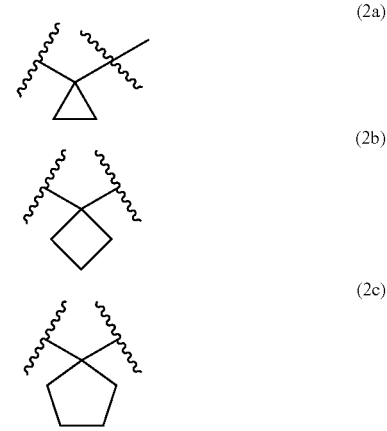

(2d)

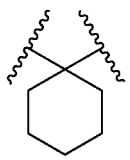

In a preferred embodiment, $R^3$, $R^4$, $R^5$, and $R^6$ are the same or different and are hydrogen, halogen (preferably fluorine, chlorine, or bromine), cyano, nitro, $C_{1-6}$ alkyl (which may be substituted with 1-3 substituents selected independently from the group consisting of fluorine, hydroxy, $C_{3-6}$ cycloalkyl, and $C_{1-3}$ alkoxy), $C_{3-6}$ cycloalkyl (which may be substituted with 1-3 substituents selected independently from the group consisting of fluorine, hydroxy, $C_{1-3}$ alkyl, and $C_{1-3}$ alkoxy), or $C_{1-6}$ alkoxy (which may be substituted with 1-3 substituents selected independently from the group consisting of fluorine, hydroxy, $C_{3-6}$ cycloalkyl, and $C_{1-3}$ alkoxy).

In a more preferred embodiment, $R^3$, $R^4$, $R^5$, and $R^6$ are the same or different and are hydrogen, halogen (preferably fluorine or chlorine), or $C_{1-3}$ alkoxy (which may be substituted with 1-3 fluorine).

In a preferred embodiment of $R^{1A}$ and $R^{2A}$, $R^{1A}$ is hydrogen, fluorine, or $C_{1-6}$ alkyl (which may be substituted with 1-3 substituents selected independently from the group consisting of fluorine, hydroxy, and $C_{1-3}$ alkoxy), and $R^{2A}$ is fluorine or $C_{1-6}$ alkyl (which may be substituted with 1-3 substituents selected independently from the group consisting of fluorine, hydroxy, and $C_{1-3}$ alkoxy), provided that $R^{1A}$ and $R^{2A}$ are different.

In a more preferred embodiment of $R^{1A}$ and $R^{2A}$, $R^{1A}$ is hydrogen or $C_{1-6}$ alkyl (which may be substituted with 1-3 substituents selected independently from the group consisting of fluorine, hydroxy, and $C_{1-3}$ alkoxy), and $R^{2A}$ is $C_{1-6}$ alkyl (which may be substituted with 1-3 substituents selected independently from the group consisting of fluorine, hydroxy, and $C_{1-3}$ alkoxy), provided that $R^{1A}$ and $R^{2A}$ are different.

In an even more preferred embodiment of $R^{1A}$ and $R^{2A}$, $R^{1A}$ is hydrogen, and $R^{2A}$ is methyl.

In a preferred embodiment, $R^7$ is 2-(methoxycarbonyl)ethyl, mesitylenecarbonyloxymethyl, 2-benzothiazolyl (the benzene ring of which may be substituted with 1-3 substituents selected independently from the group consisting of halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), and $C_{1-6}$ alkoxy (which may be substituted with 1-3 substituents selected independently from the group consisting of halogen, hydroxy, $C_{3-6}$ cycloalkyl, and $C_{1-3}$ alkoxy)), 2-pyridyl, 2-pyrimidinyl, or 2-(trimethylsilyl)ethyl.

In a more preferred embodiment, $R^7$ is 2-benzothiazolyl (the benzene ring of which may be substituted with 1-3 substituents selected independently from the group consisting of halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), and $C_{1-6}$ alkoxy (which may be substituted with 1-3 substituents selected independently from the group consisting of halogen, hydroxy, $C_{3-6}$ cycloalkyl, and $C_{1-3}$ alkoxy)), 2-pyrimidinyl, or 2-(trimethylsilyl)ethyl.

In an even more preferred embodiment, $R^7$ is 2-benzothiazolyl.

In a preferred embodiment, $R^6$ is $C_{1-6}$ alkyl, and more preferably methyl.

In a preferred embodiment, $X^{1A}$ is halogen, more preferably chlorine or bromine, and even more preferably chlorine.

In a preferred embodiment of $P^{1A}$ and $P^{2A}$, $P^{1A}$ is 2-indanol-1-yl, 2-phenylethan-1-ol-2-yl, or 3-methylbutan-1-ol-2-yl, and $P^{2A}$ is hydrogen, 2,4-dimethoxybenzyl, or p-methoxybenzyl.

In a more preferred embodiment of $P^{1A}$ and $P^{2A}$, $P^{1A}$ is 2-indanol-1-yl or 2-phenylethan-1-ol-2-yl, and $P^{2A}$ is hydrogen.

In an even more preferred embodiment of $P^{1A}$ and $P^{2A}$, $P^{1A}$ is 2-indanol-1-yl, and $P^{2A}$ is hydrogen.

In a preferred embodiment, $P^{1B}$ and $P^{2B}$ are the same or different and are hydrogen, tert-butoxycarbonyl, benzyloxycarbonyl (the phenyl part of which may be substituted with 1-5 $C_{1-6}$ alkoxy), or benzyl (the phenyl part of which may be substituted with 1-5 $C_{1-6}$ alkoxy).

In a more preferred embodiment, $P^{1B}$ and $P^{2B}$ are the same or different and are hydrogen, 2,4-dimethoxybenzyl, or p-methoxybenzyl.

In a preferred embodiment, the hydrolase is lipase, esterase, amidase, or protease.

In a more preferred embodiment, the hydrolase is lipase.

In a preferred embodiment, the reductase is carbonyl reductase or alcohol dehydrogenase, and more preferably carbonyl reductase.

In a preferred embodiment, the coenzyme is NADH or NADPH, and more preferably NADPH.

In a preferred embodiment of the acid or base used in the hydrolysis, the acid is hydrochloric acid, sulfuric acid, or trifluoroacetic acid, and the base is sodium hydroxide, potassium hydroxide, or lithium hydroxide.

In a preferred embodiment, the reducing agent is sodium borohydride, lithium boron hydride, or lithium aluminum hydride.

In a preferred embodiment, the nitrogen-protecting group is tert-butoxycarbonyl, benzyloxycarbonyl whose phenyl part may be optionally substituted with 1-5 $C_{1-6}$ alkoxy, or benzyl whose phenyl part may be optionally substituted with 1-5 $C_{1-6}$ alkoxy, and more preferably 2,4-dimethoxybenzyl or p-methoxybenzyl.

Preferred compounds of formula (1) include the following compounds or a pharmaceutically acceptable salt thereof.

In an embodiment, the present compound of formula (1) includes the following (A).

(A)

A Compound or pharmaceutically acceptable salt thereof, wherein $R^1$ is hydrogen or halogen, $R^2$ is halogen or $C_{1-6}$ alkyl which may be substituted with 1-3 substituents selected independently from the group consisting of halogen, hydroxy, $C_{3-6}$ cycloalkyl, and $C_{1-3}$ alkoxy, and $R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, hydroxy, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy).

An embodiment of the present compound of formula (1) includes the following (B):

(B)

A Compound or pharmaceutically acceptable salt thereof, wherein $R^1$ and $R^2$ are $C_{1-6}$ alkyl which may be substituted with 1-3 substituents selected independently from the group consisting of halogen, hydroxy, $C_{3-6}$ cycloalkyl, and $C_{1-3}$ alkoxy, and $R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, hydroxy, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy).

An embodiment of the present compound of formula (1) includes the following (C):

(C)

A Compound or pharmaceutically acceptable salt thereof, wherein $R^1$ and $R^2$ are taken together with the carbon atom to which they are attached to form $C_{3-6}$ cycloalkyl which may be substituted with 1-3 substituents selected independently from the group consisting of halogen, hydroxy, $C_{1-3}$ alkyl, and $C_{1-3}$ alkoxy, and $R^3$, $R^4$, $R^5$, and $R^6$ are the same or different and are hydrogen, halogen, cyano, nitro, $C_{1-6}$ alkyl (which may be substituted with 1-3 substituents selected independently from the group consisting of halogen, hydroxy, $C_{3-6}$ cycloalkyl, and $C_{1-3}$ alkoxy), $C_{3-6}$ cycloalkyl (which may be substituted with 1-3 substituents selected independently from the group consisting of halogen, hydroxy, $C_{1-3}$ alkyl, and $C_{1-3}$ alkoxy), or $C_{1-6}$ alkoxy (which may be substituted with 1-3 substituents selected independently from the group consisting of halogen, hydroxy, $C_{3-6}$ cycloalkyl, and $C_{1-3}$ alkoxy).

An embodiment of the present compound of formula (1) includes the following (D):

(D)

A Compound or pharmaceutically acceptable salt thereof, wherein $R^1$ is hydrogen, fluorine, or $C_{1-6}$ alkyl which may be substituted with 1-3 substituents selected independently from the group consisting of fluorine, hydroxy, and $C_{1-3}$ alkoxy, $R^2$ is fluorine or $C_{1-6}$ alkyl which may be substituted with 1-3 substituents selected independently from the group consisting of fluorine, hydroxy, and $C_{1-3}$ alkoxy, or $R^1$ and $R^2$ are taken together with the carbon atom to which they are attached to form $C_{3-6}$ cycloalkyl which may be substituted with 1-3 substituents selected independently from the group consisting of fluorine, hydroxy, $C_{1-3}$ alkyl, and $C_{1-3}$ alkoxy, and $R^3$, $R^4$, $R^5$, and $R^6$ are the same or different and are hydrogen, halogen (preferably fluorine or chlorine), or $C_{1-3}$ alkoxy (which may be substituted with 1-3 fluorine).

An embodiment of the present compound of formula (1) includes the following (E):

(E)

A Compound or pharmaceutically acceptable salt thereof, wherein $R^1$ is hydrogen or $C_{1-6}$ alkyl which may be substituted with 1-3 substituents selected independently from the group consisting of fluorine, hydroxy, and $C_{1-3}$ alkoxy, $R^2$ is $C_{1-6}$ alkyl which may be substituted with 1-3 substituents selected independently from the group consisting of fluorine, hydroxy, and $C_{1-3}$ alkoxy, or $R^1$ and $R^2$ are taken together with the carbon atom to which they are attached to form $C_{3-6}$ cycloalkyl which may be substituted with 1-3 substituents selected independently from the group consisting of fluorine, hydroxy, $C_{1-3}$ alkyl, and $C_{1-3}$ alkoxy, and $R^3$, $R^4$, $R^5$, and $R^6$ are the same or different and are hydrogen, halogen (preferably fluorine or chlorine), or $C_{1-6}$ alkoxy (which may be substituted with 1-3 fluorine).

An embodiment of the present compound of formula (1) includes the following compounds:

1-(1,2-benzoxazol-3-yl)ethane-1-sulfonamide (Example 1),
2-(1,2-benzoxazol-3-yl)propane-2-sulfonamide (Example 2),
1-(1,2-benzoxazol-3-yl)-1-fluoromethane-sulfonamide (Example 3),
1-(1,2-benzoxazol-3-yl)-1,1-difluoromethane-sulfonamide (Example 4),
1-(1,2-benzoxazol-3-yl)cyclopropane-1-sulfonamide (Example 5),
1-(1,2-benzoxazol-3-yl)propane-1-sulfonamide (Example 6),
1-(1,2-benzoxazol-3-yl)butane-1-sulfonamide (Example 7),
1-(1,2-benzoxazol-3-yl)-1-fluoroethane-1-sulfonamide (Example 8),
1-(1,2-benzoxazol-3-yl)-2-methylpropane-1-sulfonamide (Example 9),
1-(5-methoxy-1,2-benzoxazol-3-yl)ethane-1-sulfonamide (Example 10),
1-(5-fluoro-1,2-benzoxazol-3-yl)ethane-1-sulfonamide (Example 11),
1-(5-chloro-1,2-benzoxazol-3-yl)ethane-1-sulfonamide (Example 12),
(1R)-1-(1,2-benzoxazol-3-yl)ethane-1-sulfonamide (Example 13), and
(1S)-1-(1,2-benzoxazol-3-yl)ethane-1-sulfonamide (Example 14).

An embodiment of the present compound of formula (1) includes the following compounds:

1-(1,2-benzoxazol-3-yl)ethane-1-sulfonamide (Example 1),
2-(1,2-benzoxazol-3-yl)propane-2-sulfonamide (Example 2),
1-(1,2-benzoxazol-3-yl)-1-fluoromethane-sulfonamide (Example 3),
1-(1,2-benzoxazol-3-yl)-1,1-difluoromethane-sulfonamide (Example 4),
1-(1,2-benzoxazol-3-yl)cyclopropane-1-sulfonamide (Example 5),
1-(1,2-benzoxazol-3-yl)-1-fluoroethane-1-sulfonamide (Example 8),
(1R)-1-(1,2-benzoxazol-3-yl)ethane-1-sulfonamide (Example 13), and
(1S)-1-(1,2-benzoxazol-3-yl)ethane-1-sulfonamide (Example 14).

An embodiment of the present compound of formula (1) includes the following compounds:

1-(1,2-benzoxazol-3-yl)ethane-1-sulfonamide (Example 1),
2-(1,2-benzoxazol-3-yl)propane-2-sulfonamide (Example 2),
1-(1,2-benzoxazol-3-yl)cyclopropane-1-sulfonamide (Example 5), (1R)-1-(1,2-benzoxazol-3-yl)ethane-1-sulfonamide (Example 13), and
(1S)-1-(1,2-benzoxazol-3-yl)ethane-1-sulfonamide (Example 14).

An embodiment of the present compound of formula (1) includes the following compounds:
1-(1,2-benzoxazol-3-yl)ethane-1-sulfonamide (Example 1),
(1R)-1-(1,2-benzoxazol-3-yl)ethane-1-sulfonamide (Example 13), and
(1S)-1-(1,2-benzoxazol-3-yl)ethane-1-sulfonamide (Example 14).

The compound of formula (I) has some polymorphism. In general, it is known that a crystalline substance can be analyzed by conventional technique such as X-ray powder diffraction (hereinafter, "XRPD") analysis, differential scanning calorimetry (hereinafter, "DSC"), thermogravimetric analysis (hereinafter, "TGA"), dynamic vapor adsorption (hereinafter, "DVS"), diffuse reflectance infrared Fourier transform (DRIFT) spectroscopy, near-infrared reflectance (NIR) spectroscopy, and liquid-phase and/or solid-phase nuclear magnetic resonance spectroscopy. And, the water content of a crystalline substance can be measured by Karl Fischer titration.

For example, the compound of Example 13 has polymorphism, and three crystalline forms (form I, form II, and form III) are identified herein, but the crystalline forms of the present invention should not limited thereto.

Another embodiment of the present invention includes (1R)-1-(1,2-benzoxazol-3-yl)ethane-1-sulfonamide in crystalline form of form I.

Another embodiment of the present invention includes (1R)-1-(1,2-benzoxazol-3-yl)ethane-1-sulfonamide in crystalline form characterized by a powder x-ray diffraction pattern having at least one characteristic peak of 5.7°±0.2° as 2θ° (form I).

Another embodiment of the present invention includes (1R)-1-(1,2-benzoxazol-3-yl)ethane-1-sulfonamide in crystalline form characterized by a powder x-ray diffraction pattern having at least one characteristic peak of 17.3°±0.2° as 2θ° (form I).

Another embodiment of the present invention includes (1R)-1-(1,2-benzoxazol-3-yl)ethane-1-sulfonamide in crystalline form characterized by a powder x-ray diffraction pattern having at least two characteristic peaks of 5.7°±0.2° and 17.3°±0.2° as 2θ° (form I).

Another embodiment of the present invention includes (1R)-1-(1,2-benzoxazol-3-yl)ethane-1-sulfonamide in crystalline form of form I which is characterized by a powder x-ray diffraction pattern having characteristic peaks of 5.7°±0.2°, 14.1°±0.2°, 17.3°±0.2°, 19.1°±0.2°, 19.3°±0.2°, 21.6°±0.2°, 22.5°±0.2°, 23.1°±0.2°, 23.3°±0.2°, and 26.5°±0.2° as 2θ°. The crystal can be identified with 4 or 5 peaks among these 10 peaks.

Figures 1, 2:
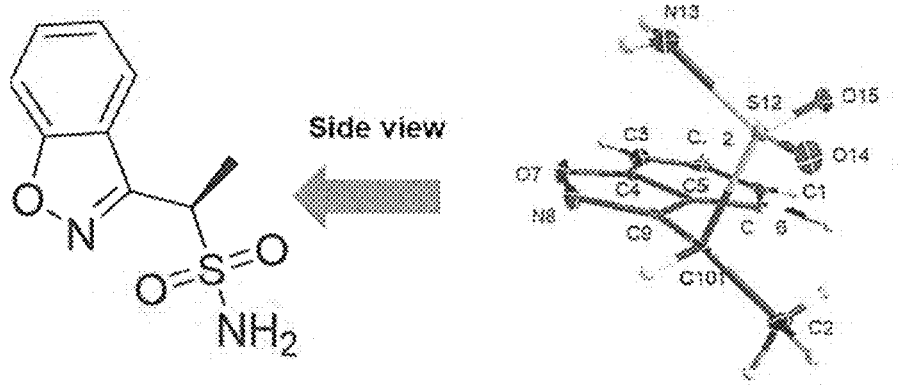
Figure 2:
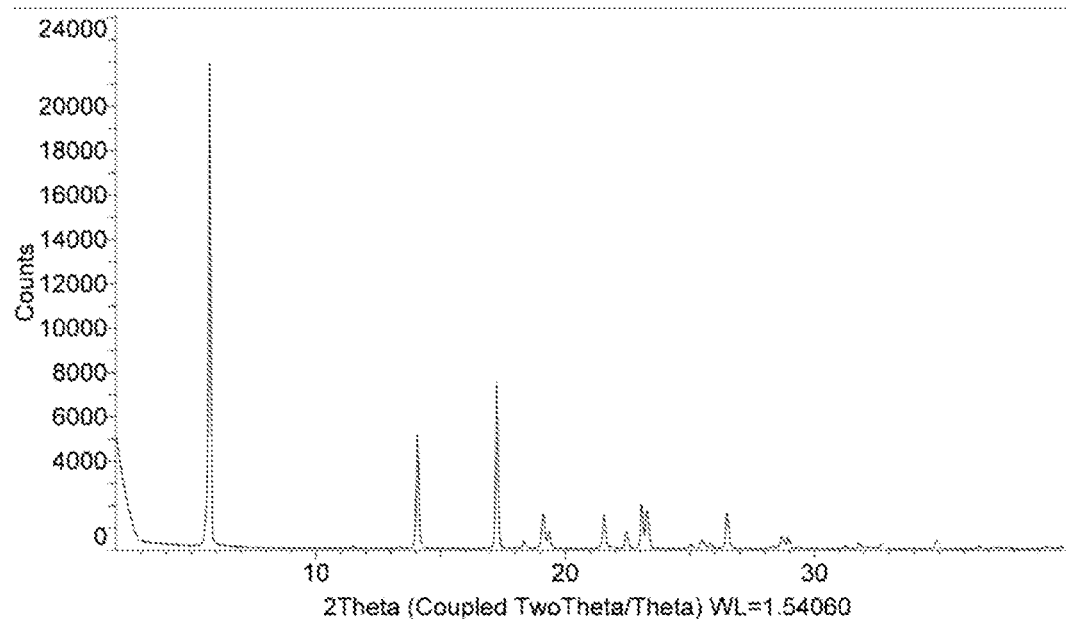

Another embodiment of the present invention includes (1R)-1-(1,2-benzoxazol-3-yl)ethane-1-sulfonamide in a crystalline form whose X-ray powder diffraction pattern is substantially identical to the X-ray powder diffraction pattern shown in FIG. 2 (form I).

Another embodiment of the present invention includes (1R)-1-(1,2-benzoxazol-3-yl)ethane-1-sulfonamide in a crystalline form that has an endothermic peak associated with melting in differential scanning calorimetry (DSC), in which the extrapolated onset temperature (Tim) is 144.0° C.±5° C. (form I).

Figure 5:
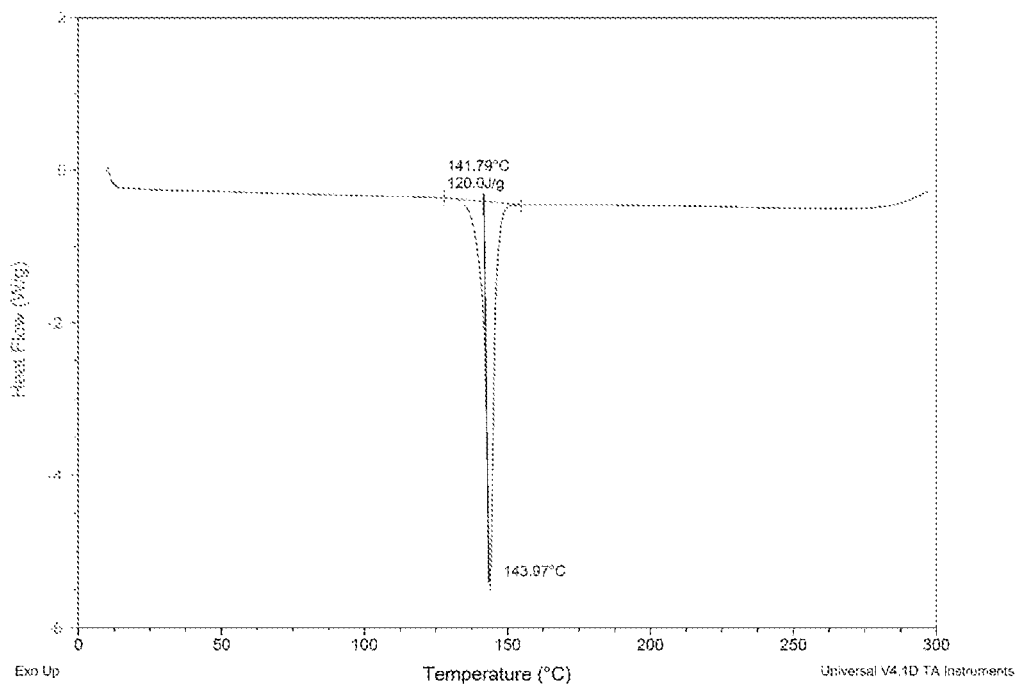
FIG. 5 shows differential scanning calorimetry (DSC) of Example 13 (form I), which was obtained in Example 24. The x-axis indicates temperature (° C.), and the y-axis indicates heat flow (watt/g).

Another embodiment of the present invention includes (1R)-1-(1,2-benzoxazol-3-yl)ethane-1-sulfonamide in a crystalline form whose DSC thermogram is substantially identical to the DSC thermogram shown in FIG. 5 (form I).

Figure 8:
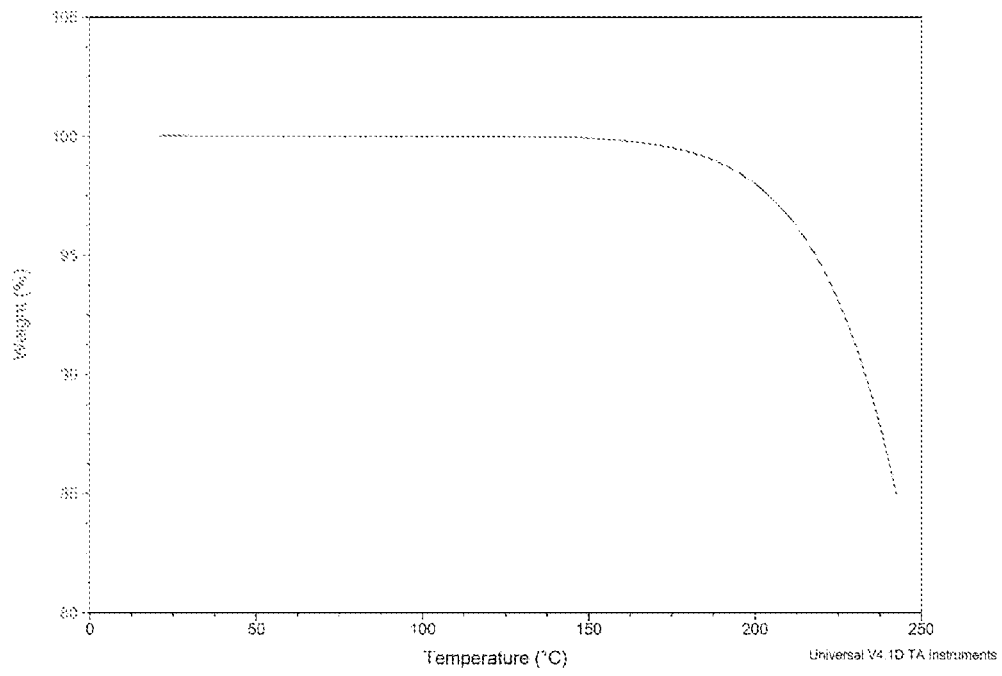
FIG. 8 shows thermogravimetric analysis (TGA) of Example 13 (form I), which was obtained in Example 25. The x-axis indicates temperature (° C.), and the y-axis indicates weight variation (%).

Another embodiment of the present invention includes (1R)-1-(1,2-benzoxazol-3-yl)ethane-1-sulfonamide in a crystalline form whose TGA graph is substantially identical to the TGA graph shown in FIG. 8 (form I).

Figure 11:
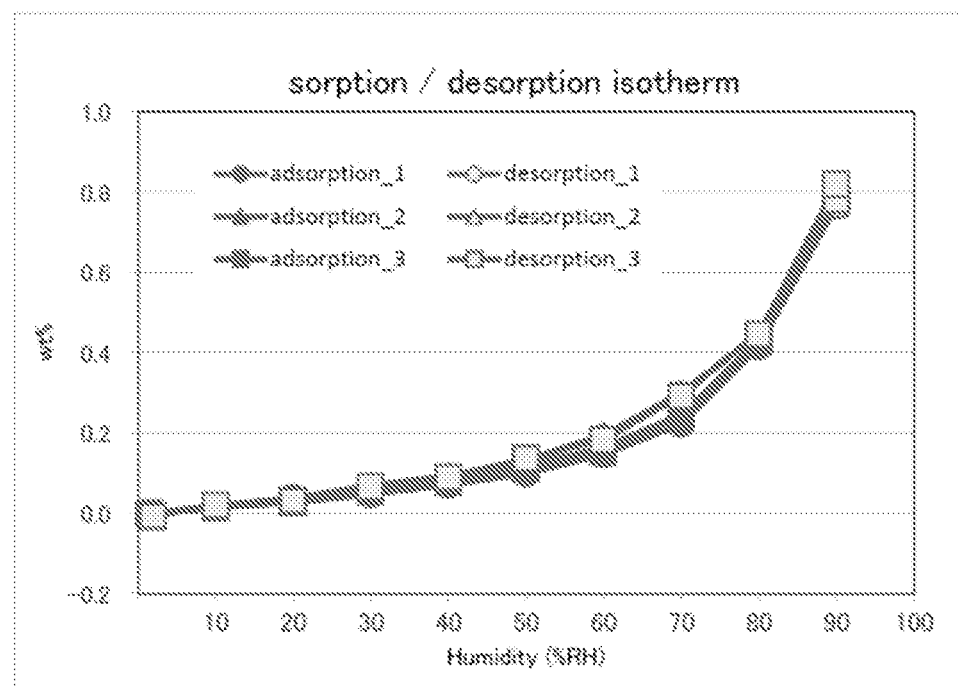
FIG. 11 shows dynamic vapor adsorption (DVS) of Example 13 (form I), which was obtained in Example 26. The x-axis indicates relative humidity (%), and the y-axis indicates weight variation (%).

Another embodiment of the present invention includes (1R)-1-(1,2-benzoxazol-3-yl)ethane-1-sulfonamide in a crystalline form whose DVS graph is substantially identical to the DVS graph shown in FIG. 11 (form I).

Crystalline Example 13 of form I can be prepared by concentrating a solution of Example 13 in acetonitrile, or shaking an aqueous suspension of a mixture of forms I and II of Example 13 at 25° C. for 9-11 days.

Another embodiment of the present invention includes (1R)-1-(1,2-benzoxazol-3-yl)ethane-1-sulfonamide in crystalline form of form II.

Another embodiment of the present invention includes (1R)-1-(1,2-benzoxazol-3-yl)ethane-1-sulfonamide in a crystalline form characterized by a powder x-ray diffraction pattern having at least one characteristic peak of 17.6°±0.2° as 2θ° (form II).

Another embodiment of the present invention includes (1R)-1-(1,2-benzoxazol-3-yl)ethane-1-sulfonamide in a crystalline form characterized by a powder x-ray diffraction pattern having at least one characteristic peak of 8.7°±0.2° as 2θ° (form II).

Another embodiment of the present invention includes (1R)-1-(1,2-benzoxazol-3-yl)ethane-1-sulfonamide in a crystalline form characterized by a powder x-ray diffraction pattern having at least two characteristic peaks of 8.7°±0.2° and 17.6°±0.2° as 2θ° (form II).

Another embodiment of the present invention includes (1R)-1-(1,2-benzoxazol-3-yl)ethane-1-sulfonamide in crystalline form of form II which is characterized by a powder x-ray diffraction pattern having characteristic peaks of 8.7°±0.2°, 13.5°±0.2°, 15.5°±0.2°, 17.6°±0.2°, 20.3°±0.2°, 21.6°±0.2°, 22.6°±0.2°, 26.2°±0.2°, 26.8°±0.2°, and 35.2°±0.2° as 2θ. The crystal can be identified with 4 or 5 peaks among these 10 peaks.

Figure 3:
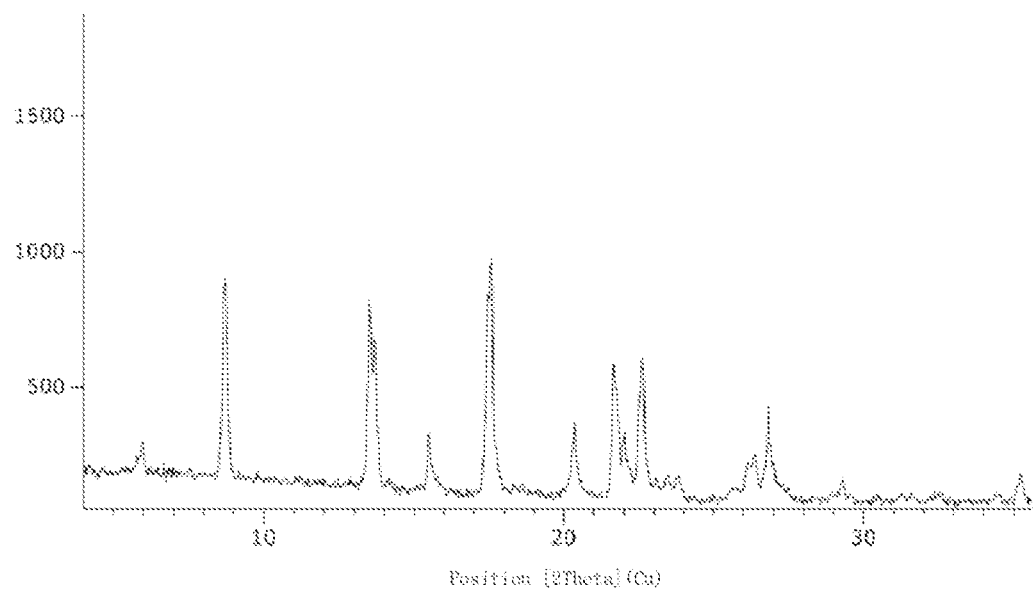
FIG. 3 shows X-ray powder diffraction pattern of Example 13 (form II), which was obtained in Example 23. The x-axis indicates 2θ value, and the y-axis indicates intensity.

Another embodiment of the present invention includes (1R)-1-(1,2-benzoxazol-3-yl)ethane-1-sulfonamide in a crystalline form whose X-ray powder diffraction pattern is substantially identical to the X-ray powder diffraction pattern shown in FIG. 3 (form II).

Another embodiment of the present invention includes (1R)-1-(1,2-benzoxazol-3-yl)ethane-1-sulfonamide in a crystalline form that has an endothermic peak associated with melting in differential scanning calorimetry (DSC), in which the extrapolated onset temperature (Tim) is 143.8° C.±5° C. (form II).

Figure 6:
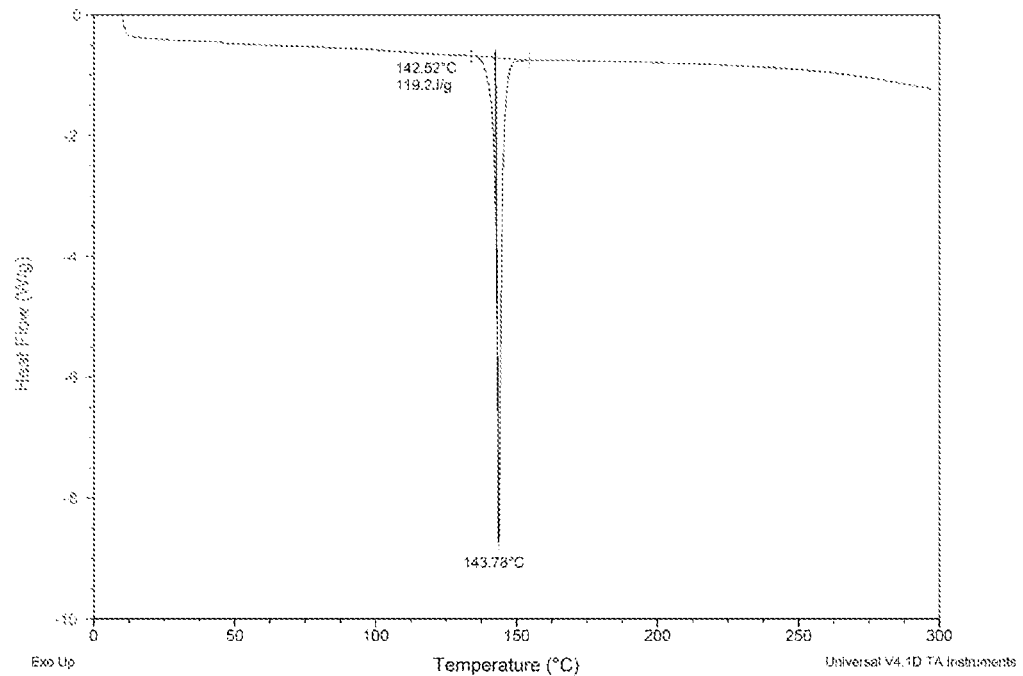
FIG. 6 shows differential scanning calorimetry (DSC) of Example 13 (form II), which was obtained in Example 24. The x-axis indicates temperature (° C.), and the y-axis indicates heat flow (watt/g).

Another embodiment of the present invention includes (1R)-1-(1,2-benzoxazol-3-yl)ethane-1-sulfonamide in a crystalline form whose DSC thermogram is substantially identical to the DSC thermogram shown in FIG. 6 (form II).

Figure 9:
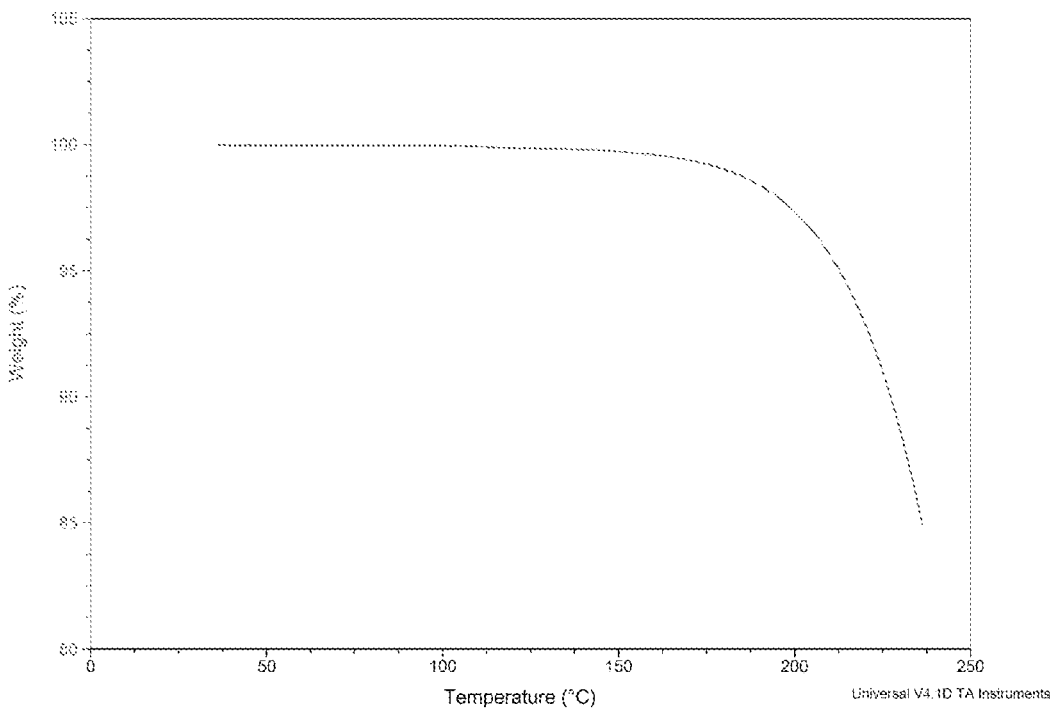
FIG. 9 shows thermogravimetric analysis (TGA) of Example 13 (form II), which was obtained in Example 25. The x-axis indicates temperature (° C.), and the y-axis indicates weight variation (%).

Another embodiment of the present invention includes (1R)-1-(1,2-benzoxazol-3-yl)ethane-1-sulfonamide in a crystalline form whose TGA graph is substantially identical to the TGA graph shown in FIG. 9 (form II).

Figure 12:
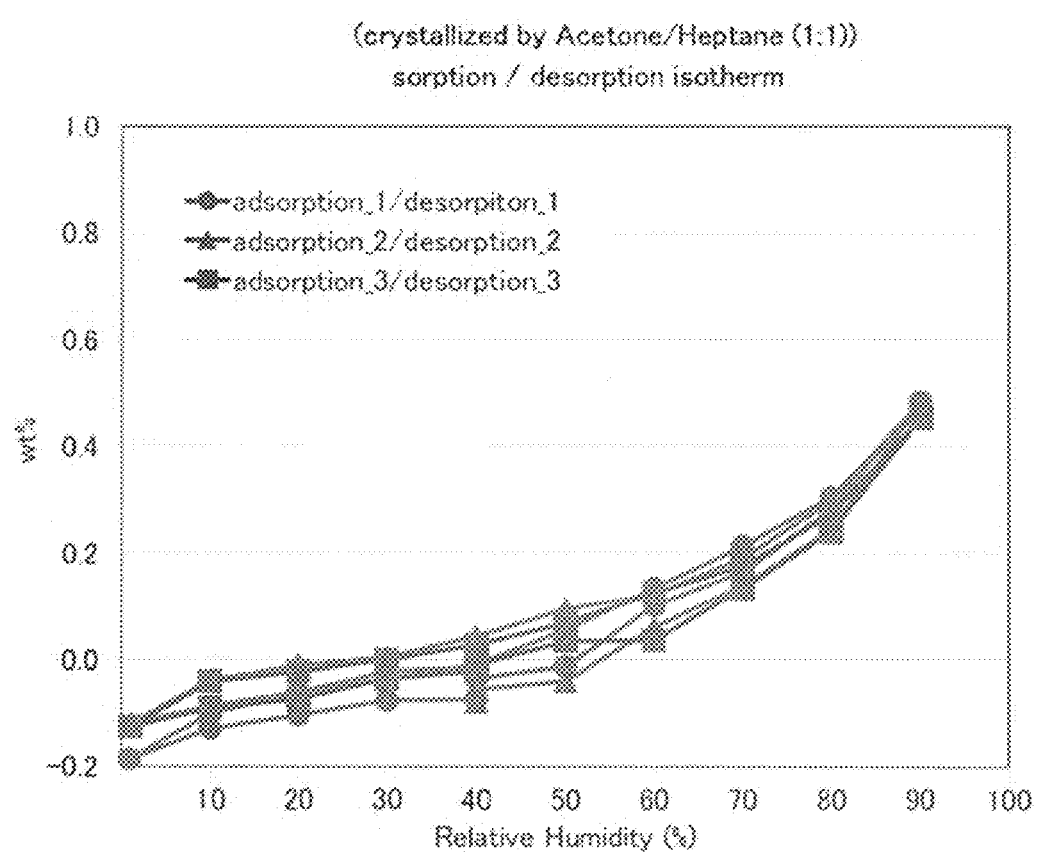
FIG. 12 shows dynamic vapor adsorption (DVS) of Example 13 (form II), which was obtained in Example 26. The x-axis indicates relative humidity (%), and the y-axis indicates weight variation (%).

Another embodiment of the present invention includes (1R)-1-(1,2-benzoxazol-3-yl)ethane-1-sulfonamide in a crystalline form whose DVS graph is substantially identical to the DVS graph shown in FIG. 12 (form II).

Crystalline Example 13 of form II can be prepared by heating a solution of Example 13 in acetonitrile/water mixture (1:1) or acetone/heptane mixture (1:1) at about 80° C. for about one hour, and leaving the solution to stand at room temperature for a day.

Another embodiment of the present invention includes (1R)-1-(1,2-benzoxazol-3-yl)ethane-1-sulfonamide in crystalline form of form III.

Another embodiment of the present invention includes (1R)-1-(1,2-benzoxazol-3-yl)ethane-1-sulfonamide in a crystalline form characterized by a powder x-ray diffraction pattern having at least one characteristic peak of 11.1°±0.2° as 2θ° (form III).

Another embodiment of the present invention includes (1R)-1-(1,2-benzoxazol-3-yl)ethane-1-sulfonamide in a crystalline form characterized by a powder x-ray diffraction pattern having at least one characteristic peak of 20.3°±0.2° as 2θ° (form III).

Another embodiment of the present invention includes (1R)-1-(1,2-benzoxazol-3-yl)ethane-1-sulfonamide in a crystalline form characterized by a powder x-ray diffraction pattern having at least two characteristic peaks of 11.1°±0.2° and 20.3°±0.2° as 2θ° (form III).

Another embodiment of the present invention includes (1R)-1-(1,2-benzoxazol-3-yl)ethane-1-sulfonamide in crystalline form of form III which is characterized by a powder x-ray diffraction pattern having characteristic peaks of 11.1°±0.2°, 13.8°±0.2°, 17.0°±0.2°, 20.3°±0.2°, 21.4°±0.2°, 22.1°±0.2°, 22.4°±0.2°, 24.8°±0.2°, 26.3°±0.2°, and 27.9°±0.2° as 2θ. The crystal can be identified with 4 or 5 peaks among these 10 peaks.

Figure 4:
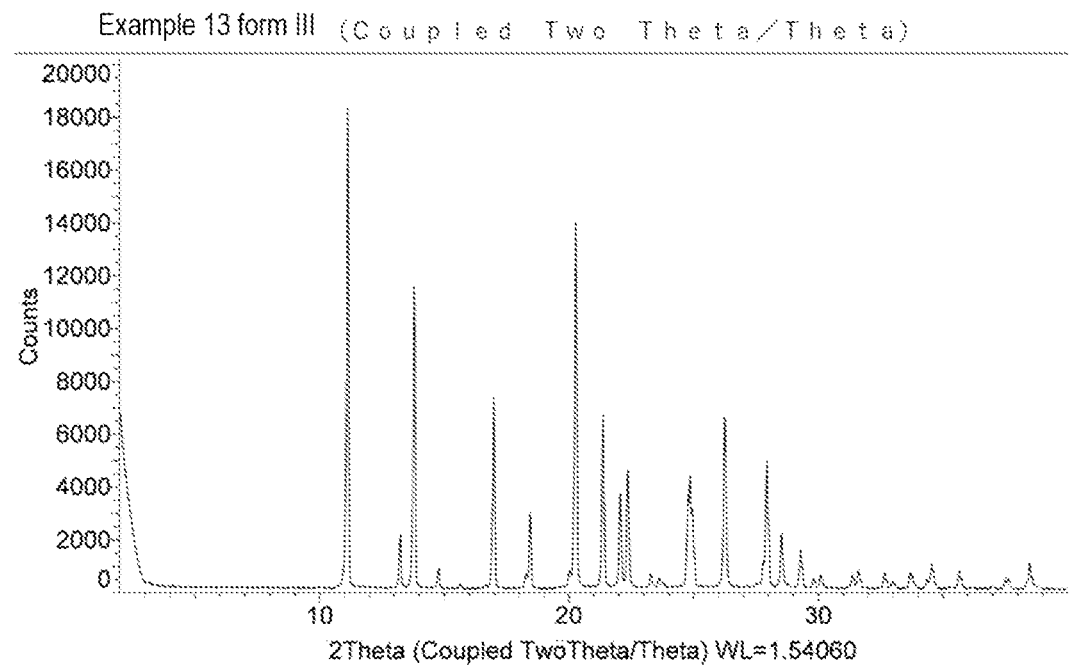
FIG. 4 shows X-ray powder diffraction pattern of Example 13 (form III), which was obtained in Example 23. The x-axis indicates 2θ value, and the y-axis indicates intensity.

Another embodiment of the present invention includes (1R)-1-(1,2-benzoxazol-3-yl)ethane-1-sulfonamide in a crystalline form whose X-ray powder diffraction pattern is substantially identical to the X-ray powder diffraction pattern shown in FIG. 4 (form III).

Another embodiment of the present invention includes (1R)-1-(1,2-benzoxazol-3-yl)ethane-1-sulfonamide in a crystalline form that has an endothermic peak associated with melting in differential scanning calorimetry (DSC), in which the extrapolated onset temperature (Tim) is 142.5° C.±5° C. (form III).

Figure 7:
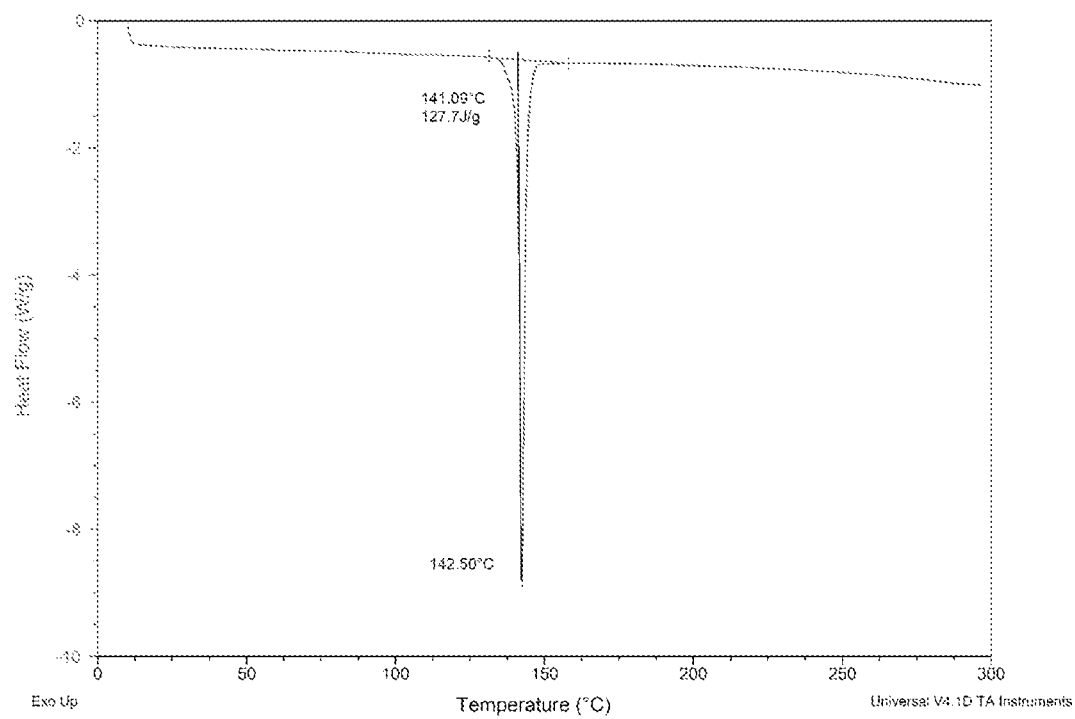
FIG. 7 shows differential scanning calorimetry (DSC) of Example 13 (form III), which was obtained in Example 24. The x-axis indicates temperature (° C.), and the y-axis indicates heat flow (watt/g).

Another embodiment of the present invention includes (1R)-1-(1,2-benzoxazol-3-yl)ethane-1-sulfonamide in a crystalline form whose DSC thermogram is substantially identical to the DSC thermogram shown in FIG. 7 (form III).

Figure 10:
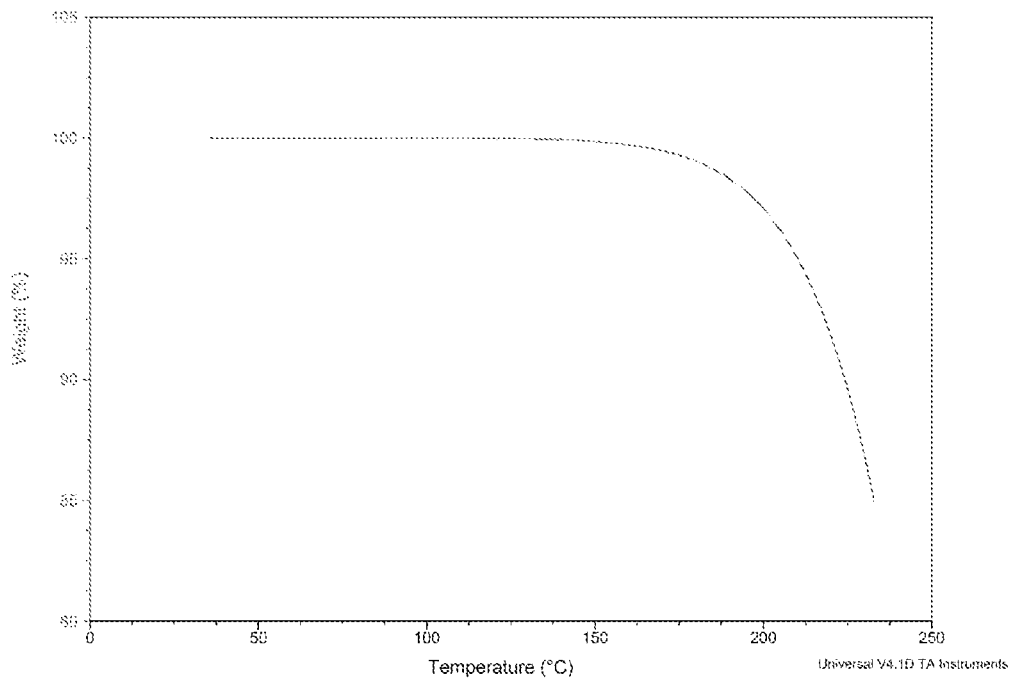
FIG. 10 shows thermogravimetric analysis (TGA) of Example 13 (form III), which was obtained in Example 25. The x-axis indicates temperature (° C.), and the y-axis indicates weight variation (%).

Another embodiment of the present invention includes (1R)-1-(1,2-benzoxazol-3-yl)ethane-1-sulfonamide in a crystalline form whose TGA graph is substantially identical to the TGA graph shown in FIG. 10 (form III).

Figure 13:
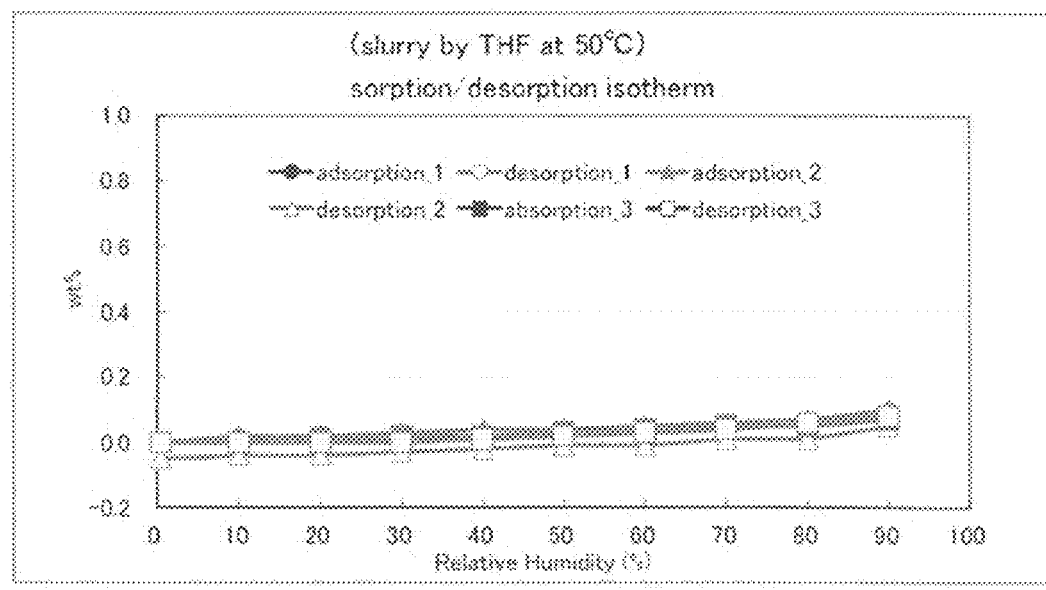
FIG. 13 shows dynamic vapor adsorption (DVS) of Example 13 (form III), which was obtained in Example 26. The x-axis indicates relative humidity (%), and the y-axis indicates weight variation (%).

Another embodiment of the present invention includes (1R)-1-(1,2-benzoxazol-3-yl)ethane-1-sulfonamide in a crystalline form whose DVS graph is substantially identical to the DVS graph shown in FIG. 13 (form III).

Crystalline Example 13 of form III can be prepared by shaking a suspension of Example 13 in an organic solvent (e.g. ethanol, chloroform, acetonitrile, tetrahydrofuran, ethyl acetate, acetone, and tetrahydrofuran/heptane mixture (1:1)) at about 50° C. for 9-11 days. Or, it can be prepared by shaking a suspension of Example 13 in an organic solvent (e.g. acetonitrile, ethyl acetate, acetone, acetone/water mixture (1:1), and tetrahydrofuran/heptane mixture (1:1)) at about 25° C. for 9-11 days. Or, it can be prepared by shaking a suspension of a mixture of forms I and II of Example 13 in an organic solvent (e.g. ethanol, 2-propanol, chloroform, acetonitrile, tetrahydrofuran, ethyl acetate, acetone, and tetrahydrofuran/heptane mixture (1:1)) at about 50° C. for 9-11 days. Or, it can be prepared by shaking a suspension of a mixture of forms I and II of Example 13 in an organic solvent (e.g. 2-propanol, chloroform, acetonitrile, tetrahydrofuran, ethyl acetate, acetone, methanol/water mixture (1:1), 2-propanol/water mixture (1:1), acetone/water mixture (1:1), and tetrahydrofuran/heptane mixture (1:1)) at about 25° C. for 9-11 days. Or, it can be prepared by heating a solution of Example 13 in tert-butyl methyl ether at about 80° C. for about one hour, and leaving the solution to stand at room temperature for a day. Example 13 of form III can be prepared in high repeatability by shaking forms I-III in several kinds of solvents for 9-11 days, which is thought to be the most stable form.

The 2θ values in X-ray powder diffraction pattern can slightly vary depending on measuring instruments or prepared samples, and thus the values defined herein are not always absolutely correct (see, Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures). In general, the diffraction angles in X-ray powder diffraction spectrum have a measurement error of, for example, about ±0.2° for 2θ, and thus it is necessary to consider such measurement error. In addition, the intension can also vary depending on the experimental condition or the sample preparation (preferred orientation). The 2θ values and intensions described herein are shown by actual values measured with copper emission (Cu Kα1, λ=1.5406 Å, Kα2, λ=1.5444 Å).

In addition, it is known that X-ray powder diffraction patterns may have one or more measurement errors depending on measuring conditions (e.g. instrument or machine used). For example, crystalline particles whose size is more than 30 micron or whose aspect ratio is not single may affect the relative intensity of the peaks. And, the position of the reflection may be affected by the height where the sample is placed on the diffractometer or the zero-calibration of the diffractometer. The planarity of the sample surface may also slightly affect the diffraction. Thus, unless otherwise described, the above-mentioned crystalline forms of the present invention should not be restricted to the crystals based on the X-ray powder diffraction patterns of FIGS. 2, 3, and 4. The crystals based on the X-ray powder diffraction patterns shown in the figures and also the crystals which have substantially the same X-ray powder diffraction patterns should be both included in the present invention.

And, extrapolated onset temperature (Tim), endothermic peak temperature (Tpm), etc. in differential scanning calorimetry (DSC) have acceptable error of ±5° C. In differential scanning calorimetry (DSC), the extrapolated onset temperature (Tim) means that a temperature derived from the point where the extrapolated line from the upstroke of the endothermic peak curve intersects the extrapolated line of the base line, and endothermic peak temperature (Tpm) means that the peak top temperature of the endothermic peak.

The "pharmaceutically acceptable salt" includes acid addition salts and base addition salts. For example, the acid addition salt includes inorganic acid salts such as hydrochloride, hydrobromide, sulfate, hydroiodide, nitrate, and phosphate; and organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, and camphorsulfonate. The base addition salt includes inorganic base salts such as sodium salts, potassium salts, calcium salts, magnesium salts, barium salts, and aluminum salts; and organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N,N-dibenzylethylamine. The "pharmaceutically acceptable salt" also includes amino acid salts of basic or acidic amino acids such as arginine, lysine, ornithine, aspartate, and glutamate.

The suitable salts of starting materials and intermediates and the acceptable salts of drug substances are conventional non-toxic salts. The suitable salt includes, for example, acid addition salts such as organic acid salts (including acetate, trifluoroacetate, maleate, fumarate, citrate, tartrate, methanesulfonate, benzenesulfonate, formate, and p-toluenesulfonate) and inorganic acid salts (including hydrochloride, hydrobromide, hydroiodide, sulfate, nitrate, and phosphate); salts with amino acids (including arginine, aspartate, and glutamate); alkali metal salts (including sodium salts, and potassium salts); alkaline earth metal salts (including calcium salts, and magnesium salts); ammonium salts; organic base salts (including trimethylamine salts, triethylamine salts, pyridine salts, picolinate, dicyclohexylamine salts, and N,N'-dibenzylethylenediamine salts); and other salts which a person skilled in the art can optionally select.

If the compound of the present invention should be obtained as a salt thereof, when the present compound is obtained as a salt, it may be purified without further reaction, and when it is obtained in a free form, it may be dissolved or suspended in an appropriate organic solvent, and an acid or base may be added therein to form a salt by a common method.

In the present invention, the compound of formula (1) encompasses deuterated compounds in which any one or more $^1$H in the compound of formula (1) are replaced with $^2$H (D).

The present invention encompasses compounds of formula (1) or pharmaceutically acceptable salts thereof. The compound of the present invention may exist in a form of hydrate and/or solvate with various solvents, including ethanolate, and these hydrate and/or solvate are included in the compound of the present invention. In addition, the present invention encompasses all tautomers of the compound (1), all possible stereoisomers thereof, crystalline forms thereof in various states, and mixtures thereof.

The present compound (1) encompasses optical isomers based on an optically active center, atropisomers based on axial or planar chirality caused by restriction of intramolecular rotation, and all other isomers which can exist as stereoisomers, tautomers, and geometric isomers, and racemates, and mixtures thereof.

Especially, each optical isomer and atropisomer can be obtained as a racemate, or as an optically active substance when an optically active starting material or intermediate is used. Racemates of corresponding starting materials, intermediates, or final products can also be physically or chemically resolved into optical enantiomers by a known isolating method such as a method with an optically active column and a fractional crystallization method, at an appropriate step in the above preparation processes, if necessary. These methods for resolving enantiomers include a diastereomer method in which, for example, a racemate is reacted with an optically active resolving agent to synthesize two kinds of diastereomers, which are resolved by fractional crystallization or a similar method through different physical characters.

Preparation Process 1

The compound of formula (I) [the compound of the following formula (Ia)] can be prepared by the following preparation process.

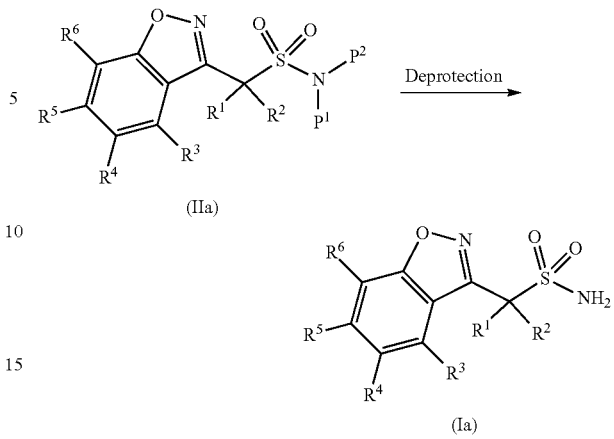

Wherein $R^1$, $R^2$, $R^3$, $R^4$, $R^5$, and $R^6$ are as defined in Item 1; $P^1$ is a protection group for nitrogen atom which can be removed under an acidic condition, including 2,4-dimethoxybenzyl, p-methoxybenzyl, 2-indanol-1-yl, 2-phenylethan-1-ol-2-yl, 3-methylbutan-1-ol-2-yl, and the like; and $P^2$ is hydrogen, or a protection group for nitrogen atom which can be removed under an acidic condition, including 2,4-dimethoxybenzyl, p-methoxybenzyl, 2-indanol-1-yl, 2-phenylethan-1-ol-2-yl, 3-methylbutan-1-ol-2-yl, and the like.

Compound (Ia) can be prepared by deprotecting Compound (IIa).

The deprotection of Compound (IIa) can be done in a conventional manner. For example, the reaction can be accomplished by reacting Compound (IIa) with an organic strong acid such as trifluoroacetic acid, methanesulfonic acid, and trifluoromethanesulfonic acid, or an inorganic strong acid such as hydrochloric acid, sulfuric acid, and nitric acid.

The deprotection of Compound (IIa) is done in a solvent or without a solvent. The solvent should be selected depending on the starting compound, etc., which includes, for example, toluene, THF, dioxane, DME, dichloromethane, chloroform, ethyl acetate, acetone, acetonitrile, DMF, and DMSO. The solvent may be used alone or as a mixture thereof. And, as a protection group for Compound (IIa), t-butoxycarbonyl group, t-butyl group, p-methoxybenzyl group, and the like which can be cleaved under an acid condition may be used instead, besides 2,4-dimethoxybenzyl group. The reaction temperature should be decided depending on the starting compound, etc., which may be generally about −30° C. to about 150° C., preferably about −10° C. to about 70° C. The reaction time may be generally 30 minutes to 24 hours.

Preparation Process 2

Compound (IIa) which is used in the above preparation process can be prepared according to the process in the following scheme.

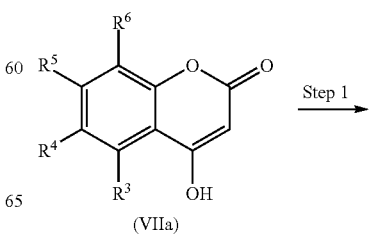

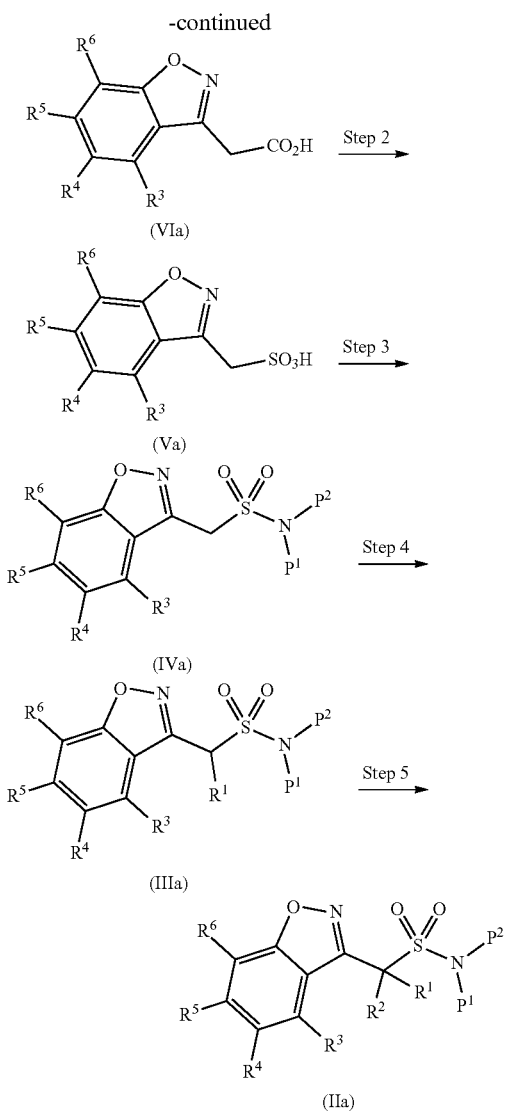

Wherein $R^1$, $R^2$, $R^3$, $R^4$, $R^5$, and $R^6$ are as defined in Item 1; and $P^1$ and $P^2$ are as defined in Preparation process 1.

(Step 1): Compound (VIa) can be prepared by reacting Compound (VIIa) with hydroxylamine.

The reaction of Step 1 can be done in a conventional manner. For example, the reaction can be done by reacting Compound (VIIa) with hydroxylamine in a suitable solvent in the presence or absence of a base. The solvent should be selected depending on the starting compound, etc., which includes, for example, ethers such as $Et_2O$, THF, dioxane, and DME; alcohols such as methanol, ethanol, and isopropyl alcohol; water; and toluene. The solvent may be used alone or as a mixture thereof. And, the base used herein includes, for example, an alkaline metal hydroxide such as sodium hydroxide, potassium hydroxide, and lithium hydroxide; an alkaline metal alkoxide such as potassium t-butoxide; an alkaline metal carbonate such as sodium carbonate, potassium carbonate, and lithium carbonate; and an organic base such as triethylamine, N,N-diisopropylethylamine, pyridine, 2,6-lutidine, 2,4,6-collidine, and 4-dimethylaminopyridine. The reaction temperature should be decided depending on the starting compound or reagent to be used, etc., which may be generally $-100°$ C. to $200°$ C., preferably $0°$ C. to $150°$ C. The reaction time may be generally 30 minutes to 24 hours.

(Step 2): Compound (Va) can be prepared by reacting Compound (VIa) with chlorosulfuric acid.

The reaction of Step 2 can be done in a conventional manner. For example, the reaction can be done by reacting Compound (VIa) with chlorosulfuric acid in a solvent. The solvent should be selected depending on the starting compound, etc., which includes, for example, $Et_2O$, THF, dioxane, DME, and toluene. The solvent may be used alone or as a mixture thereof. The reaction temperature should be decided depending on the starting compound or reagent to be used, etc., which may be generally $-100°$ C. to $200°$ C., preferably $0°$ C. to $150°$ C. The reaction time may be generally 30 minutes to 24 hours.

(Step 3): Compound (IVa) can be prepared by sulfonamidating Compound (Va).

The reaction of Step 3 can be done in a conventional manner. For example, the reaction can be accomplished by transforming Compound (Va) to its sulfonyl chloride form and then reacting the sulfonyl chloride form with amine. The transformation to the sufonyl chloride form can be done by reacting with phosphorus oxychloride in a solvent or without a solvent. The solvent should be selected depending on the starting compound, etc., which includes, for example, $Et_2O$, THF, dioxane, DME, and toluene. The solvent may be used alone or as a mixture thereof. The reaction temperature should be decided depending on the starting compound or reagent to be used, etc., which may be generally $-100°$ C. to $200°$ C., preferably $0°$ C. to $150°$. The reaction time may be generally 30 minutes to 24 hours.

The transforming from the sulfonyl chloride compound which is the intermediate of Step 3 to the sulfonamide compound is done by reacting the sulfonyl chloride compound with $NHP^1P^2$ which is an amine compound mono- or di-substituted with a protection group which can be removed under an acidic condition, in the presence or absence of a base in a solvent. The solvent should be selected depending on the starting compound, etc., which includes, for example, $Et_2O$, THF, dioxane, DME, DMF, acetonitrile, and toluene. The solvent may be used alone or as a mixture thereof. And, the base used herein includes, for example, an alkaline metal hydroxide such as sodium hydroxide, potassium hydroxide, and lithium hydroxide; an alkaline metal alkoxide such as potassium t-butoxide; an alkaline metal carbonate such as sodium carbonate, potassium carbonate, and lithium carbonate; and an organic base such as triethylamine, N,N-diisopropylethylamine, pyridine, 2,6-lutidine, 2,4,6-collidine, and 4-dimethylaminopyridine. The reaction temperature should be decided depending on the starting compound or reagent to be used, etc., which may be generally $-100°$ C. to $200°$ C., preferably $0°$ C. to $150°$ C. The reaction time may be generally 30 minutes to 24 hours.

(Step 4): Compound (IIIa) can be prepared by alkylating or halogenating Compound (IVa). When $R^1$ is hydrogen, the present step is omitted.

The alkylation or halogenation of Step 4 can be done in a conventional manner. For example, the alkylation can be done by reacting Compound (IVa) with an alkyl halide RIX in the presence of a base in a suitable solvent, and the halogenation can be done by reacting Compound (IVa) with a halogenating reagent in the presence of a base in a suitable solvent. The solvent should be selected depending on the starting compound, etc., which includes, for example, THF, dioxane, DME, HMPA, and DMPU. The solvent may be used alone or as a mixture thereof. The base used herein includes, for example, an alkyl lithium reagent such as n-butyllithium and s-butyllithium; and an alkaline metal reagent such as lithium hexamethyldisilazide, sodium hexamethyldisilazide, sodium hydride, and potassium t-butoxide. The halogenating reagent used herein includes, for example, N-fluorobenzenesulfonimide, (diethylamino)sulfur trifluoride, and bis(2-methoxyethyl)aminosulfur trifluoride. The reaction temperature should be decided depending on the starting compound or reagent to be used, etc., which may be generally −100° C. to 50° C., preferably −78° C. to 25° C. The reaction time may be generally 30 minutes to 24 hours.

(Step 5): Compound (IIa) can be prepared by alkylating or halogenating Compound (IIIa).

The alkylation or halogenation of Step 5 in a conventional manner. For example, the alkylation can be done by reacting Compound (IIIa) with an alkyl halide $R^2X$ in the presence of a base in a suitable solvent, and the halogenation can be done by reacting Compound (IIIa) with a halogenating reagent in the presence of a base in a suitable solvent. The solvent should be selected depending on the starting compound, etc., which includes, for example, THF, dioxane, DME, HMPA, and DMPU. The solvent may be used alone or as a mixture thereof. The base used herein includes, for example, an alkyl lithium reagent such as n-butyllithium and s-butyllithium; and an alkaline metal reagent such as lithium hexamethyldisilazide, sodium hexamethyldisilazide, sodium hydride, and potassium t-butoxide. The halogenating reagent used herein includes, for example, N-fluorobenzenesulfonimide, (diethylamino)sulfur trifluoride, and bis(2-methoxyethyl)aminosulfur trifluoride. The reaction temperature should be decided depending on the starting compound or reagent to be used, etc., which may be generally −100° C. to 50° C., preferably −78° C. to 25° C. The reaction time may be generally 30 minutes to 24 hours.

When $R^1$ and $R^2$ are different, and at least one of $P^1$ and $P^2$ is an optically active form in Compound (IIa), Compound (IIa) is a diastereomeric mixture. When Compound (IIa) is a diastereomeric mixture, it can be resolved in a conventional manner. For example, the diastereomeric resolution can be done by chromatography, fractional crystallization, etc.

Preparation Process 3

Compound (IIa) which is used in Preparation process 1 can be also prepared according to the process in the following scheme.

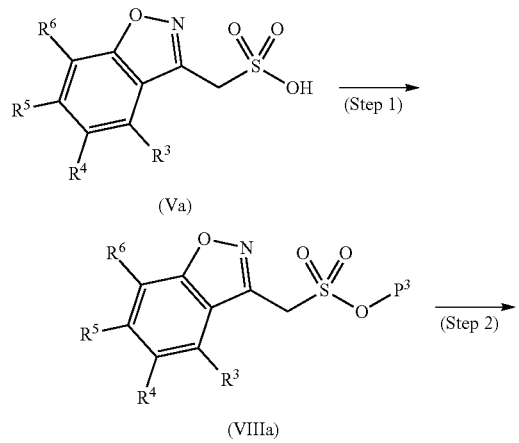

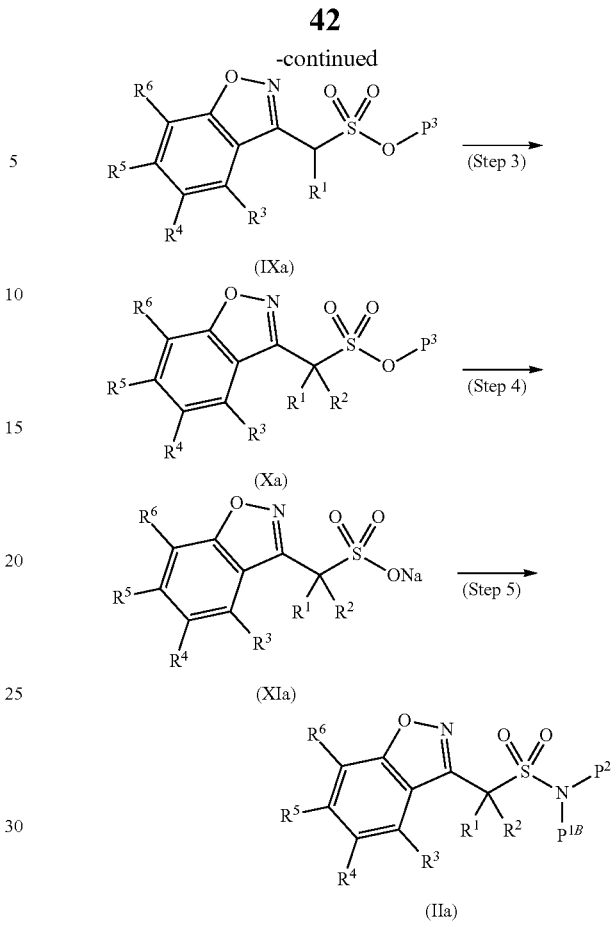

Wherein $R^1$, $R^2$, $R^3$, $R^4$, $R^5$, $R^6$, and $P^2$ are as defined in Preparation process 1; $P^{1B}$ is hydrogen, or a protection group for nitrogen atom which can be removed under an acidic condition, including 2,4-dimethoxybenzyl, p-methoxybenzyl, 2-indanol-1-yl, 2-phenylethan-1-ol-2-yl, 3-methylbutan-1-ol-2-yl, and the like; and $P^3$ is a protection group for oxygen atom, including optionally-substituted $C_{1-6}$ alkyl, optionally-substituted $C_{3-6}$ cycloalkyl, and the like.

(Step 1): Compound (VIIIa) can be prepared by esterifying Compound (Va).

The reaction of Step 1 can be done in a conventional manner. For example, the reaction can be done by reacting Compound (Va) with an alkyl halide in the presence of a silver salt in a suitable solvent. The solvent should be selected depending on the starting compound, etc., which includes, for example, ethers such as $Et_2O$, THF, dioxane, and DME; alcohols such as methanol, ethanol, and isopropyl alcohol; water; toluene; acetonitrile; DMF; NMP; and DMSO. The solvent may be used alone or as a mixture thereof. And, the silver salt used herein includes, for example, silver oxide, silver chloride, and silver bromide. The reaction temperature should be decided depending on the starting compound or reagent to be used, etc., which may be generally −100° C. to 200° C., preferably 0° C. to 150° C. The reaction time may be generally 30 minutes to 24 hours.

(Step 2): Compound (IXa) can be prepared by alkylating or halogenating Compound (VIIIa). When $R^1$ is hydrogen, the present step is omitted.

The alkylation or halogenation of Step 2 can be done according to Step 4 in Preparation process 2.

(Step 3): Compound (Xa) can be prepared by alkylating or halogenating Compound (IXa).

The alkylation or halogenation of Step 3 can be done according to Step 5 in Preparation process 2.

(Step 4): Compound (XIa) can be prepared by de-esterifying Compound (Xa).

The reaction of Step 4 can be done in a conventional manner. For example, the reaction can be done by reacting Compound (Xa) with an alkaline metal iodide in a suitable solvent. The solvent should be selected depending on the starting compound, etc., which includes, for example, THF, dioxane, DME, toluene, acetonitrile, DMF, and NMP. The solvent may be used alone or as a mixture thereof. The alkaline metal iodide includes, for example, sodium iodide and potassium iodide. The reaction temperature should be decided depending on the starting compound or reagent to be used, etc., which may be generally −100° C. to 200° C., preferably 0° C. to 150° C. The reaction time may be generally 30 minutes to 24 hours.

(Step 5): Compound (IIa) can be prepared by sulfonamidating Compound (XIa).

The reaction of Step 5 can be done in a conventional manner. For example, the reaction can be done by converting the sulfonate in Compound (XIa) to its sulfonyl chloride, followed by reacting with an amine compound. The conversion to sulfonyl chloride can be done by reacting a sulfonate compound with phosphorus oxychloride in a solvent or without a solvent. The solvent should be selected depending on the starting compound, etc., which includes, for example, Et$_2$O, THF, dioxane, DME, and toluene. The solvent may be used alone or as a mixture thereof. The reaction temperature should be decided depending on the starting compound or reagent to be used, etc., which may be generally −100° C. to 200° C., preferably 0° C. to 150° C. The reaction time may be generally 30 minutes to 24 hours. The conversion of a sulfonyl chloride compound which is an intermediate at Step 5 to its sulfonamide compound can be done according to Step 3 in Preparation process 2.

When R$^1$ and R$^2$ are both hydrogen in Compound (IIa), the subsequent deprotection step is not necessary.

When R$^1$ and R$^2$ are different, and at least one of P$^{1B}$ and P$^2$ is an optically active form in Compound (IIa), Compound (IIa) is a diastereomeric mixture. When Compound (IIa) is a diastereomeric mixture, it can be resolved according to the method described at Step 5 in Preparation process 2.

Preparation Process 4

Compound (XIa) which is used in Preparation process 3 can be also prepared according to the process in the following scheme.

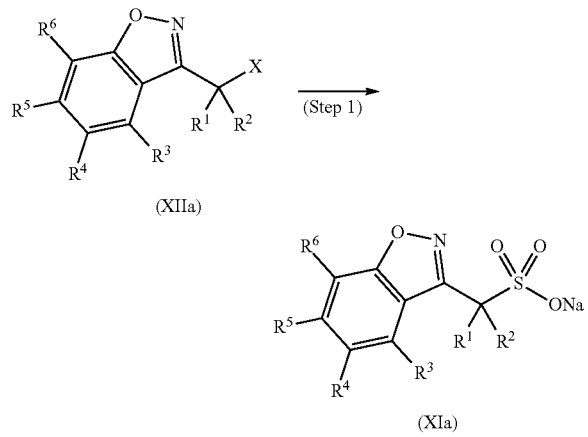

(XIIa)

(XIa)

Wherein R$^1$, R$^2$, R$^3$, R$^4$, R$^5$, and R$^6$ are as defined in Item 1; and X is a leaving group, including halogen, toluenesulfonyloxy, methanesulfonyloxy, trifluoromethanesulfonyloxy, and the like.

(Step 1): Compound (XIa) can be prepared by making a substitution reaction on Compound (XIIa).

The substitution reaction of Step 1 can be done in a conventional manner. For example, the reaction can be done by reacting Compound (XIIa) with a sulfite compound in a suitable solvent. The solvent should be selected depending on the starting compound, etc., which includes, for example, THF, dioxane, acetonitrile, DMF, acetone, water, ethanol, and methanol. The solvent may be used alone or as a mixture thereof. The sulfite compound used herein includes sodium sulfite, sodium bisulfite, ammonium sulfite, methylamine sulfite, ethylamine sulfite, dimethylamine sulfite, and triethylamine sulfite. The reaction temperature should be decided depending on the starting compound or reagent to be used, etc., which may be generally −100° C. to 150° C., preferably 0° C. to 100° C. The reaction time may be generally 30 minutes to one week.

Preparation Process 5

Compound (Ia) which is used in Preparation process 1 can be also prepared according to the process in the following scheme.

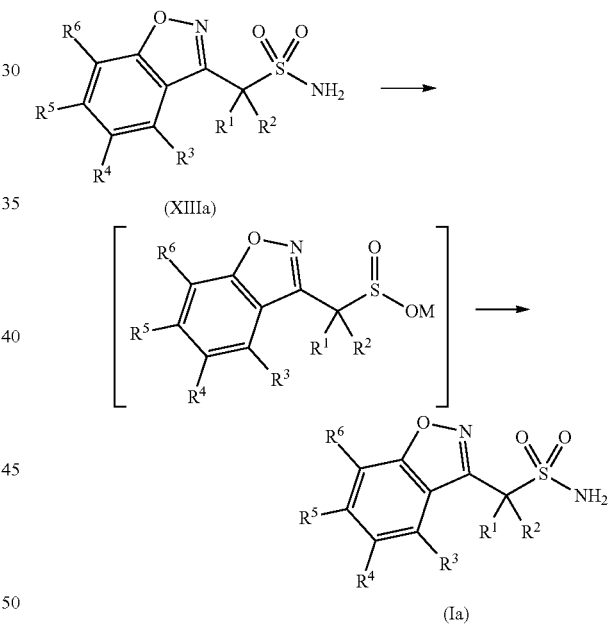

(XIIIa)

(Ia)

Wherein R$^1$, R$^2$, R$^3$, R$^4$, R$^5$, and R$^6$ are as defined in Item 1; R$^7$ is a leaving group which can be removed under a suitable condition to release the corresponding sulfinic acid salt, including 2-(methoxycarbonyl)ethyl, mesitylenecarbonyloxymethyl, 2-benzothiazolyl (the benzene ring of which may be substituted with 1-3 substituents selected independently from the group consisting of halogen, C$_{1-6}$ alkyl (which may be substituted with 1-3 substituents selected independently from the group consisting of halogen, hydroxy, C$_{3-6}$ cycloalkyl, and C$_{1-3}$ alkoxy), C$_{1-6}$ alkoxy (which may be substituted with 1-3 substituents selected independently from the group consisting of halogen, hydroxy, C$_{3-6}$ cycloalkyl, and C$_{1-3}$ alkoxy), hydroxy, cyano, nitro, amino (which may be substituted with 1-2 C$_{1-3}$ alkyl), carboxylic acid, carbamoyl (the amino moiety of which may be substituted with 1-2 $C_{1-3}$ alkyl), and $C_{1-6}$ alkoxycarbonyl), 2-pyridyl, 2-pyrimidinyl, and 2-(trimethylsilyl)ethyl; and M is a metallic ion or quaternary ammonium ion.

Compound (Ia) can be prepared by decomposing Compound (XIIIa) and then reacting with an amination reagent.

The removal of the leaving group in Compound (XIIIa) can be done in a conventional manner. For example, when $R^7$ is 2-(methoxycarbonyl)ethyl group, the removal can be done by reacting with a base in a suitable solvent. The base used herein includes sodium methoxide and sodium carbonate. And, when $R^7$ is 2-pyridyl group, 2-pyrimidinyl group, or 2-benzothiazolyl group, the removal can be done by a suitable nucleophilic agent in a suitable solvent. The nucleophilic agent used herein includes sodium ethoxide, sodium ethanethiolate, sodium borohydride, and lithium aluminum hydride. And, when $R^7$ is 2-(trimethylsilyl)ethyl group, the removal can be done by a suitable fluoride reagent in a suitable solvent. The fluoride reagent used herein includes tetrabutylammonium fluoride, and tris(dimethylamino)sulfonium difluorotrimethylsilicate.

The intermediate sulfinate can be transformed to its sulfonamide by reacting with ammonia or its salt and an oxidizing agent in the presence of a base in a solvent, or reacting with an ammonia bound to a leaving group in the presence of a base in a solvent. The solvent should be selected depending on the starting compound, etc., which includes, for example, ethanol, methanol, water, THF, dioxane, DME, DMF, and acetonitrile. The solvent may be used alone or as a mixture thereof. And, the base used herein includes, for example, sodium carbonate, sodium bicarbonate, and sodium acetate. The oxidizing agent includes metachloroperoxybenzoic acid (mCPBA). The ammonia bound to a leaving group includes, for example, hydroxylamine-O-sulfonic acid, O-mesitylenesulfonylhydroxylamine, and monochloramine. The reaction temperature should be decided depending on the starting compound or reagent to be used, etc., which may be generally −100° C. to 200° C., preferably −20° C. to 100° C. The reaction time may be generally 30 minutes to 24 hours.

Preparation Process 6

Compound (XIIIa) which is used in Preparation process 5 can be prepared according to the process in the following scheme.

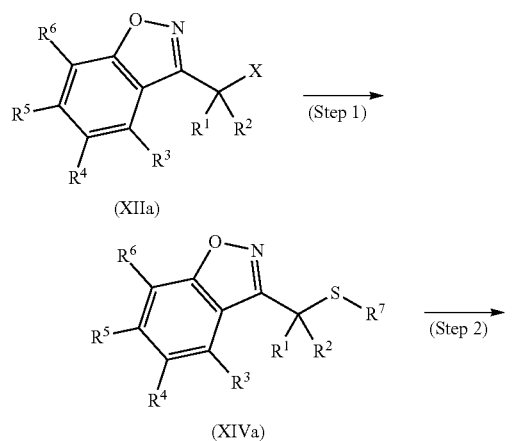

(XIIa)

(XIVa)

-continued

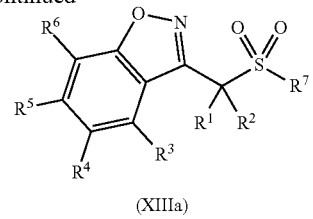

(XIIIa)

Wherein $R^1$, $R^2$, $R^3$, $R^4$, $R^5$, and $R^6$ are as defined in Item 1; $R^7$ is as defined in Preparation process 5; and X is as defined in Preparation process 4.

(Step 1): Compound (XIVa) can be prepared by making a substitution reaction on Compound (XIIa).

The substitution reaction of Step 1 can be done in a conventional manner. For example, the reaction can be done by reacting Compound (XIIa) with an alkaline metal salt of thiol ($R^7$—SH) in a suitable solvent. The alkaline metal salt includes, for example, lithium salt, sodium salt, and potassium salt. The solvent should be selected depending on the starting compound, etc., which includes, for example, THF, dioxane, acetonitrile, DMF, toluene, and chlorobenzene. The solvent may be used alone or as a mixture thereof. The reaction temperature should be decided depending on the starting compound or reagent to be used, etc., which may be generally −100° C. to 150° C., preferably −20° C. to 100° C. The reaction time may be generally 30 minutes to 24 hours.

(Step 2): Compound (XIIIa) can be prepared by oxidizing Compound (XIVa).

The oxidation reaction of Step 2 can be done in a conventional manner. For example, the reaction can be done by reacting Compound (XIVa) with an oxidizing agent in a suitable solvent. The solvent should be selected depending on the starting compound, etc., which includes, for example, dichloromethane, chloroform, acetonitrile, DMF, toluene, and chlorobenzene. The solvent may be used alone or as a mixture thereof. The oxidizing agent used herein includes potassium permanganate, sodium tungstate and hydrogen peroxide, mCPBA, magnesium bis(monoperoxyphthalate) hexahydrate, and oxone. The reaction temperature should be decided depending on the starting compound or reagent to be used, etc., which may be generally −100° C. to 150° C., preferably −10° C. to 100° C. The reaction time may be generally 30 minutes to 48 hours.

Preparation Process 7

Compound (XIVa) which is used in Preparation process 6 can be prepared according to the process in the following scheme.

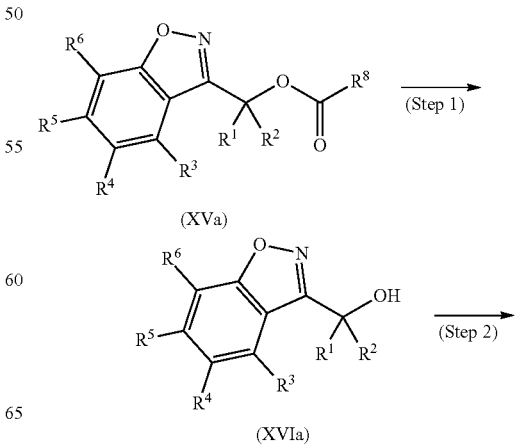

(XVa)

(XVIa)

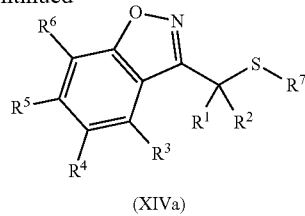

(XIVa)

Wherein $R^1$, $R^2$, $R^3$, $R^4$, $R^5$, and $R^6$ are as defined in Item 1; $R^7$ is as defined in Preparation process 5; and $R^8$ is $C_{1-6}$ alkyl (which may be substituted with 1-3 substituents selected independently from the group consisting of halogen, hydroxy, $C_{3-5}$ cycloalkyl, and $C_{1-3}$ alkoxy), $C_{1-6}$ alkoxy, or $C_{1-6}$ alkylcarbonyloxymethoxy.

(Step 1): Compound (XVIa) can be prepared by hydrolyzing Compound (XVa).

The reaction of Step 1 can be done in a conventional manner. For example, the reaction can be done by reacting Compound (XVa) in the presence of an acid or a base in a suitable aqueous solvent. The aqueous solvent should be selected depending on the starting compound, etc., which includes, for example $Et_2O$, THF, dioxane, DME, DMF, acetonitrile, acetone, toluene, methanol, and ethanol. The solvent may be used alone or as a mixture thereof. And, the acid used herein includes hydrochloric acid, sulfuric acid, and trifluoroacetic acid; and the base used herein includes sodium hydroxide, potassium hydroxide, lithium hydroxide, and sodium carbonate. The reaction temperature should be decided depending on the starting compound or reagent to be used, etc., which may be generally 0° C. to 120° C., preferably 40° C. to 100° C. The reaction time may be generally 30 minutes to 24 hours.

In case that $R^1$ and $R^2$ are different, the corresponding optically-active Compound (XVIa) can be obtained by reacting Compound (XVa) with a hydrolase in an aqueous solvent. The solvent should be selected depending on the starting compound, etc., which includes, for example, THF, DMSO, acetonitrile, acetone, toluene, ethanol, and hexane. The solvent may be used alone or as a mixture thereof. And, the hydrolase used herein includes lipase, esterase, amidase, and protease. The reaction temperature should be decided depending on the starting compound or reagent to be used, etc., which may be generally 0° C. to 100° C., preferably 20° C. to 60° C. The reaction time may be generally 30 minutes to one week.

(Step 2): Compound (XIVa) can be prepared by making a substitution reaction on Compound (XVIa).

The substitution reaction of Step 2 can be done in a conventional manner. For example, the reaction can be done by reacting Compound (XVIa) with thiol ($R^7SH$), a Mitsunobu reagent, and a phosphine reagent in a suitable solvent, or with a disulfide ($R^7S$—$SR^7$) and a phosphine reagent in a suitable solvent. The solvent should be selected depending on the starting compound, etc., which includes, for example, THF, dioxane, acetonitrile, DMF, toluene, and chlorobenzene. The solvent may be used alone or as a mixture thereof. The Mitsunobu reagent used herein includes diethyl azodicarboxylate, diisopropyl azodicarboxylate, N,N,N',N'-tetramethyl-azodicarboxamide, and 1,1'-(azodicarbonyl)dipiperidine. The phosphine reagent includes triphenylphosphine and tri-n-butylphosphine. The reaction temperature should be decided depending on the starting compound or reagent to be used, etc., which may be generally −100° C. to 150° C., preferably −20° C. to 100° C. The reaction time may be generally 30 minutes to 24 hours.

Preparation Process 8

Compound (XVIb) which corresponds to Compound (XVIa) used in Preparation process 7 wherein $R^1$ is hydrogen can be also prepared according to the process in the following scheme.

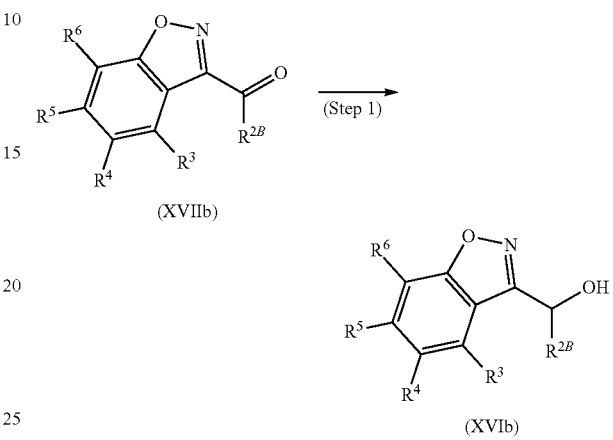

Wherein $R^3$, $R^4$, $R^5$, and $R^6$ are as defined in Item 1; and $R^{2B}$ is halogen, $C_{1-6}$ alkyl (which may be substituted with 1-3 substituents selected independently from the group consisting of halogen, hydroxy, $C_{3-6}$ cycloalkyl, and $C_{1-3}$ alkoxy), or $C_{3-6}$ cycloalkyl (which may be substituted with 1-3 substituents selected independently from the group consisting of halogen, hydroxy, $C_{1-3}$ alkyl, and $C_{1-3}$ alkoxy).

(Step 1): Compound (XVIb) can be prepared by reducing Compound (XVIIb).

The reduction of Compound (XVIIb) in Step 1 can be done in a conventional manner. For example, the reaction can be done by reacting Compound (XVIIb) with a reducing agent in a suitable solvent. The solvent should be selected depending on the starting compound, etc., which includes, for example, THF, acetonitrile, DMF, toluene, methanol, ethanol, 2-propanol, and water. The solvent may be used alone or as a mixture thereof. The reducing agent used herein includes sodium borohydride, lithium borohydride, and lithium aluminum hydride. The reaction temperature should be decided depending on the starting compound or reagent to be used, etc., which may be generally −100° C. to 150° C., preferably −10° C. to 100° C. The reaction time may be generally 30 minutes to 48 hours.

An optically-active Compound (XVIb) can be obtained by asymmetric reduction. For example, the reaction can be done by reacting Compound (XVIIb) with a reductase and a coenzyme in an aqueous solvent. The solvent should be selected depending on the starting compound, etc., which includes, for example, THF, DMSO, acetonitrile, acetone, toluene, ethanol, and hexane. The solvent may be used alone or as a mixture thereof. The reductase used herein includes carbonyl reductase and alcohol dehydrogenase. The coenzyme includes NADH and NADPH. The reaction temperature should be decided depending on the starting compound or reagent to be used, etc., which may be generally 0° C. to 100° C., preferably 20° C. to 60° C. The reaction time may be generally 30 minutes to one week.

In addition, each intermediate or each final product in the above preparation processes can be also transformed to another compound of the present invention by suitably modifying its functional group, especially extending various side-chains from amine, hydroxy, carbonyl, halogen, etc.; and optionally making the above-mentioned protection and deprotection if necessary. The modification of functional group and the extension of side-chain can be done by a conventional method (for example, see, Comprehensive Organic Transformations, R. C. Larock, John Wiley & Sons Inc. (1999), etc.).

The present compounds of formula (1) or a pharmaceutically acceptable salt thereof are sometimes asymmetric compounds or sometimes have a substituent including an asymmetric carbon. In such case, the compounds have optical isomers. The present compounds include a mixture of these isomers and an isolated one, which can be prepared in a conventional manner. The compounds having an asymmetric structure can be prepared, for example, by using a starting material having an asymmetric center or by introducing an asymmetric structure anywhere along the process. For example, in case of optical isomers, optical isomers can be obtained by using an optically active starting material or resolving a mixture of optical isomers at an appropriate step. In case that the compound of formula (1) or its intermediate has a basic functional group, the optical resolution thereof includes, for example, diastereomer method, wherein the compound is transformed to a salt thereof by reacting with an optically active acid (for example, a monocarboxylic acid such as mandelic acid, N-benzyloxyalanine, and lactic acid; dicarboxylic acid such as tartaric acid, o-diisopropylidenetartaric acid, and malic acid; or a sulfonic acid such as camphorsulfonic acid and bromocamphorsulfonic acid), in an inert solvent (for example, an alcohols such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent thereof). In case that the compound of formula (1) or its intermediate has an acidic functional group such as carboxyl group, the compound can be also optically resolved by forming its salt with an optically active amine (for example, an organic amine such as 1-phenylethylamine, quinine, quinidine, cinchonidine, cinchonine, and strychnine).

The temperature for forming a salt is selected from the range of generally −50° C. to boiling point of a solvent used herein, preferably 0° C. to the boiling point, and more preferably room temperature to the boiling point. In order to enhance the optical purity, it is desirable to make the temperature raised to around boiling point of a solvent used herein. In collecting a precipitated crystal on a filter, an optional cooling can make the yield increased. The amount of an optically active acid or amine used herein is suitably about 0.5-about 2.0 equivalents against that of the substance compound, preferably around one equivalent. If appropriate, the obtained crystal may be recrystallized in an inert solvent (for example, an alcohols such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent thereof) to obtain its highly pure salt thereof. And, if appropriate, the optically-resolved salt can be also treated with an acid or a base to obtain its free form.

Among the starting materials and the intermediates in each preparation process mentioned above, the compounds that are not described about each preparing process are commercially available or can be prepared by a skilled person with a commercial available material in a known manner or a similar manner thereto.

The novel benzisoxazole derivative of the present invention has T-type calcium channel inhibitory activity, and thereby it is useful as a medicament for treating and/or preventing various nervous system diseases or psychiatric diseases which are initiated by abnormality of T-type calcium channel, for example, epilepsy; seizure disorder; motor dysfunction (e.g. muscle spasm-related disorder including convulsion; tremor; essential tremor; Huntington's disease; myoclonus; tic; restless legs syndrome; and dystonia); movement disorder including akinesia and stiff-man syndrome, and parkinsonism (which includes Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), episodic and drug-induced parkinsonism, postencephalitic parkinsonism, progressive supranuclear palsy, multiple system atrophy, corticobasal degeneration, dementia with Lewy body, cerebellar ataxia, parkinsonism-ALS dementia complex, and basal ganglia calcification); drug-induced dyskinesia; nociceptive pain (including traumatic pain, migraine, headache, chronic pain (e.g. low back pain, rheumatoid arthralgia, fibromyalgia, osteoarthritis, and the like), and inflammatory pain); neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain); fatigue (e.g. Parkinson fatigue, multiple sclerosis fatigue, fatigue caused by sleep disorder or circadian rhythm disorder, chronic fatigue syndrome including drug-induced parkinsonism, and the like); migraine; schizophrenia; autism; Gilles de la Tourette syndrome; bipolar disorder; depressive disorder; anxiety (including generalized anxiety disorder, panic disorder, and obsessive-compulsive disorder); sleep disorder (including insomnia, hypersomnia, narcolepsy, and REM sleep disorder); cardiac arrhythmia; hypertension; cancer; diabetes; infertility; and sexual dysfunction.

The novel benzisoxazole derivative of the present invention is preferably useful as a medicament for treating and/or preventing essential tremor; Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache); or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain).

The novel benzisoxazole derivative of the present invention is more preferably useful as a medicament for treating and/or preventing essential tremor, tremor in Parkinson's disease, or chemotherapy-induced peripheral neuropathy.

The novel benzisoxazole derivative of the present invention is useful as a medicament for treating and/or preventing various diseases and disorders which include epilepsy; seizure disorder; motor dysfunction (e.g. muscle spasm-related disorder including convulsion; tremor; essential tremor; Huntington's disease; myoclonus; tic; restless legs syndrome; and dystonia); movement disorder including akinesia and stiff-man syndrome, and parkinsonism (which includes Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache), episodic and drug-induced parkinsonism, postencephalitic parkinsonism, progressive supranuclear palsy, multiple system atrophy, corticobasal degeneration, dementia with Lewy body, cerebellar ataxia, parkinsonism-ALS dementia complex, and basal ganglia calcification); levodopa-induced dyskinesia in Parkinson's disease; drug-induced dyskinesia; nociceptive pain (including traumatic pain, migraine, headache, chronic pain (e.g. low back pain, rheumatoid arthralgia, fibromyalgia, osteoarthritis, and the like), and inflammatory pain); neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain); fatigue (e.g. Parkinson fatigue, multiple sclerosis fatigue, fatigue caused by sleep disorder or circadian rhythm disorder, chronic fatigue syndrome including drug-induced parkinsonism, and the like); migraine; schizophrenia; autism; Gilles de la Tourette syndrome; bipolar disorder; depressive disorder; anxiety (including generalized anxiety disorder, panic disorder, and obsessive-compulsive disorder); sleep disorder (including insomnia, hypersomnia, narcolepsy, and REM sleep disorder); sleep disorder in depressive disorder; cardiac arrhythmia; hypertension; cancer; diabetes; infertility; and sexual dysfunction.

The novel benzisoxazole derivative of the present invention is preferably useful as a medicament for treating and/or preventing Parkinson's disease (including a symptom such as tremor, muscle stiffness/muscle rigidity, akinesia/bradykinesia, impairment of postural reflex, smell disorder, REM sleep disorder, constipation, sleep disorder, memory impairment, depression, anxiety, headache, and backache); levodopa-induced dyskinesia in Parkinson's disease; essential tremor; anxiety (including generalized anxiety disorder); or neuropathic pain (including zoster-associated pain, trigeminal neuralgia, complex regional pain syndrome, peripheral neuropathy (e.g. diabetic neuropathy, leprosy, and the like), chemotherapy-induced peripheral neuropathy, phantom pain, central pain (e.g. spinal post-injury pain, post-stroke pain, and the like), pain associated with Guillain-Barre syndrome, pain associated with multiple sclerosis, pain associated with Parkinson's disease, and hyperalgesia or allodynia associated with neuropathic pain).

The novel benzisoxazole derivative of the present invention is more preferably useful as a medicament for treating and/or preventing Parkinson's disease (including tremor, muscle stiffness/muscle rigidity, akinesia/bradykinesia, and impairment of postural reflex), essential tremor, or chemotherapy-induced peripheral neuropathy.

In addition, the present compound has potentiating effect of levodopa-induced hyperactivity which is different from the activity derived by MAOB inhibitory action. And, preferred compounds of the present invention have lower risk of nephrolithiasis because the action inhibiting carbonic anhydrase is attenuated. Thus, for highly safe treatment for Parkinson's disease, the present compound is useful as a combination drug with a levodopa preparation. In addition, the present compound inhibited the onset of dyskinesia in a levodopa-induced dyskinesia model, thus the present compound is useful as a medicament for treating and/or preventing Parkinson's disease, which is highly safe unlike existing drugs for combination with levodopa which have high risk of developing a drug-induced dyskinesia. In addition, the present compound exhibited effectivity for Parkinson's tremor model and essential tremor model, thus the present compound is useful as a medicament for treating and/or preventing Parkinson's tremor, essential tremor, as well as parkinsonism developed in nervous system diseases or psychiatric diseases. In addition, the present compound exhibited anxiolytic-like effect in elevated plus maze test, and shortening of non-REM sleep latency or shortening of waking hours in sleep electroencephalogram test, thus the present compound is useful as a medicament for treating and/or preventing non-motor symptoms of Parkinson's disease such as psychiatric symptom and sleep disorder.

Furthermore, the present compound exhibited antiallodynic effect for oxaliplatin-induced pain model, thus the present compound is also useful as a medicament for treating and/or preventing neuropathic pain (in particular, pain and allodynia in chemotherapy-induced peripheral neuropathy).

In the present invention, the "prevention/preventing" means that the active ingredient of the present invention is administered to a healthy subject who does not suffer from the disease, for example, said purpose of the administration is for preventing the onset of the disease. The "treatment/treating" means that the active ingredient of the present invention is administered to a subject who is diagnosed with the disease by a physician (i.e., a patient). The administration to a patient suffering from the disease for inhibiting seizure associated with the disease is included in the "prevention/preventing" or "treatment/treating".

The novel benzisoxazole derivative of the present invention has low MAOB inhibitory action, compared with a MAOB inhibitor, rasagiline or safinamide. Thus, it is a safe drug which is less likely to cause dyskinesia when it is repeatedly administered in combination with levodopa. The "low MAOB inhibitory action" used herein means that when the MAOB inhibitory action is measured under the condition defined in Test 6 herein, $IC_{50}$ value is 70 μmol/L or more, preferably 100 μmol/L or more.

In preferred embodiment of the present invention, the novel benzisoxazole derivative is a safe agent having low risk of urolithiasis and the like because it has weak activity for inhibiting CA-II, compared with a carbonic anhydrase inhibitor, topiramate or acetazolamide. In the present invention, "weak activity for inhibiting CA-II" means that the compound exhibits $IC_{50}$ of 1 μmol/L or more in the activity for inhibiting CA-II measured under the condition in Test 9 mentioned below, preferably 3 μmol/L or more, and more preferably 10 μmol/L or more.

The present compounds may be administered orally, parenterally or rectally, and the daily dose can vary depending on the compound, the mode of administration, patient's condition/age, etc. For oral administration, for example, the present compounds may be administered generally in a dosage of about 0.01 to 1000 mg, preferably about 0.1 to 500 mg a day per kilogram of body weight of human or mammal and once to several times. For parenteral administration such as intravenous injection, for example, the present compounds may be administered generally in a dosage of about 0.01 to 300 mg, preferably about 1 to 100 mg per kilogram of body weight of human or mammal.

When the present compound is used for medical use mentioned above, generally the compound is mixed with a pharmaceutical carrier to prepare a drug formulation to be administered. The pharmaceutical carrier used herein is a non-toxic substance which is regularly used in pharmaceutical field and cannot be reacted with the present compound. It includes, for example, citric acid, glutamate, glycine, lactose, inositol, glucose, mannitol, dextran, sorbitol, cyclodextrin, starch, partly pregelatinized starch, white soft sugar, methyl p-hydroxybenzoate, propyl p-hydroxybenzoate, magnesium aluminometasilicate, synthetic aluminum silicate, microcrystalline cellulose, carboxymethylcellulose sodium, hydroxypropyl starch, carboxymethylcellulose calcium, ion exchange resin, methylcellulose, gelatin, gum arabic, pullulan, hydroxypropylcellulose, low substituted hydroxypropylcellulose, hydroxypropylmethylcellulose, polyvinylpyrrolidone, polyvinyl alcohol, alginic acid, sodium alginate, light anhydrous silicic acid, magnesium stearate, talc, tragacanth, bentonite, veegum, carboxy vinyl polymer, titanium oxide, sorbitan fatty acid ester, sodium lauryl sulfate, glycerol, glycerol fatty acid ester, purified lanolin, glycerogelatin, polysorbate, macrogol, vegetable oil, wax, propylene glycol, ethanol, benzyl alcohol, sodium chloride, sodium hydroxide, hydrochloric acid, and water.

The formulation type includes tablet, capsule, granule, powder, syrup, suspension, injection, suppository, eyedrop, ointment, endermic liniment, plaster, and inhalant. These formulations can be prepared in a conventional manner. The formulation which is a liquid may be obtained by dissolving or suspending the present pharmaceutical composition in water or other suitable solvents before use. The tablet and capsule may be coated in a conventional manner. In addition, these formulations may comprise another active ingredient which is useful for the treatment.

The present compound may be used in combination with at least one drug selected from the drug-group classified as drugs for treating Parkinson's disease, drugs for treating essential tremor, or drugs for treating neuropathic pain. The "used in combination with" used herein means that the other drug is administered in a different formulation from that of the present compound, and the other drug may be administered to a subject at the same time of the administration of the present compound or at a time interval from the administration of the present compound.

The drug-group classified as drugs for treating Parkinson's disease includes, for example, levodopa, carbidopa, entacapone, MAOB inhibitor (such as selegiline, rasagiline, and safinamide), dopamine receptor agonist (such as bromocriptine, pergolide, talipexole, cabergoline, pramipexole, ropinirole, rotigotine, and apomorphine), amantadine, droxidopa, istradefylline, anticholinergic agent (such as trihexyphenidyl and biperiden).

The drug-group classified as drugs for treating essential tremor includes, for example, arotinolol, primidone, and propranolol.

The drug-group classified as drugs for treating neuropathic pain includes, for example, serotonin-noradrenaline reuptake inhibitor (such as duloxetine, venlafaxine, and milnacipran), tricyclic antidepressant (such as amitriptyline, imipramine, clomipramine, nortriptyline, and desipramine), serotonin reuptake inhibitor (such as paroxetine hydrochloride, escitalopram, fluvoxamine maleate, and sertraline hydrochloride), mirtazapine, an extract from inflammatory rabbit skin inoculated by vaccinia virus, tramadol, buprenorphine, gabapentin, pregabalin, carbamazepine, oxcarbazepine, sodium valproate, lamotrigine, topiramate, dextromethorphan hydrobromide, mexiletine hydrochloride, and vitamin B12.

EXAMPLES

The present invention is explained in more detail in the following by referring to Reference examples, Examples, and Tests; however, the technical scope of the present invention is not limited thereto. The compound names used in Reference examples and Examples are not always based on IUPAC nomenclature system.

In order to simplify description, abbreviations shown below may be sometimes used in Reference examples, Examples, and tables in Examples. THF: tetrahydrofuran, DMSO: dimethylsulfoxide, TFA: trifluoroacetic acid, Et$_2$O: diethyl ether, DMF: N,N-dimethylformamide, DME: 1,2-dimethoxyethane, NMP: N-methylpyrrolidone, HMPA: hexamethylphosphoric triamide, HMPU: dimethylpropylene urea. The symbols used in NMR are defined as follows, s: singlet, d: doublet, dd: doublet of doublet, t: triplet, td: triplet of doublet, q: quartet, m: multiplet, br: broad, brs: broad singlet, brm: broad multiplet, and J: coupling constant. As a term used in the syntheses of optically active compounds, "ee" means enantiomeric excess.

Various data described in Reference examples and Examples were obtained with the instruments shown below. NMR spectrum: [$^1$H-NMR] 400 MHz: JEOL JNM-AL series AL400 LC-MS spectrum: Waters ACQUITY™ Ultra-Performance LC, Agilent 1260 InfinityHPLC-Agilent 6120 Quadrupole LC/MS Determination of optical purity: Shimadzu LC-20AT HPLC system, Agilent 1200 HPLC system High-performance liquid chromatography mass spectrometer; the measurement conditions of LCMS are shown below, in which the observed result of mass analysis [MS (m/z)] is shown as MH$^-$, and the retention time is shown as Rt (min).

Measurement Condition (i)
Column: ACQUITY UPLC BEH C18 1.7 μm 2.1×30 mm column
Solvent: A: 0.05% HCOOH/H$_2$O, B: CH$_3$CN
Gradient condition: 0.0-1.3 min; A/B=90/10-5/95 (linear gradient) 1.3-1.5 min; A/B=90/10
Flow rate: 0.80 mL/min
UV: 220 nm, 254 nm
Column temperature: 40° C.

Measurement Condition (ii)
Column: ZORBAX SB-C18 2.1×50 mm 1.8 μm
Solvent: A: 0.1% HCOOH/H$_2$O, B: CH$_3$CN
Gradient condition: B % 5% (ini)→90% (5-6分)→5% (6-10 min)
Flow rate: 0.60 mL/min
UV: 210 nm, 254 nm, 280 nm
Column temperature: 40° C.

Reference Example 1

2-(Benzo[d]isoxazol-3-yl)acetic acid (IUPAC Name: (1,2-benzoxazol-3-yl)acetic acid)

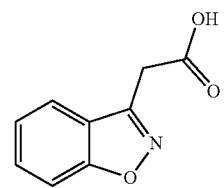 [SMILES: O=C(O)Cc1noc2ccccc12]

4-Hydroxy-2H-chromen-2-one (1.00 g) and disodium dihydrogen ethylenediaminetetraacetate dihydrate (0.18 g) were added to a mixture of hydroxylamine sulfate (2.03 g), water (5.6 mL), and 25% aqueous sodium hydroxide (2.7 mL), and the mixture was stirred at 85° C. for 4 hours. The reaction solution was acidified with sulfuric acid, and then extracted with dichloroethane. The organic layer was dried over sodium sulfate, and concentrated under reduced pressure to give the title compound (862 mg).

$^1$H-NMR (DMSO-$d_6$) δ: 4.09 (s, 2H), 7.39 (dd, 1H), 7.65 (ddd, 1H), 7.73 (d, 2H), 7.84 (d, 1H)

Reference Examples 2-4

Each compound shown in Table 1 was prepared from each corresponding starting compound in similar reaction and treatment to the method described in Reference example 1.

TABLE 1

| Reference example | Structure |
|---|---|
| 2 | 5-methoxy-benzisoxazol-3-yl acetic acid |
| 3 | 5-fluoro-benzisoxazol-3-yl acetic acid |
| 4 | 5-chloro-benzisoxazol-3-yl acetic acid |

Reference Example 5

Benzo[d]isoxazol-3-ylmethanesulfonate (IUPAC Name: (1,2-benzoxazol-3-yl) methanesulfonate)

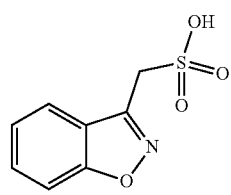 [SMILES: O=S(=O)(O)Cc1noc2ccccc12]

To a suspension of the compound prepared in Reference example 1 (17.0 g) in a mixture of toluene (150 mL)/ethyl acetate (25 mL) was added dropwise a solution of chlorosulfuric acid (9.6 mL) in 1,2-dichloroethane (50 mL) at room temperature, and then the mixture was stirred at 80° C. for 2 hours. The precipitated solid was collected on a filter, washed with toluene, and dried to give the title compound (20.5 g).

MS (m/z) 212 (MH−), Rt=0.28 min.

Reference Examples 6-8

Each compound shown in Table 2 was prepared from each corresponding starting compound in similar reaction and treatment to the method described in Reference example 5.

TABLE 2

| Reference example | Structure |
|---|---|
| 6 | 5-methoxy-benzisoxazol-3-yl methanesulfonic acid |
| 7 | 5-fluoro-benzisoxazol-3-yl methanesulfonic acid |
| 8 | 5-chloro-benzisoxazol-3-yl methanesulfonic acid |

Reference Example 9

1-(Benzo[d]isoxazol-3-yl)-N,N-bis(2,4-dimethoxybenzyl)methanesulfonamide (IUPAC Name: 1-(1,2-benzoxazol-3-yl)-N,N-bis[(2,4-dimethoxyphenyl)methyl]methanesulfonamide)

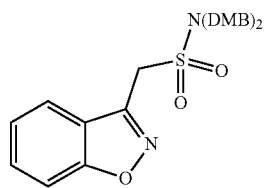

To a suspension of the compound prepared in Reference example 5 (5.30 g) in toluene (80 mL) was added phosphorus oxychloride (22.9 g), and the mixture was heated under reflux for 2 hours, and then concentrated under reduced pressure. The obtained residue was dissolved in THF (80 mL), and the solution was added dropwise to a solution of triethylamine (13.9 ml), 4-dimethylaminopyridine (0.30 g), and bis(2,4-dimethoxybenzyl)amine (7.89 mL) in THF (80 mL). The mixture was stirred at room temperature for 12 hours. The insoluble matter was removed on a filter, and the filtrate was concentrated under reduced pressure. The obtained residue was purified by silica gel column chromatography (eluting solvent; n-hexane:ethyl acetate; 1:2) to give the title compound (5.05 g) as a solid.

$^1$H-NMR (CDCl$_3$) δ: 3.77 (s, 6H), 3.77 (s, 6H), 4.31 (s, 4H), 4.45 (s, 2H), 6.39-6.41 (m, 4H), 7.18 (d, 2H), 7.31 (ddd, 1H), 7.52-7.54 (m, 2H), 7.88 (d, 1H)

Reference Examples 10-12

Each compound shown in Table 3 was prepared from each corresponding starting compound in similar reaction and treatment to the method described in Reference example 9.

TABLE 3

| Reference example | Structure |
|---|---|
| 10 | ![structure] |
| 11 | ![structure] |
| 12 | ![structure] |

Reference Example 13

1-(Benzo[d]isoxazol-3-yl)-N,N-bis(2,4-dimethoxybenzyl)ethane-1-sulfonamide (IUPAC Name: 1-(1,2-benzoxazol-3-yl)-N,N-bis[(2,4-dimethoxyphenyl)methyl]ethane-1-sulfonamide)

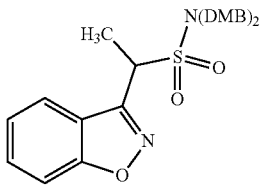

To a solution of the compound prepared in Reference example 9 (4.69 g) in THF (40 mL) was added n-butyllithium (1.55 mol/L hexane solution, 7.1 ml) under nitrogen atmosphere at −78° C., and then the mixture was stirred at the same temperature for one hour. Methyl iodide (0.63 mL) was added slowly to the reaction mixture at −78° C., and then the reaction mixture was warmed slowly to room temperature and stirred for 12 hours. Saturated aqueous ammonium chloride was added to the reaction mixture, and the mixture was extracted with ethyl acetate. The organic layer was washed with brine, and dried over anhydrous sodium sulfate. The solvent was removed under reduced pressure, and the obtained residue was purified by silica gel column chromatography (n-hexane:ethyl acetate; 2:1) to give the title compound (4.26 g) as an oil $^1$H-NMR (CDCl$_3$) δ: 1.81 (d, 3H), 3.74 (s, 6H), 3.77 (s, 6H), 4.20 (d, 2H), 4.33 (d, 2H), 4.60 (q, 1H), 6.36-6.40 (m, 4H), 7.16 (d, 2H), 7.26-7.30 (m, 1H), 7.49-7.55 (m, 2H), 7.98 (d, 1H)

Reference Examples 14-21

Each compound shown in Table 4 was prepared from each corresponding starting compound in similar reaction and treatment to the method described in Reference example 13.

TABLE 4

| Reference example | Structure |
|---|---|
| 14 | ![structure] |
| 15 | ![structure] |
| 16 | ![structure] |
| 17 | ![structure] |
| 18 | ![structure] |

TABLE 4-continued

| Reference example | Structure |
|---|---|
| 19 | H₃C, N(DMB)₂ on 5-fluorobenzo[d]isoxazol-3-yl sulfonamide |
| 20 | H₃C, N(DMB)₂ on 5-chlorobenzo[d]isoxazol-3-yl sulfonamide |
| 21 | H₃C-O-C(=O)-CH₂-CH(SO₂N(DMB)₂)-benzo[d]isoxazol-3-yl |

Reference Example 22

1-(Benzo[d]isoxazol-3-yl)-N,N-bis(2,4-dimethoxy-benzyl)-1-fluoromethanesulfonamide (IUPAC Name: 1-(1,2-benzoxazol-3-yl)-N,N-bis[((2,4-dimethoxyphenyl)methyl]-1-fluoromethanesulfonamide)

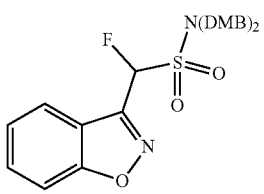

To a solution of the compound prepared in Reference example 9 (2.00 g) in THF (30 mL) was added sodium bis(trimethylsilyl)amide (1.0 mol/l THF solution, 4.29 mL) at −78° C. under nitrogen stream, and the mixture was stirred at 0° C. for 20 minutes. The reaction mixture was cooled again to −78° C., and a solution of N-fluorobenzenesulfonimide (1.29 g) in THF (15 mL) was added dropwise to the reaction mixture. The reaction mixture was warmed slowly to room temperature, and stirred for 12 hours. Saturated aqueous sodium bicarbonate was added to the reaction mixture, and the mixture was extracted with ethyl acetate. The organic layer washed with brine, dried over anhydrous sodium sulfate, and concentrated under reduced pressure. The obtained residue was purified by silica gel column chromatography (n-hexane:ethyl acetate; 1:1) to give the title compound (1.98 g) as an oil.

¹H-NMR (CDCl₃) δ: 3.80 (s, 6H), 3.82 (s, 6H), 4.32 (d, 2H), 4.61 (d, 2H), 6.22 (d, 1H), 6.45-6.47 (m, 4H), 7.20 (d, 2H), 7.32-7.36 (m, 1H), 7.53-7.61 (m, 2H), 8.01 (d, 1H)

Reference Examples 23-24

Each compound shown in Table 5 was prepared from each corresponding starting compound in similar reaction and treatment to the method described in Reference example 22.

TABLE 5

| Reference example | Structure |
|---|---|
| 23 | F,F-difluoro-benzo[d]isoxazol-3-yl-CH(SO₂N(DMB)₂) |
| 24 | H₃C, F-benzo[d]isoxazol-3-yl-C(SO₂N(DMB)₂) |

Reference Example 25

1-(Benzo[d]isoxazol-3-yl)-N,N-bis(2,4-dimethoxy-benzyl)-3-hydroxypropane-1-sulfonamide (IUPAC Name: 1-(1,2-benzoxazol-3-yl)-N,N-bis[(2,4-dimethoxyphenyl)methyl]-3-hydroxypropane-1-sulfonamide)

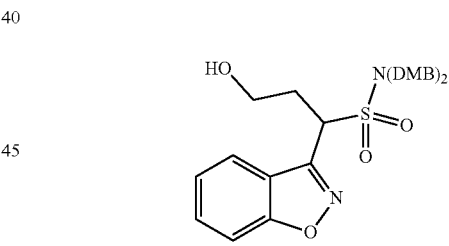

To a solution of the compound prepared in Reference example 21 (4.64 g) in THF (50 mL) was added lithium aluminium hydride (1 mol/l THF solution, 7.94 mL) at 0° C. under nitrogen stream, and the mixture was stirred at the same temperature for one hour. Saturated aqueous sodium sulfate was added to the reaction mixture to deactivate the reducing agent, and the precipitated solid was removed by Celite filtration. The filtrate was concentrated under reduced pressure, and the obtained residue was purified by silica gel column chromatography (eluting solvent; n-hexane:ethyl acetate; 1:19) to give the title compound (3.13 g) as an amorphous.

¹H-NMR (CDCl₃) δ: 2.44-2.53 (m, 1H), 2.56-2.65 (m, 1H), 3.65-3.70 (m, 1H), 3.74 (s, 6H), 3.76 (s, 6H), 4.18 (d, 2H), 4.24 (d, 2H), 4.78 (dd, 1H), 6.36-6.39 (m, 4H), 7.14 (d, 2H), 7.28 (ddd, 1H), 7.49-7.56 (m, 2H), 7.95 (d, 1H)

Reference Example 26

1-(Benzo[d]isoxazol-3-yl)-3-chloro-N,N-bis(2,4-dimethoxybenzyl)propane-1-sulfonamide (IUPAC Name: 1-(1,2-benzoxazol-3-yl)-3-chloro-N,N-bis[(2,4-dimethoxyphenyl)methyl]propane-1-sulfonamide)

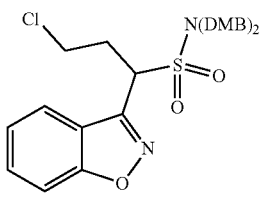

To a solution of the compound prepared in Reference example 25 (3.13 g) in dichloromethane (30 mL) was added 1-chloro-N,N,2-trimethylpropenylamine (1.12 mL) under nitrogen stream, and the mixture was stirred at room temperature for 2 hours. The solvent was removed under reduced pressure, and the obtained residue was purified by silica gel column chromatography (eluting solvent; n-hexane:ethyl acetate; 1:1) to give the title compound (3.12 g) as an oil.

$^1$H-NMR (CDCl$_3$) δ: 2.72-2.79 (m, 2H), 3.16-3.22 (m, 1H), 3.50-3.55 (m, 1H), 3.76 (s, 6H), 3.77 (s, 6H), 4.21 (d, 2H), 4.25 (d, 2H), 4.71 (dd, 1H), 6.38-6.42 (m, 4H), 7.16 (d, 2H), 7.29 (ddd, 1H), 7.50-7.57 (m, 2H), 7.86 (d, 1H)

Reference Example 27

1-(Benzo[d]isoxazol-3-yl)-N,N-bis(2,4-dimethoxybenzyl)cyclopropane-1-sulfonamide (IUPAC Name: 1-(1,2-benzoxazol-3-yl)-N,N-bis[(2,4-dimethoxyphenyl)methyl]cyclopropane-1-sulfonamide)

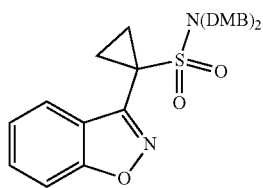

To a solution of the compound prepared in Reference example 26 (3.12 g) in THF (50 mL) was added n-butyllithium (2.65 mol/L hexane solution, 2.5 mL) at −78° C. under nitrogen atmosphere, and the mixture was warmed to room temperature over one hour. The mixture was stirred at room temperature overnight. Saturated aqueous ammonium chloride was added to the reaction mixture, and the mixture was extracted with ethyl acetate. The organic layer was washed with brine, and dried over anhydrous sodium sulfate. The solvent was removed under reduced pressure, and the obtained residue was purified by silica gel column chromatography (n-hexane:ethyl acetate; 1:1) to give the title compound (2.86 g) as an amorphous.

$^1$H-NMR (CDCl$_3$) δ: 1.40 (dd, 2H), 1.81 (dd, 2H), 3.60 (s, 6H), 3.71 (s, 6H), 4.18 (s, 4H), 6.18 (d, 2H), 6.24 (dd, 2H), 7.09 (d, 2H), 7.30-7.35 (m, 1H), 7.49-7.54 (m, 2H), 8.06 (d, 1H)

Example 1

1-(Benzo[d]isoxazol-3-yl)ethane-1-sulfonamide (IUPAC Name: 1-(1,2-benzoxazol-3-yl)ethane-1-sulfonamide)

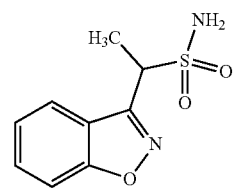

To a solution of the compound prepared in Reference example 13 (4.26 g) in toluene (30 mL) was added trifluoroacetic acid (20 mL), and the mixture was stirred at room temperature for 3 hours. The reaction solution was concentrated under reduced pressure, and ethyl acetate (100 mL) was added to the obtained residue. The mixture was stirred and the insoluble matter was removed by filtration. The filtrate was concentrated under reduced pressure, and the obtained residue was purified by silica gel column chromatography (n-hexane:ethyl acetate; 1:1) to give the title compound (1.16 g) as a solid.

$^1$H-NMR (DMSO-d$_6$) δ: 1.81 (d, 3H), 4.92 (q, 1H), 7.17 (s, 2H), 7.38-7.42 (m, 1H), 7.63-7.67 (m, 1H), 7.74-7.76 (m, 1H), 7.96-7.98 (m, 2H)

MS (m/z) 225 (MH−), Rt=0.50 min.

Examples 2-12

Each compound shown in Table 6 was prepared from each corresponding starting compound in a similar reaction and treatment to the method described in Example 1.

TABLE 6

| Example | Structure | $^1$H-NMR δ: | LC-MS [M − H]$^-$/Rt |
|---|---|---|---|
| 2 | H$_3$C, H$_3$C structure with NH$_2$, S=O, benzoxazole | CDCl3: 2.08 (s, 6H), 4.51 (s, 2H), 6.74 (br s, 1H), 7.34-7.38 (m, 1H), 7.55-7.63 (m, 2H), 8.03 (d, 2H) | 239/0.57 min |

TABLE 6-continued

| Example | Structure | ¹H-NMR δ: | LC-MS [M − H]⁻/Rt |
|---|---|---|---|
| 3 | 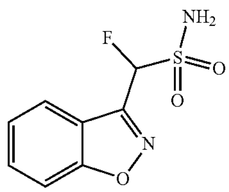 [SMILES: NS(=O)(=O)C(F)c1noc2ccccc12] | DMSO-d6: 7.00 (d, 1H), 7.48 (dd, 1H), 7.73 (dd, 1H), 7.62-7.65 (m, 2H), 7.86 (d, 1H), 7.87 (s, 2H), 7.92 (d, 1H) | 229/0.54 min |
| 4 | 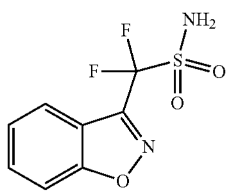 [SMILES: NS(=O)(=O)C(F)(F)c1noc2ccccc12] | DMSO-d6: 7.56 (d, 1H), 7.78-7.83 (m, 1H), 7.87 (d, 1H), 7.96 (d, 1H), 8.55 (br s, 2H) | 247/0.64 min |
| 5 | 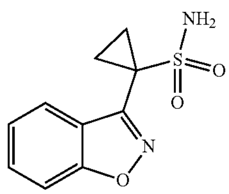 [SMILES: NS(=O)(=O)C1(c2noc3ccccc23)CC1] | DMSO-d6: 1.40-1.51 (m, 2H), 1.65-1.75 (m, 2H), 7.22 (br s, 2H), 7.41-7.45 (m, 1H), 7.64-7.68 (m, 1H), 7.76 (d, 1H), 7.98 (d, 1H) | 237/0.54 min |
| 6 | 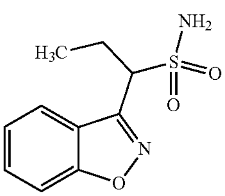 [SMILES: CCC(c1noc2ccccc12)S(N)(=O)=O] | DMSO-d6: 0.84 (t, 3H), 2.26-2.42 (m, 2H), 4.66 (dd, 1H), 7.18 (br s, 2H), 7.40 (dd, 1H), 7.66 (dd, 1H), 7.77 (d, 1H), 7.97 (d, 1H) | 239/0.58 min |
| 7 | 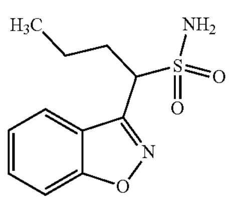 [SMILES: CCCC(c1noc2ccccc12)S(N)(=O)=O] | CDCl₃: 0.93 (t, 3H), 1.31-1.40 (m, 2H), 2.42-2.48 (m, 2H), 4.60 (br s, 2H), 4.71 (dd, 1H), 7.36 (ddd, 1H), 7.56-7.62 (m, 2H), 7.88 (d, 1H) | 253/0.68 min |
| 8 | 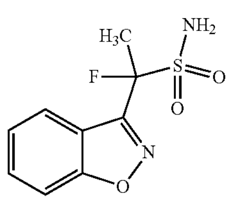 [SMILES: CC(F)(c1noc2ccccc12)S(N)(=O)=O] | DMSO-d6: 2.21 (d, 3H), 7.46 (dd, 1H), 7.70 (ddd, 1H), 7.81 (br s, 2H), 7.83 (d, 1H), 7.92 (d, 1H) | 243/0.59 min |
| 9 | 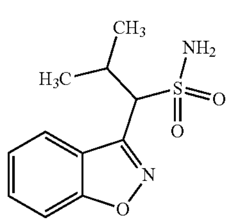 [SMILES: CC(C)C(c1noc2ccccc12)S(N)(=O)=O] | CDCl₃: 0.91 (d, 3H), 1.29 (d, 3H), 2.82-2.94 (m, 1H), 4.51 (d, 1H), 4.51 (br s, 2H), 7.31 (ddd, 1H), 7.52-7.58 (m, 2H), 7.88 (d, 1H) | 253/0.66 min |

TABLE 6-continued

| Example | Structure | $^1$H-NMR δ: | LC-MS [M − H]$^-$/Rt |
|---|---|---|---|
| 10 | (structure: 5-methoxy benzo[d]isoxazole with CH(CH$_3$)SO$_2$NH$_2$) | DMSO-d6: 1.79 (d, 3H), 3.80 (s, 3H), 4.89 (q, 1H), 7.14 (br s, 2H), 7.26 (dd, 1H), 7.39 (d, 1H), 7.66 (d, 1H) | 255/0.56 min |
| 11 | (structure: 5-fluoro benzo[d]isoxazole with CH(CH$_3$)SO$_2$NH$_2$) | DMSO-d6: 1.79 (d, 3H), 3.80 (s, 3H), 4.89 (q, 1H), 7.14 (br s, 2H), 7.26 (dd, 1H), 7.39 (d, 1H), 7.66 (d, 1H) | 243/0.55 min |
| 12 | (structure: 5-chloro benzo[d]isoxazole with CH(CH$_3$)SO$_2$NH$_2$) | DMSO-d6: 1.79 (d, 3H), 4.97 (q, 1H), 7.17 (br s, 2H), 7.70 (dd, 1H), 7.78 (d, 1H), 8.02 (d, 1H) | 259/0.64 min |

Examples 13 and 14

(R)-1-(Benzo[d]isoxazol-3-yl)ethane-1-sulfonamide (IUPAC Name: (1R)-1-(1,2-benzoxazol-3-yl)ethane-1-sulfonamide) and (S)-1-(benzo[d]isoxazol-3-yl)ethane-1-sulfonamide (IUPAC Name: (1S)-1-(1,2-benzoxazol-3-yl)ethane-1-sulfonamide)

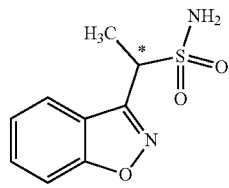

The compound prepared in Example 1 was divided with DAICEL CHIRALPAK™ AY-H (mobile phase: 100% acetonitrile), and the anterior peak (enantiomer A, undetermined absolute configuration) and posterior peak (enantiomer B, undetermined absolute configuration) were obtained.

Example 13 (enantiomer A): Retention time 3.46 min, Chiral HPLC (Chiralpak™ AY-H, 0.46 cm I.D.×25 cm L, Mobile phase: 100% acetonitrile, Flow rate: 1.0 mL/min, Temperature: 40° C., Wave length: 238 nm)

Example 14 (enantiomer B): Retention time 4.15 min, Chiral HPLC (Chiralpak™ AY-H, 0.46 cm I.D.×25 cm L, Mobile phase: 100% acetonitrile, Flow rate: 1.0 mL/min, Temperature: 40° C., Wave length: 238 nm)

The specific rotation of the compounds of Example 13 and Example 14 was measured according to the following condition.
Instrument: JASCO P-1020 Polarimeter
Temperature: 21.6° C.
Solution volume: 10 mg/mL
Analysis solvent: MeOH
Wave length: 589 nm
Cell length: 50 mm
Example 13 (enantiomer A): specific rotation −30.1886
Example 14 (enantiomer B): specific rotation +31.4743

Example 15

X-Ray Crystal Structure Analysis of Single-Crystal Example 13

For determining crystalline structure, single-crystal X-ray diffraction analysis of a single crystal of Example 13 was carried out with a diffractometer (pinpoint structural measurement system) at −173° C.

Preparation of Single Crystal

Example 13 (0.01-0.03 g) was put into a glass screw tube bottle, tetrahydrofuran (about 0.02 mL) was added thereto. The screw tube bottle was capped, and the suspension was shaken at about 50° C. for about 10 days to obtain a single crystal of Example 13.

Single-Crystal X-Ray Crystal Structure Analysis

The single crystal of Example 13 was fixed in the diffractometer, and measured about its diffraction image with X-ray having a given wavelength under a stream of inert gas at −173° C. From a set of plane index and diffraction intensity calculated from the diffraction image, the structure was determined by the direct method and the structure was refined by the least square method [Acta Cryst. A64, 112 (2008)] to obtain a molecular structure thereof and a crystal structure thereof. The result of the X-ray crystal structure analysis showed that the absolute configuration at a position of the benzoxazol in the compound of Example 13 (enantiomer A having specific rotation of −30.1886) is R. The analytical results are shown in Table 7, FIG. 1-1, and FIG. 1-2.

TABLE 7

| | |
|---|---|
| Empirical formula | C9H10N2O3S |
| Molecular weight | 226.25 |
| Crystal system | orthorhombic |
| Space group | P2₁2₁2₁ |
| Lattice parameters: | |
| a | 7.98090(10) Å |
| b | 10.34330(10) Å |
| c | 11.97180(10) Å |
| Unit cell volume | 988.258(18) Å³ |
| Formula units per unit | 4 |
| $R_{int}$ | 5.85% |
| Number of parameters | 160 |
| Number of restraints | 210 |
| R1 | 4.45% |
| wR2 | 11.64% |
| GooF S | 1.120 |
| Flack parameters | 0.02 (4) |

Example 16

Preparation of (1R)-1-(1,2-benzoxazol-3-yl)ethane-1-sulfonamide (Alternative Process for Example 13)

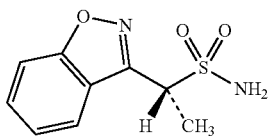

The title compound was prepared as shown in the following processes.

(i) Propan-2-yl (1,2-benzoxazol-3-yl)methanesulfonate

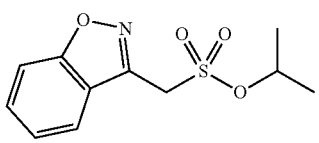 [SMILES: CC(C)OS(=O)(=O)Cc1noc2ccccc12]

To a solution of (1,2-benzoxazol-3-yl)methanesulfonic acid (13.00 g) in acetonitrile (130 ml) were added silver oxide (16.96 g) and 2-iodopropane (7.32 ml), and the mixture was stirred at room temperature for one hour. The insoluble matter was removed on Celite, and the filtrate was concentrated. The obtained residue was purified by silica gel chromatography (hexane:ethyl acetate; 19:1→1:1) to give the title compound (13.00 g) as a yellow solid. Yield: 84%.

¹H NMR (400 Hz, CDCl₃) δ 1.34 (d, J=6.4 Hz, 6H), 4.75 (s, 2H), 4.85 (dt, J=12.8, 6.4 Hz, 1H), 7.38 (t, J=8.0, 6.0, 2.4 Hz, 1H), 7.56-7.62 (m, 2H), 7.90 (d, J=8.0 Hz, 1H),

(ii) Propan-2-yl 1-(1,2-benzoxazol-3-yl)ethane-1-sulfonate

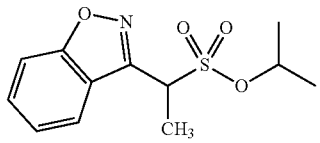 [SMILES: CC(C)OS(=O)(=O)C(C)c1noc2ccccc12]

To a solution of the compound (13.00 g, 50.9 mmol) prepared in Step (i) of Example 16 in THF (255 ml) was added sodium hydride (2.222 g, 50.9 mmol) at 0° C., and the mixture was stirred at the same temperature for 10 minutes. Methyl iodide (3.80 ml, 61.1 mmol) was added to the reaction mixture, and the mixture was stirred at 0° C. for one hour. The reaction solution was quenched with saturated aqueous ammonium chloride, and the mixture was extracted with ethyl acetate. The organic layer was washed with brine, dried over sodium sulfate, and concentrated. The obtained residue was purified by silica gel chromatography (hexane:ethyl acetate; 19:1→3:1) to give the title compound (10.60 g) as a yellow oil. Yield: 77%.

¹H NMR (400 Hz, CDCl₃) δ 1.20 (d, J=6.2 Hz, 3H), 1.27 (d, J=6.2 Hz, 3H), 1.95 (d, J=7.2 Hz, 3H), 4.72 (sep, 6.2 Hz, 2H), 4.82 (q, J=7.2 Hz, 1H), 7.27-7.32 (m, 1H), 7.49-7.55 (m, 2H), 7.89 (d, J=8.0 Hz, 1H), MS(m/z): 270.2 [M+1]+, Rt=0.99 min.

(iii) Sodium 1-(1,2-benzoxazol-3-yl)ethane-1-sulfonate

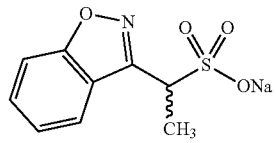

To a solution of the compound (7.80 g, 29.0 mmol) prepared in Step (ii) of Example 16 in acetone (250 ml) was added sodium iodide (4.34 g, 29.0 mmol), and the mixture was heated under reflux for 4 hours. A white precipitate was collected on a filter and washed with acetone to give the title compound (6.60 g, 91% yield) as a white solid.

¹H NMR (400 Hz, DMSO-d₆) δ 1.65 (d, J=7.2 Hz, 3H), 4.22 (q, J=7.2 Hz, 1H), 7.31 (t, J=7.4 Hz, 1H), 7.57 (dt, J=8.8, 1.2 Hz, 1H), 765 (d, J=8.8 Hz, 1H), 8.09 (d, J=8.0 Hz, 1H) MS(m/z): 228.1 [M−21]+, Rt=0.48 min.

(iii-a) Sodium 1-(1,2-benzoxazol-3-yl)ethane-1-sulfonate (Alternative Process for Step (iii) Example 16)

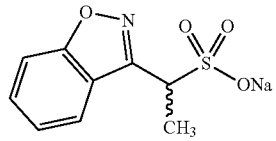

3-(1-Bromoethyl)-1,2-benzoxazole (226 mg), sodium sulfite (189 mg), and potassium iodide (17 mg) were suspended in THF (0.5 mL) and water (1 mL), and the suspension was stirred at 50° C. for 80 hours. Cooling the reaction suspension, ethyl acetate (1 mL) was added to the reaction solution and the mixture was separated into two layers. The aqueous layer was concentrated to dryness to give the title compound (416 mg) as a mixture. Yield: 96%.

$^1$H NMR (400 Hz, DMSO-d6) δ 1.65 (d, J=7.2 Hz, 3H), 4.22 (q, J=7.2 Hz, 1H), 7.31 (t, J=7.4 Hz, 1H), 7.57 (dt, J=8.8, 1.2 Hz, 1H), 765 (d, J=8.8 Hz, 1H), 8.09 (d, J=8.0 Hz, 1H)

(iv) 1-(1,2-Benzoxazol-3-yl)ethane-1-sulfonyl chloride

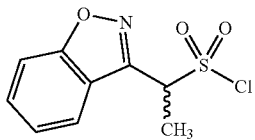

To a suspension of the compound (600 mg, 2.408 mmol) prepared in Step (iii) of Example 16 in THF (10 ml) were added thionyl chloride (0.210 ml, 2.89 mmol) and N,N-dimethylformamide (9.32 μl, 0.120 mmol), and the mixture was heated under reflux for 4 hours. After cooling the reaction mixture to room temperature, the mixture was diluted with ethyl acetate and washed with cold water three times. The organic layer was washed with brine, dried over sodium sulfate, and concentrated to give the title compound (606.00 mg, yield: 102%) as a brown oil.

MS(m/z): 246.1 [M+1]+, Rt=1.00 min.

(v) (1R)-1-(1,2-Benzoxazol-3-yl)-N-[(1S,2S)-2-hydroxy-2,3-dihydro-1H-inden-1-yl]ethane-1-sulfonamide

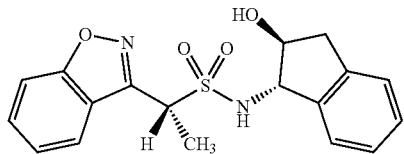

To a solution of (1S,2S)-(+)-trans-1-amino-2-indanol (359 mg, 2.406 mmol) and N,N-diisopropylethylamine (0.880 ml) in acetonitrile (10 ml) was added a solution of the compound (591 mg, 2.406 mmol) prepared in Step (iv) of Example 16 in acetonitrile (10 ml), and the mixture was stirred at room temperature for 15 hours. The reaction mixture was diluted with 10% aqueous citric acid and extracted with ethyl acetate. The organic layer was washed with brine, dried over sodium sulfate, and concentrated. The obtained residue was purified by silica gel column chromatography (hexane:ethyl acetate; 19:1→1:1) to give the title compound (174 mg, yield: 20.18%) as a white solid and its diastereomer, (1S)-1-(1,2-benzoxazol-3-yl)-N-[(1S,2S)-2-hydroxy-2,3-dihydro-1H-inden-1-yl]ethane-1-sulfonamide (192.00 mg, yield: 22.27%).

(1R)-1-(1,2-benzoxazol-3-yl)-N-[(1S,2S)-2-hydroxy-2,3-dihydro-1H-inden-1-yl]ethane-1-sulfonamide $^1$H NMR (400 Hz, CDCl$_3$) δ 2.10 (d, J=7.2 Hz, 3H), 2.89 (dd, J=15.2, 9.2 Hz, 1H), 3.20 (dd, J=16.0, 8.0 Hz, 1H), 4.27-4.35 (m, 1H), 4.36 (d, 9.6 Hz, 1H), 4.63 (d, 3.6 Hz, 1H), 4.74 (dd, J=9.6, 7.2 Hz, 1H), 5.14 (q, J=7.2 Hz, 1H), 7.13-7.17 (m, 1H), 7.21-7.24 (m, 2H), 7.32-7.35 (m, 1H), 7.38-7.42 (m, 1H), 7.62 (d, J=3.6 Hz, 2H), 8.03 (dd, J=9.2, 1.2 Hz, 1H)

MS(m/z): 359.2 [M+1]+, Rt=0.92 min.

(1S)-1-(1,2-benzoxazol-3-yl)-N-[(1S,2S)-2-hydroxy-2,3-dihydro-1H-inden-1-yl]ethane-1-sulfonamide $^1$H NMR (400 Hz, CDCl$_3$) δ 2.13 (d, J=7.2 Hz, 3H), 2.84 (dd, J=16.0, 8.0 Hz, 1H), 3.24 (dd, J=16.0, 8.0 Hz, 1H), 3.59 (d, 3.2 Hz, 1H), 4.36-4.42 (m, 1H), 4.48 (d, J=9.2 Hz, 1H), 4.62 (dd, J=8.8, 6.8 Hz, 1H), 5.07 (q, 7.2 Hz, 1H), 7.15-7.19 (m, 1H), 7.22-7.30 (m, 3H), 7.38-7.42 (m, 1H), 7.59-7.65 (m, 2H), 7.97-8.00 (m, 1H)

MS(m/z): 359.2 [M+1]+, Rt=0.90 min.

(vi) (1R)-1-(1,2-Benzoxazol-3-yl)ethane-1-sulfonamide

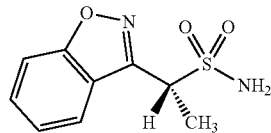

To a suspension of the compound (51 mg, 0.142 mmol) prepared in Step (v) of Example 16 in toluene (1 ml) was added trifluoromethanesulfonic acid (0.252 ml, 2.85 mmol) at 0° C., and the mixture was stirred at 0° C. for 0.5 hours. Acetonitrile (1 mL) was added to the reaction mixture, and the mixture was diluted with ethyl acetate and separated into two layers. The organic layer was washed with water three times, dried over magnesium sulfate, and concentrated. The obtained residue was purified by silica gel column chromatography (hexane:ethyl acetate; 19:1→1:1) to give the title compound (27.50 mg, yield: 85%, >99% ee) as a white solid.

Example 17

Preparation of (1R)-1-(1,2-benzoxazol-3-yl)ethane-1-sulfonamide (Alternative Process for Example 13)

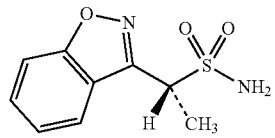

The title compound was prepared as shown in the following processes.

(i) 1-(1,2-Benzoxazol-3-yl)ethyl acetate

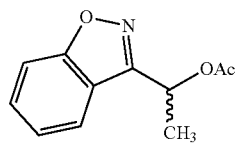

To a mixture of 3-(1-bromoethyl)-1,2-benzoxazole (4.52 g), sodium acetate (3.28 g), and potassium iodide (3.32 g) was added DMF (20 mL), and the mixture was stirred at 50° C. for 14 hours. The reaction solution was cooled, then a solution of sodium thiosulfate pentahydrate (2 g) in water (40 g) was added to the reaction solution, and the mixture was extracted with ethyl acetate (40 mL). The aqueous layer was extracted with ethyl acetate (20 mL) twice, ant the combined organic layer was washed with a solution of sodium thiosulfate 5 hydrate (1 g) in water (20 g). The organic layer was dried over sodium sulfate, filtered, and concentrated. The concentrated residue was purified by silica gel column chromatography (hexane:ethyl acetate; 98:2→70:30) to give the title compound (3.72 g, yield: 91%) as a colorless oil.

$^1$H NMR (400 Hz, CDCl$_3$) δ 1.79 (d, J=6.8 Hz, 3H), 2.144 (s, 3H), 6.39 (q, J=6.8 Hz, 1H), 7.34 (ddd, J=8.0, 6.4, 1.6 Hz, 1H), 7.54-7.61 (m, 2H), 7.78 (d, J=8.8 Hz, 1H).

(ii) 1-(1,2-Benzoxazol-3-yl)ethan-1-ol

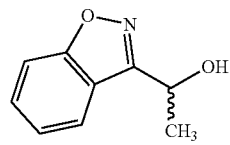

To a solution of the compound (1.54 g) prepared in Step (i) of Example 17 in methanol (15 mL) was added 1 N aqueous sodium hydroxide (7.5 mL) at ice temperature, and the mixture was stirred at room temperature for 4 hours. The reaction solution was concentrated to a certain volume, and then extracted with ethyl acetate (25 mL) three times. The organic layer was dried over sodium sulfate, filtered, and concentrated. The concentrated residue was purified by silica gel column chromatography (hexane:ethyl acetate; 98:2→70:30) to give the title compound (1.20 g) as a colorless oil. Yield: 98%.

$^1$H NMR (400 Hz, CDCl$_3$) δ 1.77 (d, J=6.4 Hz, 3H), 2.32 (d, J=4.8 Hz, 1H), 5.39 (ddd, J=13.6, 6.8, 4.8 Hz, 1H), 7.33 (ddd, J=8.0, 6.0, 2.0 Hz, 1H), 7.56-7.60 (m, 2H), 7.89 (dd, J=8.0, 1.2 Hz, 1H)

(iii) 1-(1,2-Benzoxazol-3-yl)ethan-1-one

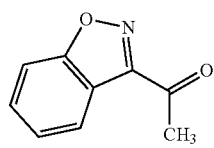

A solution of the compound (1.42 g) prepared in Step (ii) of Example 17 and manganese dioxide (7.58 g) in dichloromethane (20 g) was stirred at room temperature for 20 hours. The reaction solution was filtered through Celite, and the filtrate was concentrated to dryness to give the title compound (1.31 g, yield: 93%).

$^1$H NMR (400 Hz, CDCl$_3$) δ 2.81 (s, 3H), 7.41-7.469 (m, 1H), 7.58-7.67 (m, 2H), 8.24 (dd, J=8.0, 1.2 Hz, 1H)

(iv) (1S)-1-(1,2-Benzoxazol-3-yl)ethan-1-ol

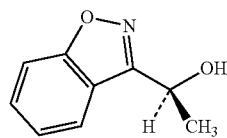

Sodium dihydrogenphosphate dihydrate (1.25 g), disodium hydrogen phosphate dodecahydrate (2.87 g), and magnesium sulfate (38 mg) were dissolved in deionized water (160 g) at room temperature. Codexis™ Ketoreductase (KRED P1-B05) (200 mg) and NADP$^+$ (80 mg) were added to the reaction mixture, and the mixture was dissolved by stirring at room temperature. A solution of the compound (10.00 g) prepared in Step (iii) of Example 17 in isopropyl alcohol (31.5 g) was added to the reaction solution, and the mixture was stirred at 35° C. for 41 hours. The reaction solution was concentrated to a certain volume, and chlorobenzene (200 g) was added to the concentrated solution. The mixture was filtered through Celite, and the filtrate was separated into two layers. The organic layer was washed with water (200 g), dried over sodium sulfate, filtered, and concentrated to give a mixture including the title compound (9.61 g) as a pale yellow oil. The mixture (1 g) was purified by silica gel column chromatography (hexane:ethyl acetate; 98:2→96:4) to give the title compound (901 mg) as a colorless oil. Yield: 85%, 99.3% ee.

(iv-a) (1S)-1-(1,2-Benzoxazol-3-yl)ethan-1-ol

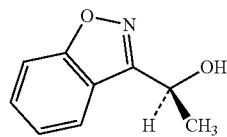

By using carbonyl reductase screening kit (CODEX™, CODEXIS), the reduction reaction of the compound prepared in Step (iii) of Example 17 was carried out with each combination 1-24 of the carbonyl reductase and the coenzyme shown in Table 8.

Carbonyl reductases 1-19 shown in Table 8 were treated by the following procedure. A solution of a coenzyme mixture (128 mM sodium phosphate, 1.7 mM magnesium sulfate, 1.1 mM NADP$^+$, pH 7.0) (0.6 g) in deionized water (33 g) was prepared, and each 0.9 mL of the solution was added to carbonyl reductases 1-19 (10 mg). Each mixture was stirred to be dissolved. A solution of the compound (161 mg) prepared in Step (iii) of Example 17 in isopropyl alcohol (4 mL) was prepared, and each 0.1 mL of the solution was added to the above reaction media. Each reaction medium was stirred at 30° C. for 20 hours. Ethyl acetate was added to each reaction medium, and the mixture was centrifuged. The ethyl acetate layer was analyzed by HPLC.

Carbonyl reductases 20-24 shown in Table 8 were treated by the following procedure. A solution of a coenzyme mixture (263 mM sodium phosphate, 1.7 mM magnesium sulfate, 1.1 mM NADP+, 1.1 mM NAD+, 80 mM D-glucose, 4.3 U/mL glucose dehydrogenase, pH 7.0) (0.3 g) in deionized water (6 g) was prepared, and mixed with a solution of the compound (48 mg) prepared in Step (iii) of Example 17 in DMSO (0.3 mL). Each 1 mL of the mixture was added to carbonyl reductases 20-24 (10 mg), and each mixture was stirred at 30° C. for 20 hours. Ethyl acetate was added to each reaction medium, and the mixture was centrifuged. The ethyl acetate layer was analyzed by HPLC.

As shown in Table 8, it has been found that the compound prepared in Step (iii) of Example 17 can be enantioselectively reduced with a combination of carbonyl reductase (1-24) and coenzyme (NADPH or NADH).

TABLE 8

| | carbonyl reductase | coenzyme | Example 17 Step (iv-a) (S form) | Enantiomer of Example 17 Step (iv-a) (R form) |
|---|---|---|---|---|
| 1 | KRED-P1-A04 | NADPH | 2.8 | 97.2 |
| 2 | KRED-P1-A12 | NADPH | 8.9 | 91.1 |
| 3 | KRED-P1-B02 | NADPH | 36.5 | 63.5 |
| 4 | KRED-P1-B05 | NADPH | 99.2 | 0.8 |
| 5 | KRED-P1-B10 | NADPH | 62.9 | 37.1 |
| 6 | KRED-P1-B12 | NADPH | 29.5 | 70.5 |
| 7 | KRED-P1-C01 | NADPH | 85.6 | 14.4 |
| 8 | KRED-P1-H08 | NADPH | 97.1 | 2.9 |
| 9 | KRED-P2-B02 | NADPH | 97 | 3.0 |
| 10 | KRED-P2-C02 | NADPH | 60.4 | 39.6 |
| 11 | KRED-P2-C11 | NADPH | 34 | 66.0 |
| 12 | KRED-P2-D03 | NADPH | 92.6 | 7.4 |
| 13 | KRED-P2-D11 | NADPH | 98.8 | 1.2 |
| 14 | KRED-P2-D12 | NADPH | 92 | 8.0 |
| 15 | KRED-P2-G03 | NADPH | 66.3 | 33.7 |
| 16 | KRED-P2-H07 | NADPH | 4.5 | 95.5 |
| 17 | KRED-P3-B03 | NADPH | 98.5 | 1.5 |
| 18 | KRED-P3-G09 | NADPH | 96.4 | 3.6 |
| 19 | KRED-P3-H12 | NADPH | 97.7 | 2.3 |
| 20 | KRED-101 | NADPH | 4.9 | 95.1 |
| 21 | KRED-119 | NADPH | 99.1 | 0.9 |
| 22 | KRED-130 | NADPH | 100 | 0.0 |
| 23 | KRED-NADH-101 | NADH | 100 | 0.0 |
| 24 | KRED-NADH-110 | NADH | 1.5 | 98.5 |

(iv-b) (1S)-1-(1,2-Benzoxazol-3-yl)ethan-1-ol (Alternative Process for Step (iv) of Example 17)

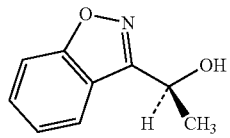

To the compound (3.50 g) prepared in Step (i) of Example 17 were added a phosphate buffer solution (pH 7.0) (35 mL) and Novozym 435 (0.70 g), and the mixture was stirred at 37° C. for 7 hours. The reaction solution was filtered, and the filtrate was extracted with ethyl acetate (70 mL, 35 mL×2). The combined organic layer was dried over sodium sulfate, filtered, and concentrated. The concentrated residue was purified by silica gel column chromatography (hexane:ethyl acetate; 98:2→70:30) to give the title compound (1.37 g, yield: 49%, 99.1% ee) as a colorless oil, together with (R)-1-(1,2-benzoxazol-3-yl)ethyl acetate (1.74 g, yield: 50%, 97.4% ee) as a colorless oil.

$^1$H NMR (400 Hz, CDCl$_3$) δ 1.77 (d, J=6.4 Hz, 3H), 2.32 (d, J=4.8 Hz, 1H), 5.39 (ddd, J=13.6, 6.8, 4.8 Hz, 1H), 7.33 (ddd, J=8.0, 6.0, 2.0 Hz, 1H), 7.56-7.60 (m, 2H), 7.89 (dd, J=8.0, 1.2 Hz, 1H)

(v) 3-{(1R)-1-[(1,3-Benzothiazol-2-yl)sulfanyl]ethyl}-1,2-benzoxazole

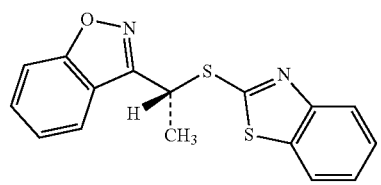 [SMILES: C[C@@H](Sc1nc2ccccc2s1)c1noc2ccccc12]

To a suspension of the compound (979 mg) prepared in Step (iv) or (iv-b) of Example 17 and dibenzothiazolyl disulfide (2.39 g) in THF (20 mL) was added dropwise tri-n-butylphosphine (1.78 mL) at ice temperature over 10 minutes, and the mixture was stirred at room temperature for 2 hours. To the reaction mixture were added ethyl acetate (50 mL) and 5% aqueous sodium bicarbonate (50 mL), and the mixture was separated into two layers. The aqueous layer was extracted with ethyl acetate (50 mL) twice, and the combined organic layer was washed with 5% aqueous sodium bicarbonate (50 mL). The organic layer was dried over sodium sulfate, filtered, and concentrated. The concentrated residue was purified by silica gel column chromatography (hexane:ethyl acetate; 98:2→82:18) to give the title compound (1.873 g) as colorless gum-like product. Yield: 100%, 98.0% ee.

$^1$H NMR (400 Hz, CDCl$_3$) δ 2.07 (d, J=6.4 Hz, 1H), 5.74 (q, J=7.2 Hz, 1H), 7.28-7.35 (m, 2H), 7.44 (dt, J=7.6, 1.2 Hz, 1H), 7.52-7.60 (m, 2H), 7.76 (d, J=8.0 Hz, 1H), 7.90 (dd, J=8.0, 1.2 Hz, 1H), 7.92 (d, J=8.0 Hz, 1H)

(vi) 3-[(1R)-1-(1,3-Benzothiazole-2-sulfonyl)ethyl]-1,2-benzoxazole

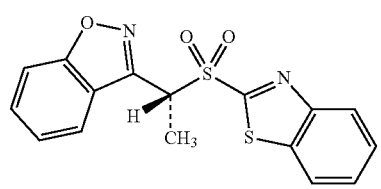 [SMILES: C[C@H](c1noc2ccccc12)S(=O)(=O)c1nc2ccccc2s1]

To a solution of the compound (250 mg) prepared in Step (v) of Example 17 in chlorobenzene (7.5 g) was added a solution of magnesium bis(monoperoxyphthalate) hexahydrate (0.95 g) in water (5 g), and the mixture was stirred at room temperature for 4 days. An additional solution of magnesium bis(monoperoxyphthalate) hexahydrate (0.24 g) in water (1.25 g) was added to the reaction mixture, and the mixture was stirred at room temperature for 8 hours. The reaction mixture was quenched by adding dropwise aqueous sodium bisulfite (0.24 g/l g) to the mixture at ice temperature. To the quenched mixture were added chlorobenzene (20 g) and water (20 g), and the mixture was separated into two layers. The organic layer was washed with a solution of potassium dihydrogenphosphate (272 mg) and dipotassium hydrogenphosphate (87 mg) in water (10 g), and then water (10 g). The organic layer was dried over sodium sulfate, filtered, and concentrated. The concentrated residue was slurry-washed with a mixture of chlorobenzene (2 g) and heptane (4 g), and the precipitated crystal was collected on a filter and washed with heptane (1 g). The obtained crystal was dried in vacuo at 40° C. to give the title compound (10.44 g) as a white crystal. Yield: 72%, 99.8% ee.

$^1$H NMR (400 Hz, CDCl$_3$) δ 2.11 (d, J=7.6 Hz, 1H), 5.37 (q, J=7.2 Hz, 1H), 7.33-7.37 (m, 1H), 7.56-7.60 (m, 3H), 7.62-7.66 (m, 1H), 7.91-7.97 (m, 2H) 8.24 (d, J=8.4 Hz, 1H)

(vii) (1R)-1-(1,2-Benzoxazol-3-yl)ethane-1-sulfonamide

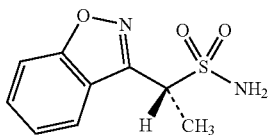

To a solution of magnesium chloride (0.69 g) in NMP (20 g) was added the compound (5.0 g) prepared in Step (vi) of Example 17 to give a suspension. The suspension was added dropwise to a suspension of sodium borohydride (1.10 g) in ethanol (22.5 g) at 0° C., and the rest of the suspension was dissolved in NMP (2.5 g) and added thereto. The mixture was reacted at 0° C. for 2 hours. The reaction solution was added dropwise to a solution of sodium acetate (11.91 g) and hydroxylamine-O-sulfonate (16.42 g) in water (62.5 g) at 0° C., and the rest of the reaction solution was dissolved in water (5 g) and added thereto. The mixture was reacted at 0° C. for 3.5 hours. To the reaction solution were added 6 M hydrochloric acid (25 g) and ethyl acetate (90 g), and the mixture was separated into two layers. The aqueous layer was extracted with ethyl acetate (45 g) twice, and the organic layer was washed with 1 M hydrochloric acid (90 g). To the organic layer was added activated charcoal (0.25 g), and the mixture was stirred for one hour. And, the mixture was filtered and the filtrate was concentrated. Ethyl acetate was added to the obtained residue to adjust the total amount to 22.5 g. The solution was crystallized by adding dropwise 20 g of heptane at 20° C. The solution including a crystal was cooled to 0° C., and the precipitated crystal was collected on a filter and washed with heptane-ethyl acetate mixture (5 g/2.5 g). The obtained crystal was dried in vacuo at 40° C. to give a crude crystal (2.40 g) as a yellowish white crystal.

To the crude crystal (2.0 g) was added isopropyl acetate (19.6 g), and the mixture was stirred at 50° C. for one hour, and then stirred at 10° C. for 3 hours. The insoluble matter was removed on a filter, and washed with isopropyl acetate (0.5 g). The filtrate was concentrated, and isopropyl acetate was added to the obtained residue to adjust the total amount to 4.4 g. The obtained suspension was stirred at 50° C. for 4 hours. The suspension was cooled to 0° C., and the precipitated crystal was collected on a filter and washed with isopropyl acetate (1.5 g). The obtained crystal was dried in vacuo at 40° C. to give the title compound (10.44 g) as a white crystal. Yield: 37.6%, 98.5% ee.

Example 18

Preparation of (1R)-1-(1,2-benzoxazol-3-yl)ethane-1-sulfonamide (Alternative Process for Example 13)

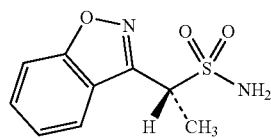

The title compound was prepared as shown in the following processes.

(i) 3-{(1R)-1-[(Pyrimidin-2-yl)sulfanyl]ethyl}-1,2-benzoxazole

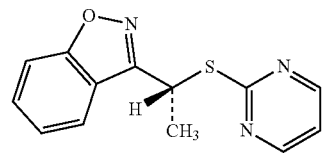 [SMILES: C[C@@H](Sc1ncccn1)c1noc2ccccc12]

To a solution of triphenylphosphine (531 mg) in toluene (1.5 mL) was added dropwise diisopropyl azodicarboxylate (90%, 420 μL) at 0° C., and the mixture was stirred at 0° C. for 15 minutes. A solution of the compound (245 mg) prepared in Step (iv) or (iv-a) of Example 17 in toluene (2 mL) wad added dropwise to the reaction mixture, and the mixture was stirred at 0° C. for 30 minutes. Pyrimidine-2-thiol (227 mg) was added to the reaction solution, and the mixture was stirred at 0° C. for 5 hours. The precipitated matter was removed on a filter, and the filtrate was concentrated under reduced pressure. The obtained residue was purified by silica gel column chromatography (hexane:ethyl acetate; 80:20→70:30) to give the title compound (290 mg). Yield: 75%, 100% ee.

$^1$H NMR (400 Hz, CDCl$_3$) δ 1.98 (d, J=7.2 Hz, 3H), 5.64 (q, J=7.2 Hz, 1H), 7.01 (t, J=5.0, 1H), 7.27-7.31 (m, 1H), 7.53-7.58 (m, 2H), 7.87 (dd, J=8.0, 1.2 Hz, 1H), 8.56 (d, J=5.2 Hz, 2H)

(ii) 3-[(1R)-1-(Pyrimidine-2-sulfonyl)ethyl]-1,2-benzoxazole

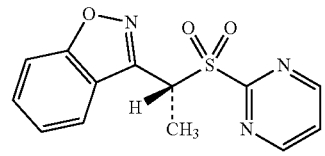 [SMILES: C[C@H](c1noc2ccccc12)S(=O)(=O)c1ncccn1]

To a solution of the compound (257 mg) prepared in Step (i) of Example 18 in dichloromethane (5 mL) was added m-chloroperbenzoic acid (542 mg) at ice temperature, and the mixture was stirred at room temperature for 5 hours. To the reaction mixture were added ethyl acetate (5 mL), and a solution of sodium thiosulfate pentahydrate (250 mg) and sodium bicarbonate (250 mg) in water (5 mL), and the mixture was separated into two layers. The aqueous layer was extracted with ethyl acetate (2 mL) twice, and the combined organic layer was washed with a solution of sodium thiosulfate pentahydrate (250 mg) and sodium bicarbonate (250 mg) in water (5 mL) twice. The organic layer was dried over sodium sulfate and concentrated. The obtained residue was purified by silica gel column chromatography (hexane:ethyl acetate; 80:20→20:80) to give the title compound (238 mg). Yield: 82%, 99.3% ee.

$^1$H NMR (400 Hz, CDCl$_3$) δ 2.08 (d, J=7.2 Hz, 3H), 5.57 (q, J=7.2 Hz, 1H), 7.38 (ddd, J=8.4, 6.4, 2.0 Hz 1H), 7.53-7.60 (m, 3H), 8.05 (d, J=8.0 Hz, 1H), 8.91 (d, J=4.8 Hz, 2H)

(iii) (1R)-1-(1,2-Benzoxazol-3-yl)ethane-1-sulfonamide

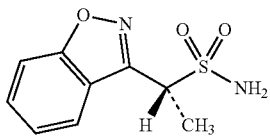

To a solution of the compound (28.9 mg) prepared in Step (ii) of Example 18 and magnesium chloride (28.6 mg) in DMF (300 μL) was added dropwise a solution of sodium borohydride (22.7 mg) in ethanol (300 μL) at 10° C., and the mixture was stirred at 20° C. for one hour, then cooled at 10° C. To the mixture were added sodium acetate (82 mg), and then dropwise a solution of hydroxylamine-O-sulfonic acid (113 mg) in water (600 μL), and the mixture was stirred at 20° C. for one hour. The reaction solution was added to 1 N hydrochloric acid (1.5 mL), and the mixture was extracted with ethyl acetate (3 mL). The organic layer was washed with 1 N hydrochloric acid (1.5 mL), dried over sodium sulfate, and concentrated. The obtained residue was purified by silica gel column chromatography (hexane/ethyl acetate 88/12-0-100) to give the title compound (17 mg) as a white crystal. Yield: 75%, 25.2% ee.

Example 19

Preparation of (1R)-1-(1,2-benzoxazol-3-yl)ethane-1-sulfonamide (Alternative Process for Example 13)

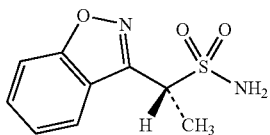

The title compound was prepared as shown in the following processes.

(i) 3-[(1R)-1-{[2-(Trimethylsilyl)ethyl]sulfanyl}ethyl]-1,2-benzoxazole

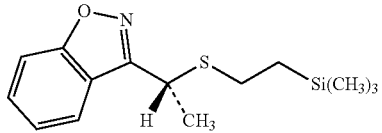

(i-1) To a solution of the compound (979 mg) prepared in Step (iv) or (iv-a) of Example 17 and N,N,N',N'-tetramethylazodicarboxamide (1550 mg) in THF (10 mL) was added thioacetic acid (0.67 mL), and the mixture was stirred. Under water-cooling, tri-n-butylphosphine (2.27 mL) was added dropwise to the reaction mixture, and the mixture was stirred at room temperature for 6 hours. The reaction mixture was diluted with water (25 mL), and extracted with ethyl acetate (25 mL) three times. The organic layer was dried over sodium sulfate and concentrated. The obtained residue was purified by silica gel column chromatography (hexane:ethyl acetate; 94:6→70:30) to give (R)—S-(1,2-benzoxazol-3-yl)ethyl thioacetate (285 mg). Yield: 21%, 99.6% ee.

$^1$H NMR (400 Hz, CDCl$_3$) δ 1.87 (d, J=7.2 Hz, 3H), 2.39 (s, 1H), 4.58 (quin, J=7.0 Hz, 1H), 7.34 (ddd, J=8.0, 6.0, 1.6 Hz 1H), 7.53-7.59 (m, 2H), 7.88 (dd, J=8.0, 1.2 Hz, 1H)

(i-2) To a solution of the compound (221 mg) prepared in Step (i-1) of Example 19 in methanol (2 mL) was added dropwise 1 N aqueous sodium hydroxide (1 mL), and the mixture was stirred at room temperature for 2 hours. The reaction solution was concentrated, and water (1 mL) was added to the obtained residue. 1 N Hydrochloric acid (1 mL) was added dropwise to the solution to adjust the pH of the solution to pH<3. The solution was extracted with ethyl acetate (4.5 mL) three times. The organic layer was washed with water (2 mL), dried over sodium sulfate, and concentrated. The obtained residue was purified by silica gel column chromatography (hexane:ethyl acetate; 94:6→70:30) to give (R)-1-(1,2-benzoxazol-3-yl)ethanethiol (140 mg). Yield: 78%.

$^1$H NMR (400 Hz, CDCl$_3$) δ 1.92 (d, J=6.8 Hz, 3H), 2.22 (d, J=7.2 Hz, 1H), 5.24 (q, J=3.2 Hz, 1H), 7.31 (ddd, J=8.0, 5.6, 1.6 Hz 1H), 7.53-7.59 (m, 2H), 7.71 (d, J=8.0 Hz, 1H)

(i-3) The compound (139 mg) prepared in Step (i-2) of Example 19, trimethylsilyl(vinyl)silane (93 mg), and 2,2'-azobis(isobutyronitrile)(AIBN) (2.6 mg) were mixed, and the mixture was stirred at 70° C. for 6 hours. Additional trimethylsilyl(vinyl)silane (93 mg) and AIBN (2.6 mg) were added to the reaction mixture, and the mixture was stirred at 70° C. for 2 hours. The reaction solution was purified by silica gel column chromatography (hexane:ethyl acetate; 98:2→82:18) to give the title compound (117 mg). Yield: 54%.

$^1$H NMR (400 Hz, CDCl$_3$) δ −0.06 (s, 9H), 0.69-0.77 (m, 1H), 0.83-0.91 (m, 1H), 1.80 (d, J=7.6 Hz, 3H), 2.37-2.48 (m, 2H), 4.45 (q, J=7.2 Hz, 1H), 7.31 (ddd, J=8.0, 6.0, 2.0 Hz 1H), 7.52-7.59 (m, 2H), 7.94 (dt, J=8.0, 1.2 Hz, 1H)

(ii) 3-{(1R)-1-[2-(Trimethylsilyl)ethanesulfonyl]ethyl}-1,2-benzoxazole

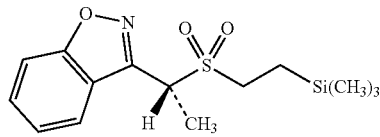

To a solution of the compound (112 mg) prepared in Step (i) of Example 19 in n-butanol-water (1 mL/1 mL) was added magnesium bis(monoperoxyphthalate) hexahydrate (476 mg) at ice temperature, and the mixture was stirred at room temperature for 5 hours. 1 M Aqueous sodium thiosulfate (2 mL) was added to the reaction mixture to quench the reaction, and the mixture was extracted with ethyl acetate (2 mL) three times. The organic layer was washed with 5% aqueous sodium bicarbonate (2 mL), dried over sodium sulfate, and concentrated. The obtained residue was purified by silica gel column chromatography (hexane:ethyl acetate; 98:2→70:30) to give the title compound (126 mg), Yield: 100%, 93.1% ee.

$^1$H NMR (400 Hz, CDCl$_3$) δ −0.01 (s, 9H), 0.92-1.11 (m, 2H), 2.01 (d, J=7.2 Hz, 3H), 2.78-2.90 (m, 2H), 4.86 (q, J=7.2 Hz, 1H), 7.38 (ddd, J=8.0, 6.0, 2.0 Hz 1H), 7.58-7.64 (m, 2H), 7.99 (d, J=8.0 Hz, 1H)

(iii) (1R)-1-(1,2-benzoxazol-3-yl)ethane-1-sulfonamide

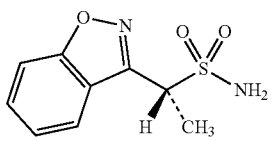

To a solution of the compound (31.1 mg) prepared in Step (ii) of Example 19 in THF (300 μL) was added 1 mol/L tetrabutylammonium fluoride (300 μL) at 10° C., and the mixture was stirred at 20° C. for 5 hours. The mixture was cooled to 10° C., and sodium acetate (41 mg) was added to the mixture. A solution of hydroxylamine-O-sulfonic acid (57 mg) in water (600 μL) was added dropwise to the mixture, and the mixture was stirred at 20° C. for 2 hours. To the reaction solution was added water (3 mL), and the mixture was extracted with ethyl acetate (3 mL) three times. The organic layer was dried over sodium sulfate and concentrated. The obtained residue was purified by silica gel column chromatography (hexane:ethyl acetate; 88/12→0:100) to give the title compound (13 mg) as a white crystal. Yield: 58%, 0% ee.

Example 20

Preparation of Example 13 Form I

The compound prepared in Example 1 was divided with DAICEL CHIRALPAK™ AY-H (mobile phase: 100% acetonitrile), and the obtained solution of Example 13 in acetonitrile was concentrated to isolate form I of the compound of Example 13. The product was characterized as mentioned below.

Example 21

Preparation of Example 13 Form II

Example 13 (0.01-0.03 g) was put into a glass screw tube bottle, and acetone/heptane mixture (1:1) (about 0.02 mL) was added thereto. The screw tube bottle was capped, and the solution was heated at about 80° C. for about one hour. The screw tube bottle was decapped, and left to stand at room temperature for one day. The obtained form II of the compound of Example 13 was isolated, and the product was characterized as mentioned below.

Example 22

Preparation of Example 13 Form III

Example 13 (0.01-0.03 g) was put into a glass screw tube bottle, and ethyl acetate (about 0.02 mL) was added thereto. The screw tube bottle was capped and the suspension was shaken at about 50° C. for about 10 days. The obtained form III of the compound of Example 13 was isolated, and the product was characterized as mentioned below.

Characterization of Crystalline Form

The crystalline forms of the present invention were characterized by various analytical techniques including X-ray powder diffraction (XRPD), differential scanning calorimetry (DSC), thermogravimetric analysis (TGA), and dynamic vapor adsorption (DVS), according to the following procedures.

Example 23

X-Ray Powder Diffraction (XRPD) of the Compounds Prepared in Examples 20=22

XRPD analyses of Example 13 forms I to III were carried out according to the following measurement condition.

X-ray powder diffraction (Measurement condition A): XRPD analyses were carried out with a diffractometer (Bruker AXS D8 ADVANCE, Bruker, Billerica, Mass., America) using copper emission (Cu Kα1, λ=1.5406 Å), Kα2, λ=1.5444 Å)). The powderized sample was put on the center of the steel holder with a zero background plate and prepared for the analysis. The electric generator was operated to adjust the voltage and the amperage to 40 kV and 40 mA, respectively. The slits used herein were Soller slits 2.500 rad, scattered rays elimination 1.0°, and exhalation slit. The rotation speed of the sample was 0.25 rps. The scanning was carried out in the range of 2θ of 2-40° for 10 minutes, step size (2θ) of 0.015°. The data analysis was carried out with DIFFRAC.EVA (Bruker, Billerica, Mass., America).

X-ray powder diffraction (Measurement condition B): XRPD analyses were carried out with a diffractometer (PANanalytical XPERT-PRO, PANanalytical B.V., Almelo, Netherlands) using copper emission (Cu Kα, λ=1.5418 Å). The powderized sample was put on the center of the steel holder with a zero background plate and prepared for the analysis. The electric generator was operated to adjust the voltage and the amperage to 40 kV and 40 mA, respectively. The slits used herein were Soller slits 2.500 rad, scattered rays elimination 1.0°, and exhalation slit. The rotation speed of the sample was 0.25 rps. The scanning was carried out in the range of 2θ of 4-40° for 10 minutes, step size (2θ) of 0.015°. The data analysis was carried out with HigiScore Plus ver. 4.9 (Malvern PANanalytical B.V., Almelo, Netherlands).

The XRPD analysis of Example 13 form I was carried out according to Measurement condition A. The XRPD pattern of Example 13 form I is shown in Table 9 and FIG. 2.

TABLE 9

Example 13 form I

| Peak position (2Θ) | Relative intensity |
|---|---|
| 5.735 | 100.0% |
| 17.262 | 32.7% |
| 14.079 | 23.0% |
| 23.289 | 7.8% |
| 23.087 | 7.7% |
| 26.503 | 7.2% |
| 19.125 | 7.0% |
| 21.566 | 6.7% |
| 22.461 | 3.3% |
| 19.334 | 3.1% |
| 28.704 | 2.4% |
| 28.948 | 2.2% |
| 25.502 | 1.6% |
| 34.912 | 1.5% |
| 18.350 | 1.4% |
| 25.852 | 1.0% |
| 32.698 | 1.0% |
| 31.818 | 0.9% |
| 25.053 | 0.7% |
| 31.251 | 0.5% |
| 36.644 | 0.4% |
| 28.301 | 0.4% |
| 11.489 | 0.4% |
| 39.346 | 0.3% |
| 21.841 | 0.3% |
| 32.127 | 0.3% |
| 29.332 | 0.2% |
| 13.365 | 0.2% |
| 37.749 | 0.2% |
| 37.266 | 0.2% |
| 16.755 | 0.2% |
| 20.334 | 0.7% |

The XRPD analysis of Example 13 form II was carried out according to Measurement condition B. The XRPD pattern of Example 13 form II is shown in Table 10 and FIG. 3.

TABLE 10

Example 13 form II

| Peak position (2Θ) | Relative Intensity |
|---|---|
| 17.581 | 100.0% |
| 8.723 | 79.3% |
| 13.525 | 77.6% |
| 22.634 | 57.4% |
| 21.645 | 54.5% |
| 26.801 | 36.9% |
| 20.344 | 31.2% |
| 15.518 | 21.8% |
| 26.240 | 16.4% |
| 35.202 | 10.6% |
| 29.297 | 7.5% |

The XRPD analysis of Example 13 form III was carried out according to Measurement condition A. The XRPD pattern of Example 13 form III is shown in Table 11 and FIG. 4.

TABLE 11

Example 13 form III

| Peak position (2Θ) | Relative intensity |
|---|---|
| 11.114 | 100.0% |
| 20.264 | 82.6% |
| 13.785 | 66.1% |
| 16.975 | 41.1% |
| 21.365 | 38.6% |
| 26.254 | 37.8% |
| 27.947 | 28.2% |
| 22.366 | 26.7% |
| 24.846 | 23.8% |
| 22.062 | 21.0% |
| 18.444 | 17.0% |
| 28.534 | 11.5% |
| 13.224 | 10.9% |
| 29.309 | 8.0% |
| 38.501 | 5.0% |
| 34.566 | 4.7% |
| 14.770 | 4.3% |
| 35.679 | 3.8% |
| 31.633 | 3.8% |
| 32.683 | 3.3% |
| 20.056 | 3.2% |
| 23.292 | 3.0% |
| 31.389 | 3.0% |
| 33.727 | 2.9% |
| 30.116 | 2.8% |
| 18.328 | 2.3% |
| 23.626 | 2.0% |
| 29.826 | 1.8% |
| 34.387 | 1.5% |
| 37.571 | 1.4% |
| 32.999 | 1.4% |
| 15.651 | 1.0% |
| 27.542 | 0.9% |
| 16.712 | 0.8% |
| 28.785 | 0.7% |
| 23.759 | 0.7% |
| 36.171 | 0.3% |
| 10.006 | 0.3% |
| 36.988 | 0.3% |
| 35.293 | 0.2% |

Example 24

Differential Scanning Calorimetry (DSC) of the Compounds Prepared in Examples 20-22

The differential scanning calorimetry of Example 13 forms I to III was carried out according to the following procedure.

Differential scanning calorimetry: the thermal characteristic was evaluated with a differential scanning calorimetry (DSC) instrument (DSCQ1000, TA Instruments, New Castle, Del., USA). For each trial, about 1-10 mg of the solid sample was put in a standard aluminium pot aerated with a pinhole, and heated at a rate of 5-10° C./min under a nitrogen purge of 50 mL/min. The data analysis was carried out with Universal Analysis 2000 Version 4.1D (TA Instruments, New Castle, Del., USA).

The DSC of Example 13 form I is shown in FIG. 5. Form I has a melting point of higher than 100° C., and the crystalline stability thereof is high.

The DSC of Example 13 form II is shown in FIG. 6. Form II has a melting point of higher than 100° C., and the crystalline stability thereof is high.

The DSC of Example 13 form III is shown in FIG. 7. Form III has a melting point of higher than 100° C., and the crystalline stability thereof is high.

Example 25

Thermogravimetric Analysis (TGA) of the Compounds Prepared in Examples 20-22

The thermogravimetric analysis of Example 13 forms I to III was carried out according to the following procedure. Thermogravimetric analysis: the thermogravimetric analysis (TGA) was carried out with a TGA instrument (TGA Q500, TA Instruments, New Castle, Del., USA). For each trial, about 1-10 mg of the solid sample was put in an open aluminium pot, and heated at a rate of 5-10° C./min under a nitrogen purge of 60 mL/min. The data analysis was carried out with Universal Analysis 2000 Version 4.1D (TA Instruments, New Castle, Del., USA).

The TGA of Example 13 form I is shown in FIG. 8. There was no weight reduction in form I until its melting temperature, thus form I is suitable for drug formulation.

The TGA of Example 13 form II is shown in FIG. 9. There was no weight reduction in form II until its melting temperature, thus form II is suitable for drug formulation.

The TGA of Example 13 form III is shown in FIG. 10. There was no weight reduction in form III until its melting temperature, thus form III is suitable for drug formulation.

Example 26

Dynamic Vapor Adsorption (DVS) of the Compounds Prepared in Examples 20-22

The dynamic vapor adsorption measurement of Example 13 forms I to III was carried out according to the following procedure.

Dynamic vapor adsorption: the hygroscopicity was evaluated with a dynamic vapor adsorption (DVS) instrument (IGAsorp, Hiden Isochema, Warrington, England) at room temperature. The water adsorption/desorption was studied as a function of relative humidity (RH) in the range of 0-90% at 25° C. The relative humidity in the chamber was made to increase by 10% RH, and the humidity was retained until the humidity state of the atmosphere and the weight variation of solid achieved equilibrium. The equilibration test was continued until the test was passed or failed 5 or 10 hours later. At this time point, RH increased by 10%, and the absorption process was repeated until the RH achieved to 90% RH and the humidity state achieved equilibrium. During the test, the moisture sorption was being monitored. For the desorption, the relative humidity was decreased in a similar manner to measure a perfect adsorption/desorption cycle. The cycle was repeated as appropriate. All the experiments were operated in dm/dt mode (weight variation over time) to determine each equilibrating endpoint. About 5-10 mg of the solid was used. The date analyses were carried out with Hisorp v4.02 (Hiden Isochema, Warrington, England).

The DVS of Example 13 form I is shown in FIG. 11. The weight variation of form I in 0-90% RH was within 1%, and thus form I is suitable for drug formulation.

The DVS of Example 13 form II is shown in FIG. 12. The weight variation of form II in 0-90% RH was within 1%, and thus form II is suitable for drug formulation.

The DVS of Example 13 form III is shown in FIG. 13. The weight variation of form III in 0-90% RH was within 1%, and thus form III is suitable for drug formulation.

Example 27: Preparation of Example 13 Form III (Alternative Process)

Each of Example 13 form I, form II, and form III (0.08-0.12 g) was added to different glass screw tube bottles. Ethanol, 2-propanol, chloroform, acetonitrile, tetrahydrofuran, ethyl acetate, acetone, and tetrahydrofuran/heptane mixture (1:1) (about 0.02 mL) were added to each screw tube bottle, and each screw tube bottle was capped. The suspension in each screw tube bottle was shaken at 45-55° C. for about 9-11 days. Then, the compound of Example 13 form III was isolated in all the glass screw tube bottles.

The results of pharmacological experiments with some typical compounds of the present invention are shown below and the pharmacological activities of the present compounds are also explained below, but the scope of the present invention should not be limited thereto.

Test 1. T-Type Calcium Channel Inhibitory Activity

The inhibitory activity of the present compounds for T-type calcium channel was measured by whole-cell patch-clamp method with HEK293 cell (vendor of HEK 293 cell: ATCC, Manassas, Va., USA, builder of expressing cell: ChanTest Corporation., Cleveland, Ohio, USA), in which human Cav3.1, human Cav3.2, or human Cav3.3 is expressed. The culture medium used for HEK293 cell was prepared by adding fetal bovine serum (10%), sodium penicillin G (100 U/mL), streptomycin sulfate (100 μg/mL), and G418 (500 μg/mL) to a mixture medium of Dulbecco's modified Eagle's medium/Ham's F-12 medium. The whole-cell current was evaluated with IonWorks Barracuda system and Population Patch Clamp (both are provided by Molecular Device Corporation, Union City, Calif., USA). The extracellular recording solution used during the recording was Hanks' balanced salt solution. The internal recording solution used herein was 50 mmol/L CsCl, 90 mmol/L CsF, 5 mmol/L $MgCl_2$, 1 mmol/L glycol ether diamine tetraacetic acid (EGTA), and 10 mmol/L 4-(2-hydroxyethyl)piperazine-1-ethanesulfonic acid (HEPES (pH 7.2). The holding voltage was held at −90 mV, then changed to −65 mV. 60 seconds later, −20 mV pulse was added thereto for 200 millisecond to activate the channel on plasma membrane and generate calcium current. The calcium current was recorded with an amplifier of IonWorks Barracuda system, and analyzed with a program of the system (Version 2.0.2). The record of the calcium current was obtained twice, before and after the addition of the compound. In the measurement after adding the compound, the cells were exposed to the recording solution containing the compound for more than 5 minutes and then the current was measured. In the analyses, the ratio of current readout after the compound addition per current readout before the compound addition was calculated, the calculated value was subtracted from one, and the obtained value was converted to percentage. In addition, the percentage calculated from the positive control compound and the percentage calculated from the solvent treatment were assumed to be 100% and 0% inhibitions, respectively. The value obtained from each compound was canonicalized based on the two ends of values to obtain each inhibitory rate. The positive control compound used herein was TTA-A2 which is known as T-type calcium channel inhibitor. $IC_{50}$ value was calculated with Hill equation.

Each inhibitory rate (%) against T-type calcium channel at the evaluation concentration of the present compound (600 μmol/L) is shown in Table 12, in which the parenthesized values are $IC_{50}$ values (μmol/L)) calculated from the dose-reactive test.

TABLE 12

| Example | Cav3.1% | C3.2% | Cav3.3% |
| --- | --- | --- | --- |
| 1 | 46.0 (449) | 33.0 (848) | 30.7 (922) |
| 2 | 72.7 | 64.0 | 70.0 |
| 3 | 69.9 (325) | 64.0 (362) | 61.0 (440) |
| 5 | 64.5 | 54.0 | 55.6 |

TABLE 12-continued

| Example | Cav3.1% | C3.2% | Cav3.3% |
|---|---|---|---|
| 6 | 80.4 | 67.4 | 72.9 |
| 8 | 83.1 (216) | 70.3 (318) | 73.0 (321) |
| 9 | 96.5 | 96.9 | 94.3 |
| 10 | 68.5 | 57.7 | 69.7 |
| 11 | 56.0 | 50.8 | 54.3 |
| 12 | 95.0 | 91.5 | 93.0 |
| 13 | 50.9 (465) | 42.6 (713) | 39.9 (746) |
| 14 | 49.6 (549) | 33.8 (839) | 31.8 (888) |

Test 2. Potentiating Effect of Levodopa-Induced Hyperactivity in Reserpine-Induced Parkinson's Disease Model Mouse Dopamine-depleted mice due to reserpine treatment are model mice of akinesia symptoms in Parkinson's disease, said symptoms are relieved with levodopa (L-DOPA). The effect of the present compounds for potentiating the levodopa's effect was tested.

Figure 14:
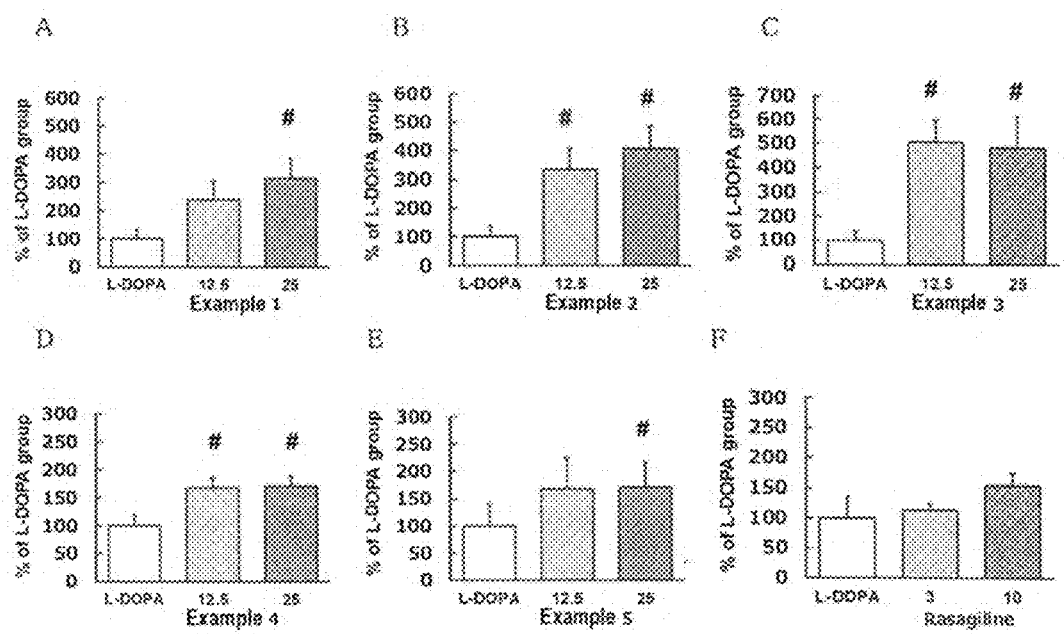
FIG. 14 shows the results of Test 2 about Examples 1-5, which show the potentiating effect to levodopa-induced hyperactivity in reserpine-induced Parkinson's disease model mouse. The white columns indicate the total movement in the levodopa single administration group as 100%, and the colored columns indicate the total movements in the combination administration groups of levodopa and each dose (mg/kg) of Example/rasagiline, which are each ratio (%) per the total movement in the levodopa single administration group.

In the present test, male Crl: CD1 (ICR) mice (CHARLES RIVER LABORATORIES JAPAN, INC.) were used. 20-24 hours before starting the movement measurement, reserpine (3 mg/kg) was intraperitoneally administered to the mouse. One hour before starting the movement measurement, the present compound (12-.5 mg/kg or 25 mg/kg of. Examples 1, 2, 3, 4, and 5) was orally administered to the mouse. Shortly before starting the movement measurement, levodopa (200 mg/kg) with benserazide whose amount was ¼ of levodopa in free form was intraperitoneally administered to the mouse. The movement measurement was carried out for 90 minutes, and each total movement was compared. The results are shown in FIG. 14. The compounds of Examples 1, 2, 3, 4, and 5 exhibited significantly-potentiating effect of levodopa-induced hyperactivity in akinesia mice. On the other hand, rasagiline (3 mg/kg or 10 mg/kg) which is a MAOB inhibitor used as a drug for treating Parkinson's disease in clinical practice also exhibited a tendency to increase the movement, but the increase had no statistically-significant difference.

The result suggests that the present compound can potentiate the effect of levodopa used in the treatment of Parkinson's disease. Similarly in humans, the present compound is expected to potentiate the effect of levodopa used in the treatment of Parkinson's disease according to the conventional known protocol.

In FIG. 14, (A) N=7 or 8, (B) N=8, (C) N=7, (D) N=13 or 14, (E) N=6, 7, or 8, (F) N=7 or 8. And, # means p<0.05 in statistical comparison with L-DOPA single administration group (Dunnett's test).

Test 3. Effect for Extending Duration of Levodopa-Induced Rotational Behavior in Unilateral Lesion Model of Nigrostriatal Dopamine Neuron Induced with 6-hydroxydopamine (6-OHDA)

6-OHDA is a neurotoxin specifically-lesioning dopamine neuron. A model whose dopamine neuron projecting from unilateral substantia nigra to striatum is lesioned by injecting 6-OHDA in unilateral medial forebrain bundle (MFB) is known to exhibit rotational behavior by administering a drug for treating Parkinson's disease which can activate the intracerebral dopamine neuron system such as levodopa and dopamine receptor agonist. The rotational behavior can be used as an indicator for evaluating the utility of a drug for treating Parkinson's disease. The elongation of the rotational behavior duration with levodopa can bring in the elongation of the ON time in Parkinson's disease. In order to evaluate the effect of the present compounds for elongating the ON time, the elongation of the levodopa-induced rotational behavior duration was evaluated with the present model.

In the present test, male Slc: Wistar rats (Japan SLC, Inc.) were used. 30 minutes before the anesthesia treatment in the lesion operation, desipramine (25 mg/kg) was intraperitoneally administered to the rat. Under anesthesia, the rat was fixed on a device for fixing a brain. 9 μg/4 μL of 6-OHDA (containing 0.02% ascorbic acid) was administered over 4 minutes to the medial forebrain bundle of the rat (AP: −4.4 mm, ML: 1.5 mm, DV: 7.8 mm from bregma as origination). Two weeks after the operation, apomorphine hydrochloride (0.5 mg/kg) was subcutaneously administered to the rat, and the rotational behavior was observed. Rats which rotated 7 times or more per minute were used as model animals herein.

To these rats, the present compound (Examples 1, 2, 3, 5, 8, 13, and 14, 10 mg/kg or 30 mg/kg for each compound) was orally administered 60 minutes before the observation of the rotational behavior. Levodopa methyl ester hydrochloride (5 mg/kg in terms of levodopa free form) was intraperitoneally administered to the rat 20 minutes before the observation of the rotational behavior, wherein said levodopa contained ¼ (w/w) benserazide per levodopa in terms of free form. The rotational behavior was observed for 120 minutes, and each rotational frequency between 100 minutes and 120 minutes from the beginning of the observation was aggregated as the rotational number in the late phase.

Figure 15:
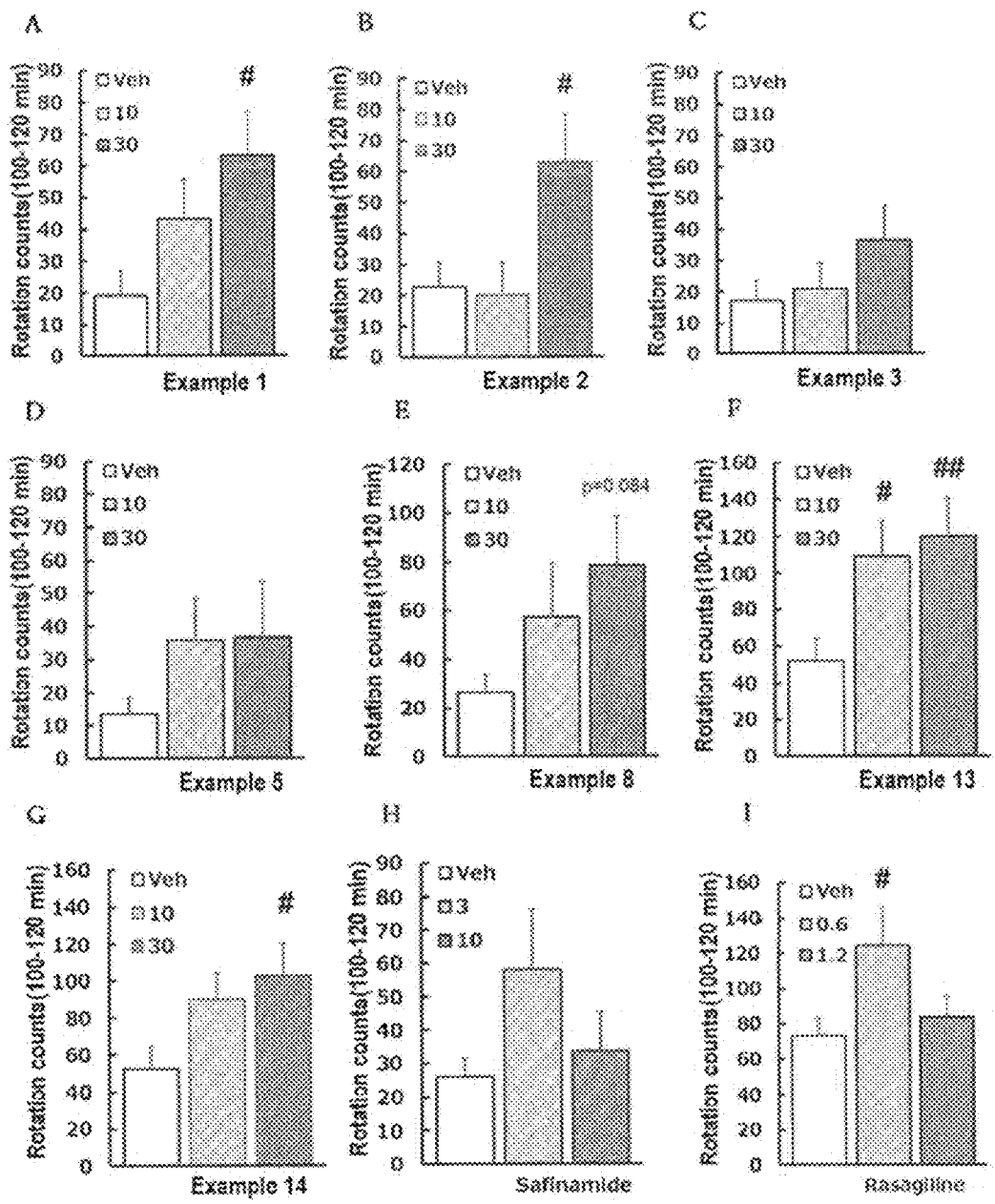
FIG. 15 shows the results of Test 3 about Examples 1, 2, 3, 5, 8, 13, and 14, which show the effect for extending duration of levodopa-induced rotational behavior in unilateral lesion model of nigrostriatal dopamine neuron induced with 6-hydroxydopamine (6-OHDA). The axis of ordinate denotes the number of rotations in the late phase (between 100 minutes and 120 minutes from the beginning of the observation of the rotational behavior). The white columns (Veh) indicate the results of the levodopa single administration group, and the colored columns indicate the results of the combination administration groups of levodopa and each Example, safinamide, or rasagiline, with the indication of its dose (mg/kg).

The result is shown in FIG. 15, which showed that the compounds of Examples 1, 2, 13, and 14 and rasagiline (0.6 mg/kg) that is an MAOB inhibitor significantly increased the rotational number in the late phase. And, the compounds of Examples 3, 5, and 8 and safinamide that is an MAOB inhibitor did not show statistically-significant increase, but showed a tendency to increase the rotational number in the late phase.

The result shows that the present compound can sustain the effect of levodopa used in the treatment of Parkinson's disease. Similarly in humans, the present compound is expected to elongate the ON time of levodopa in the treatment of Parkinson's disease according to the conventional known protocol.

In FIG. 15, (A) N=12, (B) N=10, 11, or 12, (C) N=9 or 11, (D) N=7 or 12, (E) N=10 or 11, (F) N=12 or 16, (G) N=12 or 16, (H) N=10, 11, or 12, (I) N=10 or 11. And, # and ## mean p<0.05 and p<0.01 in statistical comparison with L-DOPA single administration group (Dunnett's test), respectively.

Test 4. Anti-Tremor Effect in Tacrine-Induced Parkinson's Disease Tremor Model

One of the causes of tremor in Parkinson's disease is thought to be a decrease of intracerebral dopamine content, said decrease can hyper-activate the cholinergic nervous system in a counteractive manner to cause the symptom. In the present model, an acetylcholinesterase inhibitor activates the cholinergic nervous system, which breaks down the balance between intracerebral dopamine and acetylcholine to initiate a tremor symptom. Thus, the model is well known as a drug-induced model suffering from tremor in Parkinson's disease. With the present model, the effect of the present compound for inhibiting the tremor in Parkinson's disease was evaluated.

Figure 16:
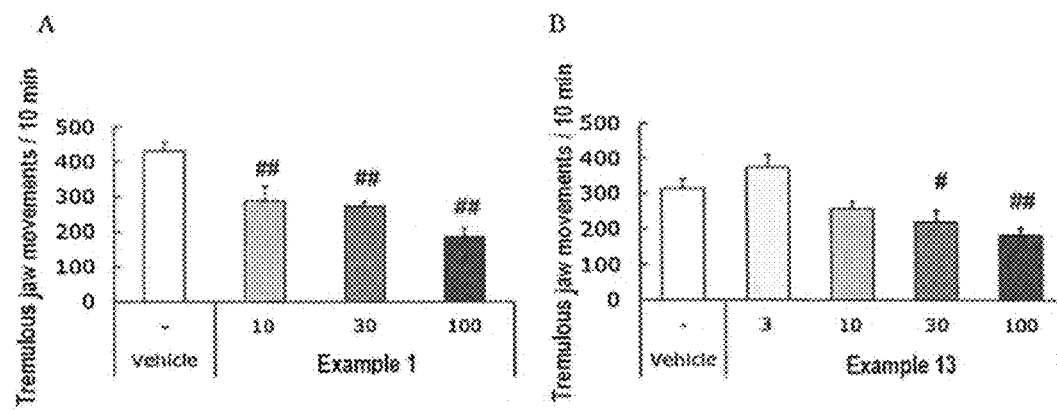
FIG. 16 shows the results of Test 4 about Examples 1 and 13, which shows the anti-tremor effect in tacrine-induced Parkinson's tremor model. The axis of ordinate denotes the number of tremulous jaw movements in 10 minutes, wherein the counting started 10 minutes after the administration of tacrine. The white columns (Vehicle) indicate the results of the tacrine single administration group, and the colored columns indicate the results of the combination administration groups of tacrine and each Example, with the indication of its dose (mg/kg).

In the present test, male Slc: SD rats (Japan SLC, Inc.) were used. The present compound (Example 1 (10 mg/kg, 30 mg/kg, or 100 mg/kg), Example 13 (3 mg/kg, 10 mg/kg, 30 mg/kg, or 100 mg/kg)) was orally administered to the rat. One hour later, tacrine (2.5 mg/kg) was intraperitoneally administered to the rat. Ten minutes after the administration of tacrine, the number of tremulous jaw movements was counted for 10 minutes. The result is shown in FIG. 16. The compounds of Examples 1 and 13 significantly decreased the number of tremulous jaw movements per unit time.

The result suggests that the oral administration of the present compound can suppress a tremor symptom in Parkinson's disease. Similarly in humans, the present compound is expected to be effective in the treatment of Parkinson's disease tremor according to the conventional known protocol.

In FIG. 16, (A) N=9 or 10, (B) N=10 or 12. And, # and ## mean $p<0.05$ and $p<0.01$ in statistical comparison with tacrine single administration group (Dunnett's test), respectively.

Test 5. Effect for Inhibiting Levodopa-Induced Dyskinesia

A unilateral lesion model of nigrostriatal dopamine neuron induced with 6-hydroxydopamine (6-OHDA) is broadly used for evaluating the drug efficacy for treating Parkinson's disease, as mentioned in Test 2. In addition, it is known that dyskinesia is developed when the present model receives repetitive administration of levodopa, which is similar to the phenomenon that patients of Parkinson's disease who have received long-term administration of levodopa develop dyskinesia. With the present model, the effect of the present compound on the dyskinesia induced by repetitive administration of levodopa was evaluated.

As shown in Test 2, a unilateral lesion model of nigrostriatal dopamine neuron was prepared. One day before starting the repetitive administration of levodopa, levodopa methyl ester hydrochloride (5.86 mg/kg) containing benserazide hydrochloride (22.8 mg/kg) (whose ratio was 4:1 in terms of free form) was intraperitoneally administered to the model, and the rotational behavior of the model was observed from 20 minutes to 140 minutes after the administration. The models were classified considering three factors of the total rotation number (20-140 minutes after the administration), the later term of the rotation (120-140 minutes after the administration), and the rotational duration, so that the dispersion of each group could be equal.

Two days after the classification, the repetitive administration of levodopa methyl ester hydrochloride (6 mg/kg) and benserazide hydrochloride (12 mg/kg) once a day for two weeks was started. Example 1 (30 mg/kg or 100 mg/kg), Example 13 (30 mg/kg or 100 mg/kg), and a MAOB inhibitor, rasagiline (0.2 mg/kg or 0.6 mg/kg) were administered every day one hour before the administration of levodopa.

The evaluation of dyskinesia was done after one week and two weeks of the repetitive administration. After the administration of L-DOPA, each rat was put into a transparent cylindrical cage for measuring dyskinesia. 20 minutes later, the behavior was repeatedly observed for one minute every 20 minutes, and the dyskinetic symptom was scored. The scoring was carried out based on Abnormal Involuntary Movement Scales (AIMS; Neurobiology of Disease 10, 165-186 (2002)) for rats: (evaluation content: [rotational behavior] circling movements toward contralateral side to the lesion, [movement of upper limb] involuntary bending and stretching, paw opening and closing, wrist twisting up-and-down, chorea-like trembling, dystonia-like rigidity, [body axis] twisting movements of the upper part of the body and the neck towards the side contralateral to the lesion, getting off balance and falling down, maintaining dystonic posturing, [orolingual] involuntary abnormal movement of jaw and frontward tongue protrusion, [scoring] 0: absent, 1: present during less than 30 seconds, 2: present during 30 seconds or more, 3: continuous (which can be stopped by a stimulation such as sound), 4: continuous (which cannot be stopped by a stimulation such as sound)). The observation was done for 180 minutes after the administration of levodopa.

Figure 17:
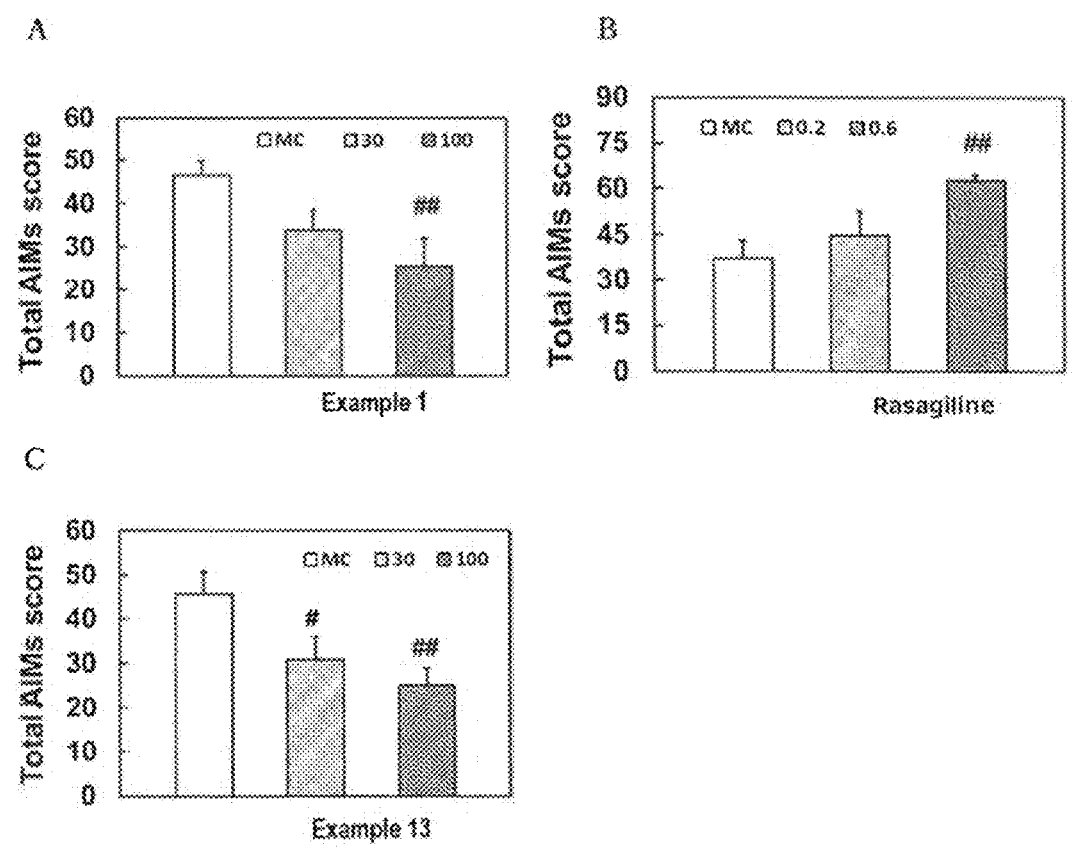
FIG. 17 shows the results of Test 5 about Examples 1 and 13, which shows the effect for inhibiting levodopa-induced dyskinesia. The axis of ordinate denotes the total score of dyskinesia-like symptom, which was scored every 20 minutes from 20 minutes to 180 minutes after the levodopa administration. The white columns (MC) indicate the results of the levodopa-vehicle repetitive administration group, and the colored columns indicate the results of the combination administration groups of levodopa and each Example or rasagiline, with the indication of its dose (mg/kg).

The result is shown in FIG. 17. In the repetitive administration group of Examples 1 and 13, the onset of dyskinesia induced by repetitive administration of levodopa was inhibited, and the effect exhibited a statistically significant difference compared with vehicle-repetitive administration group. On the other hand, in the repetitive administration group of rasagiline which is an MAOB inhibitor, the dyskinesia induced by repetitive administration of levodopa significantly got worse. The result suggests that the repetitive administration of the present compound can inhibit the onset of levodopa-induced dyskinesia in Parkinson's disease. Similarly in humans, the present compound is expected to be effective for inhibiting the onset of drug-induced dyskinesia caused by the long-term administration of levodopa according to the conventional known protocol.

In FIG. 17, (A) N=10, (B) N=10 or 11, (C) N=10. And, ## means $p<0.01$ in statistical comparison with L-DOPA and vehicle repetitive administration group (Dunnett's test).

Test 6. Activity for Inhibiting Monoamine Oxidase B (MAOB)

MAOB is an enzyme involved in oxidative de-amino acid reaction of an endogenous monoamine neurotransmitter such as dopamine. MAOB inhibitor can increase the intracerebral dopamine concentration by inhibiting the decomposition of dopamine to improve parkinsonism, but excess increase of the dopamine concentration may cause side effects such as dyskinesia. The effect of the present compounds for inhibiting MAOB in rat striatum and simian striatum was tested.

Mitochondria•synaptosome fraction containing MAOB was prepared according to the following procedure. To striata of male Slc: Wistar rat (Japan SLC, Inc.) or male cynomolgus monkey (HAMRI CO., LTD.) was added 0.32 mol/L aqueous sucrose by 10 mL per 1 gram as wet weight of the tissue, and the mixture was homogenized. The homogenate was centrifuged at 4° C. at 1,000 g for 10 minutes, and the obtained supernatant was centrifuged again at 4° C. at 17,200 g for 20 minutes. To the obtained precipitate was added a prepared buffer solution (10 mmol/L Tris-HCl buffer solution (pH 7.4), 0.25 mol/L aqueous sucrose, 0.5 mmol/L EDTA-2K) by 10 mL per 1 gram as wet weight of the original tissue, and the mixture was centrifuged again at 4° C. at 17,200 g for 20 minutes. To the obtained precipitate was added the prepared buffer solution by 40 mL per 1 gram as wet weight of the original tissue. The mixture was suspended to be used as an enzyme homogenate solution.

As a substance to be degraded by MAOB, $^{14}$C-labeled β-phenylethylamine ([$^{14}$C] β-PEA) was used. [$^{14}$C] β-PEA and the present compound solution diluted to each concentration were incubated with the enzyme homogenate solution at 37° C. for a given period, and then the reaction was stopped by adding 3 mol/L cold HCl thereto. The reaction product was extracted with a mixture of water-saturated toluene and ethyl acetate (1:1). The supernatant organic layer was separated, a liquid scintillation cocktail (ACSII, GE Healthcare) was added to the separated organic layer, and the radioactivity was measured with a liquid scintillation counter (TRI-CARB 3100TR, Packard). The $IC_{50}$ value of each compound was determined based on two parameter logistic model with the inhibitory data of each concentration, said data were obtained from plural trials. As an experimental positive control compound in the present test, safinamide which is a selective MAOB inhibitor was used.

The result is shown in Table 13, wherein safinamide exhibited a strong MAOB inhibitory action, but each compound of the present invention all exhibited extremely weak MAOB inhibitory action. Considering the present result and the results of Tests 1 and 2 on the whole, it is suggested that the compound of the present invention is an agent for potentiating the effect of levodopa without inhibiting MAOB.

TABLE 13

| Example | Rat striatum MAOB $IC_{50}$ (μmol/L) |
|---|---|
| 1 | 349 |
| 2 | >600 |
| 3 | 101 |
| 4 | 389 |
| 5 | >600 |
| 6 | >600 |
| 7 | >600 |
| 8 | >600 |
| 10 | >600 |
| 11 | >600 |
| 12 | 150 |
| 13 | >600 |
| 14 | >600 |
| safinamide (positive control) | 0.193 |

Test 7. Anti-Tremor Effect in Harmaline-Induced Essential Tremor Model

As an animal model of essential tremor, an animal administrated with harmaline is broadly used in its evaluation test. Harmaline can excessively activate the inferior olivary nucleus in medulla oblongata to cause abnormal network activity of cerebellum-thalamus-cortex that is involved in motor control, which can induce action tremor that is a pathognomonic symptom of essential tremor. The effect of the present compounds for harmaline-acute-administration-induced tremor was studied.

To male Crl: CD1 mice (6-7 weeks old) (CHARLES RIVER LABORATORIES JAPAN, INC.), harmaline (30 mg/kg) was intraperitoneally administered to induce tremor. The present compound (Example 1 (25 mg/kg or 50 mg/kg), Example 13 (25 mg/kg or 50 mg/kg), or Example 14 (3.125 mg/kg, 6.25 mg/kg, 12.5 mg/kg, or 25 mg/kg)) was orally administered to the mouse one hour before the administration of harmaline. And, saline or β-propranolol (10 mg/kg) which is a positive control compound was intraperitoneally administered to the mouse 20 minutes before the administration of harmaline. 35 minutes before the administration of harmaline, the mouse was put into a measurement cage (an acrylic cylinder set in a horizontal direction, φ 65 mm, length 145 mm), one cage to one mouse, said measurement cage was in a soundproof box of a startle response instrument (O'hara & Co., Ltd., Tokyo). The trembling that the mouse gave were recorded over time as tremor data. The animal was put into cage, and the data were recorded for 20 minutes just before (PRE) and just after (POST) the administration of harmaline. The time-series signal data were analyzed about frequency with an analysis software, Vital-Tracer and BIMUTAS II-A (both, Kissei Comtech Co., Ltd., Matsumoto-shi). At 12-15 Hz or 12-18 Hz as a frequency which increases with tremor, the spectrum amounts were extracted, and the tremor intensity T of each subject was calculated according to the following formula.

$$T = POST/PRE$$

Figure 18:
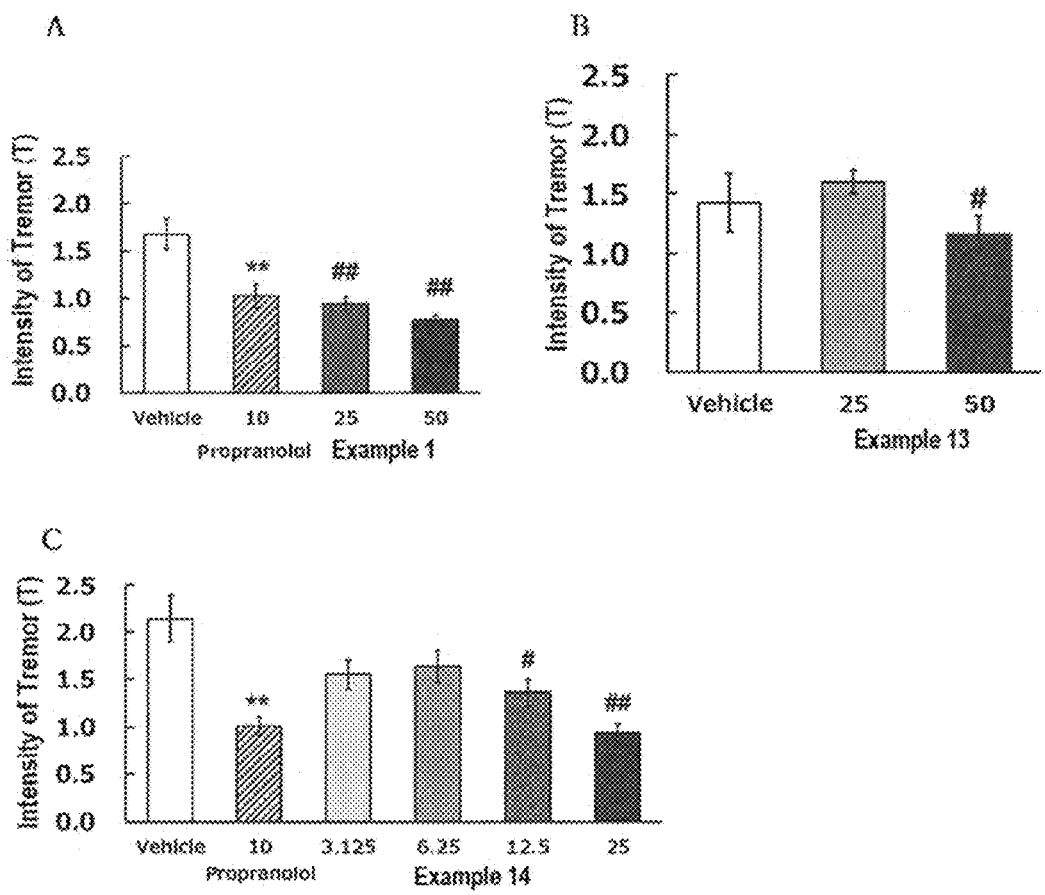
FIG. 18 shows the results of Test 7 about Examples 1, 13, and 14, which shows the anti-tremor effect in harmaline-induced essential tremor model. The axis of ordinate denotes the intensity of harmaline-induced tremor. The white columns (Vehicle) indicate the results of the harmaline single administration group, the shaded columns (Propranolol) indicate the combination administration groups of harmaline and β-propranolol (10 mg/kg), and the colored columns indicate the combination administration groups of harmaline and each Example, with the indication of its dose (mg/kg).

The result is shown in FIG. 18. Examples 1, 13, and 14 inhibited harmaline-induced tremor. β-Propranolol which has been clinically used as an agent for treating essential tremor also significantly inhibited harmaline-induced tremor. These results suggest that the present compound is effective for essential tremor. Similarly in humans, the present compound is expected to be effective in the treatment of essential tremor according to the conventional known protocol.

In FIG. 18, (A) N=11 or 12, (B) N=16, (C) N=7, 13, or 14. And, ** means p<0.01 in statistical comparison with harmaline single administration group (Welch's t-test). # and ## mean p<0.05 and p<0.01 in statistical comparison with harmaline single administration group (Dunnett's test), respectively.

Test 8. Anti-Allodynia Effect in Chemotherapy-Induced Peripheral Neuropathy Model As one of chemotherapy-induced peripheral neuropathy, sensory disturbance due to neuropathy caused by a platinating agent that is an anticancer agent such as cisplatin and oxaliplatin is known, and the symptom is difficult to be recovered even after the medication is discontinued. The therapeutic effect for sensory disturbance caused by repetitive administration of oxaliplatin was studied in the present test.

To male Crl: CD (SD) rats (7 weeks old) (CHARLES RIVER LABORATORIES JAPAN, INC.), oxaliplatin (5 mg/kg) was intraperitoneally administered for the two consecutive days in a week, totally 6 times, to prepare chemotherapy-induced peripheral neuropathy models. The compound of Example 13 (100 mg/kg) was repeatedly orally administered once a day, totally 17 times. On the day of oxaliplatin-administration, the compound of Example 13 was administered one hour before the administration of oxaliplatin. A positive control substance, duloxetine (30 mg/kg), was orally administered one hour before the acetone test. The acetone test was done on the 18th day from the initial day of oxaliplatin treatment. In the acetone test, 0.1 mL of acetone was sprayed to the foot sole of the rat hind paw, and the reaction was evaluated according a scoring (Cold Score). When there was no reaction for 20 seconds after spraying acetone, Score 0 was recorded and the observation was stopped. When there was any reaction for the 20 seconds, the observation was continued until 40 seconds after spraying, and the score was recorded according to the evaluation scale. The acetone spray was done twice each for right and left hind paws, and the total score was calculated.

The evaluation scale is defined as follows.

Score 0: no reaction, Score 1: showing an action such as stamping and flicking (in a moment or once), Score 2: showing an action such as stamping and flicking (continually or plural times), Score 3: showing an escape behavior accompanied with an action such as licking and biting.

Figure 19:
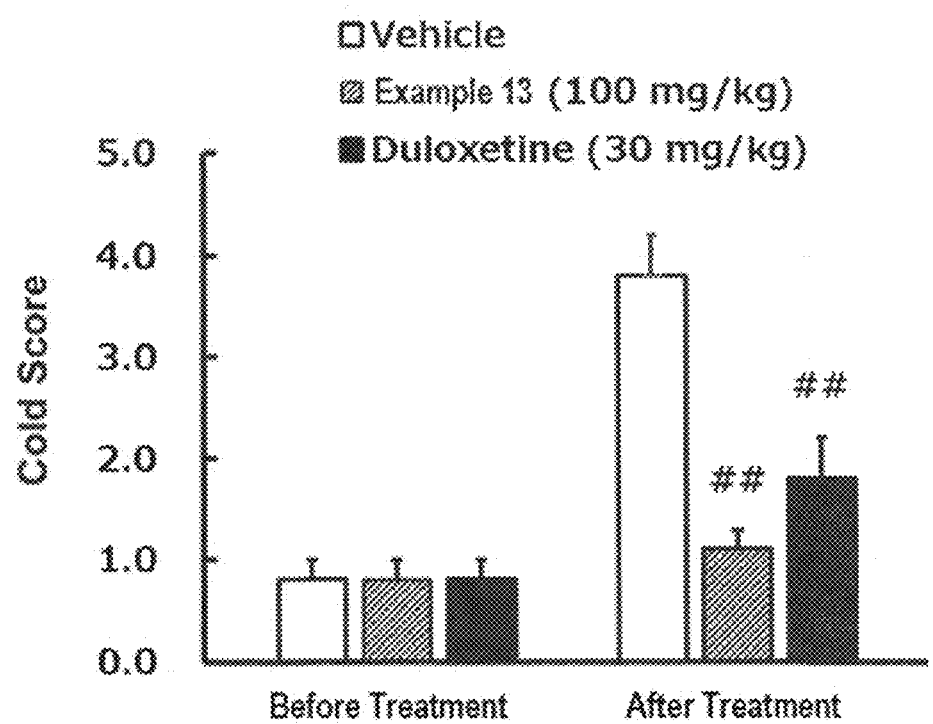
FIG. 19 shows the results of Test 8 about Example 13, which shows anti-cold allodynia effect in chemotherapy-induced peripheral neuropathy model. The axis of ordinate denotes the total score in the acetone test. The white columns indicate the results of the oxaliplatin+vehicle repetitive administration group before and after the treatment of oxaliplatin repetitive administration, and the colored columns indicate the results of the repetitive administration group of oxaliplatin+the Example compound or duloxetine.

The result is shown in FIG. 19. The result on the repeated oral administration group of Example 13 showed a significantly lower Cold Score, compared with that of the vehicle repetitive group. And, the duloxetine single administration group also showed a significantly lower Cold Score, which is used for clinically treating allodynia caused by chemotherapy-induced peripheral neuropathy. These results show that the compound of Example 13 is effective for chemotherapy-induced peripheral neuropathy (cold allodynia). Similarly in humans, the present compound is expected to be effective in the treatment of chemotherapy-induced peripheral neuropathy according to the conventional known protocol.

In FIG. 19, N=12. And, ## means p<0.01 in statistical comparison with oxaliplatin+vehicle repetitive administration group (Wilcoxon test).

Test 9. Activity for Inhibiting Carbonic Anhydrase (CA)

CA is a zinc metalloenzyme family which catalyzes reversible hydration between carbon dioxide, and bicarbonate and proton. It is known that many of compounds having a sulfonamide structure such as acetazolamide and topiramate have an activity for inhibiting CA, and CA inhibitors inhibit CA in renal tubule to cause hypercalciuria and urine pH elevation, which may cause severe side effects such as urolithiasis (Non-patent Literature 5). The present compound also has a sulfonamide structure, and the activity for inhibiting CA was evaluated in the following procedure. In the test, CA-II was used as CA, which is known as highly active CA isozyme that can bring in systemic expression, but can be strongly inhibited with acetazolamide.

As a substance for decomposition by CA-II, 4-nitrophenyl acetate was used herein. 4-Nitrophenyl acetate is dehydrated with CA-II to produce 4-nitrophenol. A commercially available human CA-II (recombinant protein, 2184-CA, R&D Systems, Inc. USA) was diluted with a prepared buffer solution (12.5 mmol/L Tris, 75 mmol/L NaCl, pH 7.5) to adjust the final concentration to 2 μg/mL. To the diluted solution were added 4-nitrophenylacetic acid (final concentration: 5 mmol/L) and the present compound of each concentration, and the mixture was incubated at 37° C. under shading for 30 minutes. A buffer solution (12.5 mmol/L Tris, pH 8.0) was added to the mixture to stop the reaction, and the amount of 4-nitrophenol which is a reaction product was measured by absorptiometry (410 nm). The $IC_{50}$ of the compound was obtained through the two-parameter logistic model with the inhibitory rate data in each concentration which was obtained from plural trials. As experimental positive control compounds, topiramate and acetazolamide which are CA inhibitors were used.

The result is shown in Table 14. Topiramate and acetazolamide both exhibited strong activity for inhibiting CA-II. On the other hand, it has been found that all the present compounds except for Examples 3, 4, and 8 exhibit weak activity for inhibiting CA-II. The result suggests that the present compounds have low risk of urolithiasis in humans.

TABLE 14

| Example | human CA-II $IC_{50}$ (μmol/L) |
| --- | --- |
| 1 | 26.5 |
| 2 | 79.2 |
| 3 | 0.084 |
| 4 | 0.023 |
| 5 | 5.2 |
| 6 | 45.7 |
| 7 | 32.9 |
| 8 | 2.2 |
| 13 | 18.2 |
| 14 | 3.5 |
| topiramate (positive control) | 0.17 |
| acetazolamide (positive control) | 0.014 |

Test 10. Anti-Tremor Effect in Unilateral Lesion Model of Nigrostriatal Dopamine Neuron Induced with 6-hydroxydopamine (6-OHDA)

A unilateral lesion model of nigrostriatal dopamine neuron induced with 6-OHDA is broadly used for evaluating the drug efficacy for treating Parkinson's disease, as shown in Test 3. In addition, the present model is known to present with jaw tremor which corresponds to the tremor frequency in a patient of Parkinson's disease, thus which is also expected to be a tremor model in Parkinson's disease. With the present model, the effect of the present compound for inhibiting the tremor in Parkinson's disease was evaluated.

Figure 20:
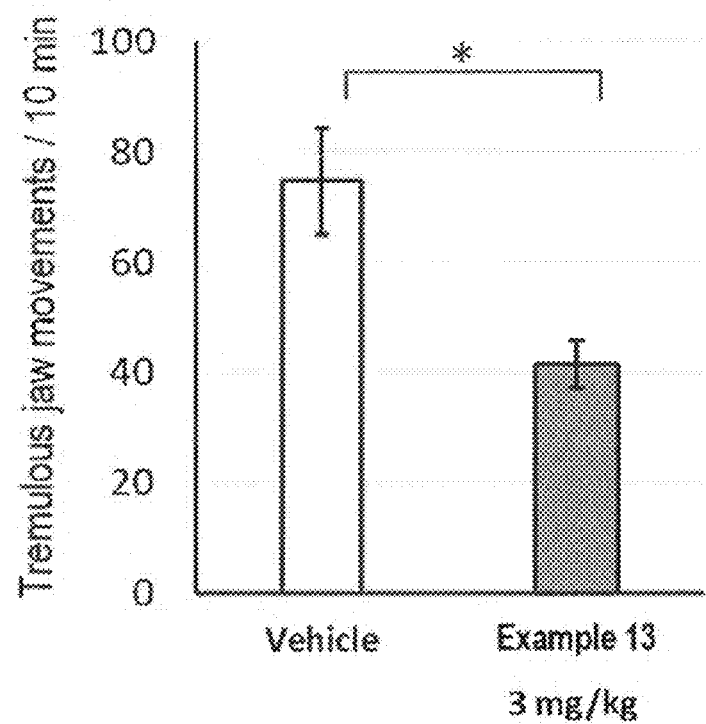
FIG. 20 shows the results of Test 10 about Example 13, which shows the anti-tremor effect in unilateral lesion model of nigrostriatal dopamine neuron induced with 6-OHDA. The axis of ordinate denotes the number of tremulous jaw movements which was counted for 10 minutes. The white column (Vehicle) indicates the result of the vehicle administration group, and the colored column indicates the result of the Example administration group, with the indication of its dose (mg/kg).

According to the procedure described in Test 3, a unilateral lesion model of nigrostriatal dopamine neuron was prepared. The compound of Example 13 (3 mg/kg) was orally administered to the model rat. One hour later, the number of tremulous jaw movements was counted for 10 minutes. The result is shown in FIG. 20. The compound of Example 13 significantly decreased the number of tremulous jaw movements per unit time.

The result suggests that the oral administration of the present compound can suppress a tremor symptom in Parkinson's disease. Similarly in humans, the present compound is expected to be effective in the treatment of Parkinson's tremor according to the conventional known protocol.

In FIG. 20, N=8. And,* means p<0.05 in statistical comparison with vehicle administration group (Dunnett's test).

Test 11. Effect for Inhibiting Neuronal Firing in Mouse Brain Slice

It is suggested that the motor symptom in neurological diseases such as Parkinson's disease and essential tremor is related to the dysregulation of motor circuit due to hyperexcitability in subthalamic nucleus or cerebellum. The action of the present compound for regulating the voluntary firing frequency in subthalamic nucleus neuron and cerebellar Purkinje cell was measured by patch-clamp method in mouse brain slice. The brain tissue was extirpated from male C57BL/6J mice (>7 weeks old) (CHARLES RIVER LABORATORIES JAPAN, INC.), and a brain slice was prepared from the brain tissue in a solution for slice preparation (solvent composition for slice preparation: 92 mmol/L N-methyl-D-glucamine (NMDG), 25 mmol/L D-glucose, 20 mmol/L HEPES, 30 mmol/L $NaHCO_3$, 0.5 mmol/L $CaCl_2$), 10 mmol/L $MgSO_4.7H_2O$, 2.5 mmol/L KCl, 1.25 mmol/L $NaH_2PO_4.2H_2O$, 2 mmol/L thiourea, 5 mmol/L ascorbic acid, 3 mmol/L pyruvic acid, 12 mmol/L N-acetyl-L-cysteine (NAC) (pH 7.4, under a stream of mixed gas of 5% $CO_2$.95% $O_2$)). The brain slice was incubated in record solution warmed at 37° C. for 30 minutes (composition of record solvent: 11.9 mmol/L NaCl, 0.2 mmol/L $CaCl_2$, 0.2 mmol/L $MgSO_4.7H_2O$, 0.25 mmol/L KCl, 0.125 mmol/L $NaH_2PO_4.2H_2O$ (under a stream of mixed gas of 5% $CO_2$.95% $O_2$)), and then the record solution was perfused at room temperature to carry out patch-clamp measurement. As record solution in glass electrode, 1 mmol/L $MgCl_2$, 20 mmol/L KCl, 1 mmol/L EGTA, 10 mmol/L HEPES, 4 mmol/L D-glucose, and 123 mmol/L potassium gluconate (pH 7.4) were used. The electrode was appressed on the cells of the test subject, it was confirmed that the seal resistance of gigaohm level was formed, the electric potential was fixed around resting membrane potential, and negative voltage was added to the electrode to make the plasma membrane perforated. As stimulus protocol, a current of +200 pA or +400 pA was added thereto for 400 milliseconds and the raised action potential was recorded. The above stimulus protocol was carried out every 10 times for each amount of current. The action potential was digitized with a digitizer (Digidata1400A) through an amplifier (MultiClamp 700B). The stimulus-controlled and digitized action potential was recorded with Clampex software (Version 10.2) (all instruments are from Molecular Device Corporation, Union City, Calif., USA). The recording of the action potential was carried out twice, before and after adding the compound of Example 13 (500 μmol/L). In the measurement after adding the compound of Example 13, the action potential was recorded after the record solution containing the compound of Example 13 was perfused for more than 10 minutes. In the analyses, the percentage of the spike firing frequency (Hz) for the current stimulation after adding the compound of Example 13, per the spike firing frequency (Hz) for the current stimulation before adding the compound of Example 13, was calculated, which was defined as a change rate of spike firing frequency in each cell.

Figure 21:
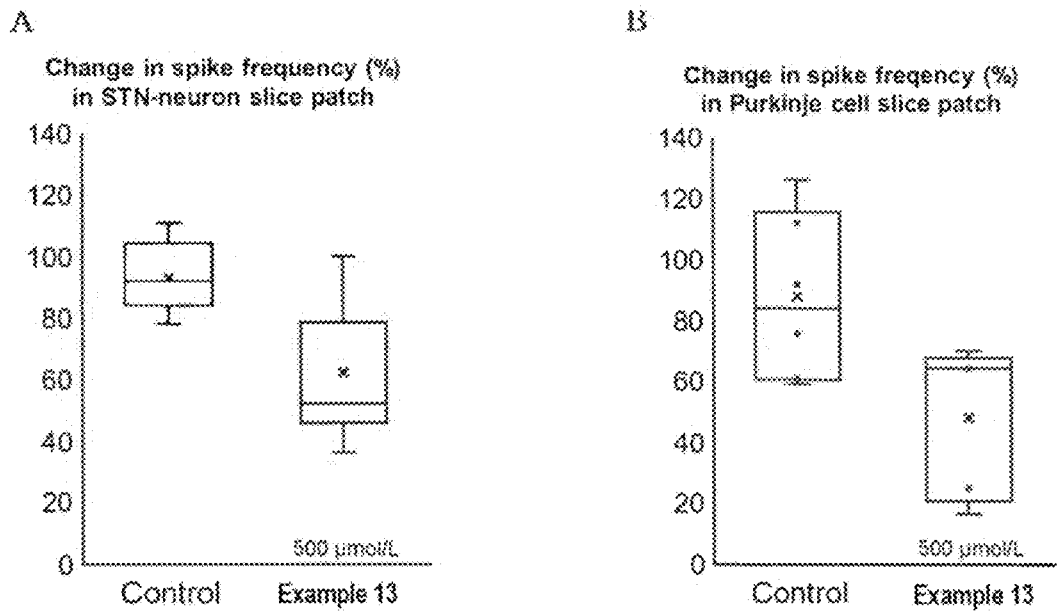
FIG. 21 shows the results of Test 11 about Example 13, which shows the effect for inhibiting neuronal firing in mouse brain slice. The axis of ordinate denotes the percentage based on the ratio of the spike firing frequencies in the neuron after/before adding the compound of the Example compound, which was measured by patch-clamp measurement. A and B show the results of the subthalamic nucleus neuron and the cerebellar Purkinje cell, respectively. The dose of the compound is denoted as a concentration thereof in the record solution (μmol/L), wherein the brain slice is perfused.

The result is shown in FIG. 21. The compound of Example 13 significantly inhibited the spike firing frequency in (A) subthalamic nucleus neuron and (B) cerebellar Purkinje cell. These results suggest that the present compound is effective in the treatment of motor symptom in neurological disease.

In FIG. 21, (A) N=10 or 11, (B) N=5 or 6. And, * means $p<0.05$ in statistical comparison with vehicle administration group (Welch's t-test).

Test 12. Anxiolytic-Like Action

In Parkinson's disease, psychiatric symptom (e.g. depression, anxiety) is known as one of its non-motor symptoms. The anxiolytic-like action of the present invention was evaluated with mouse elevated plus maze. The present test is broadly used as a method for evaluating the anxiolytic-like action of agents.

In the present test, male Crl: CD1 (ICR) mice (CHARLES RIVER LABORATORIES JAPAN, INC.) were used. One hour before the test was started, the solvent, the compound of Example 13 (3 mg/kg, 10 mg/kg, 30 mg/kg, or 100 mg/kg), or diazepam (3 mg/kg) which is a positive control was orally administered to the mouse. The mouse was put into a center platform in which the illuminance was adjusted to 80-100 Lux level. The head of the mouse was set toward the closed arm, and then the test was started. The mouse was allowed to explore freely for 5 minutes. When ⅓ of the mouse's body entered the arm, the behavior was counted as arm entry. And, the time spent in the open arm was also measured with a stopwatch. The ratio of the count of the open arm entry per the count of the all arm entry, and the ratio of the time spent in the open arm per the total exploration time (5 minutes) were calculated. In an elevated plus maze, a mouse does not voluntarily enter the open arm or explore there since a mouse feels anxious in the open arm which has no wall. Thus, the ratio of the count of the open arm entry per the count of the all arm entry, and the ratio of the time spent in the open arm per the total exploration time tend to be small values. When these ratios in the drug administration group are higher than those of the solvent administration group, it can be judged that the drug has anxiolytic-like action.

Figure 22:
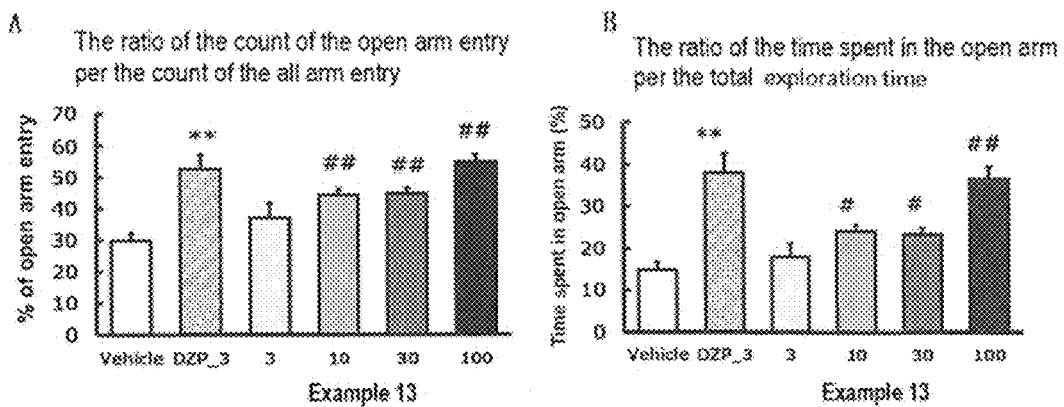
FIG. 22 shows the results of Test 12 about Example 13, which shows the anxiolytic-like action. The axis of ordinate in A denotes the ratio of the count of the open arm entry per the count of the all arm entry, and the axis of ordinate in B denotes the ratio of the time spent in the open arm per the total exploration time. The white columns (Vehicle) indicate the results of the vehicle administration group, the shaded columns (DZP_3) indicate the results of diazepam administration (3 mg/kg) group, which is used as a positive control substance of an anxiolytic drug, and the colored column indicates the results of Example 13 administration group, with the indication of its dose in the bottom of each column.

The result is shown in FIG. 22. Diazepam (DZP) made the count of the open arm entry and the time spent in the open arm increase significantly, which suggests that the present test was validated as an evaluation of anxiolytic-like action. The compound of Example 13 made the count of the open arm entry and the time spent in the open arm increase significantly when the dose of the compound was 10 mg/kg or more. The result suggests that the compound of Example 13 has an anxiolytic-like action.

In FIG. 22, Vehicle: N=13, DZP: N=11, Example 13: 3 mg/kg N=7, 10 mg/kg N=13, 30 mg/kg N=12, 100 mg/kg N=13. ** means $p<0.01$ in statistical comparison between vehicle administration group and diazepam administration group (Student's t-test). And, # and ##mean $p<0.05$ and $p<0.01$ in statistical comparison between vehicle administration group and Example 13 administration group (Dunnett's test), respectively.

Test 13. Effect for Sleeping Stage/Waking Stage

As non-motor symptoms in Parkinson's disease, sleep disorder such as insomnia (e.g. difficulty falling asleep, nocturnal awakening, etc.) is known. It is important to improve sleeping quality. The effect of the present compounds for sleep was evaluated by measuring rat sleep electroencephalogram.

In the present test, male Crlj: WI rats (CHARLES RIVER LABORATORIES JAPAN, INC.) were used. Under anesthesia, a radiofrequency transmitter (HD-S02, Data Science International, Inc.) was set in the peritoneal cavity of the rat, and two electrodes for measuring electroencephalogram were stereotaxically placed in the skull (frontoparietal electrode: 2 mm ahead of bregma and 2 mm left from midline, parietal electrode: 5 mm behind bregma and and 2 mm right from midline). An electrode for recording electromyogram was placed in the dorsal neck muscle. After more than one week as postoperative recuperation period, the rats were used in the sleep electroencephalogram measurement.

The compound of Example 13 (30 mg/kg or 100 mg/kg) was orally administered to the rat just before light phase, and the electroencephalogram and electromyogram of the rat were recorded at 500 Hz for 6 hours in a breeding cage in a soundproof box. The recorded signals were classified to 3 stages, wake/REM sleep/non-REM sleep every 10 seconds with a sleep analysis program Sleepsign (version 3, Kissei Comtec Co., Ltd.), and aggregated. Specifically, when the myoelectric response was beyond the threshold defined for each individual animal, it was classified as wake, and otherwise it was classified as sleep. In the sleep, when the power value at delta wave (0.5-4 Hz) of EEG-frequency component was beyond the threshold defined for each individual beforehand, it was classified as non-REM sleep. When the power value at theta wave (4-8 Hz) was beyond 40% of the total power value at 0.5-80 Hz, it was classified as REM sleep.

Figure 23:
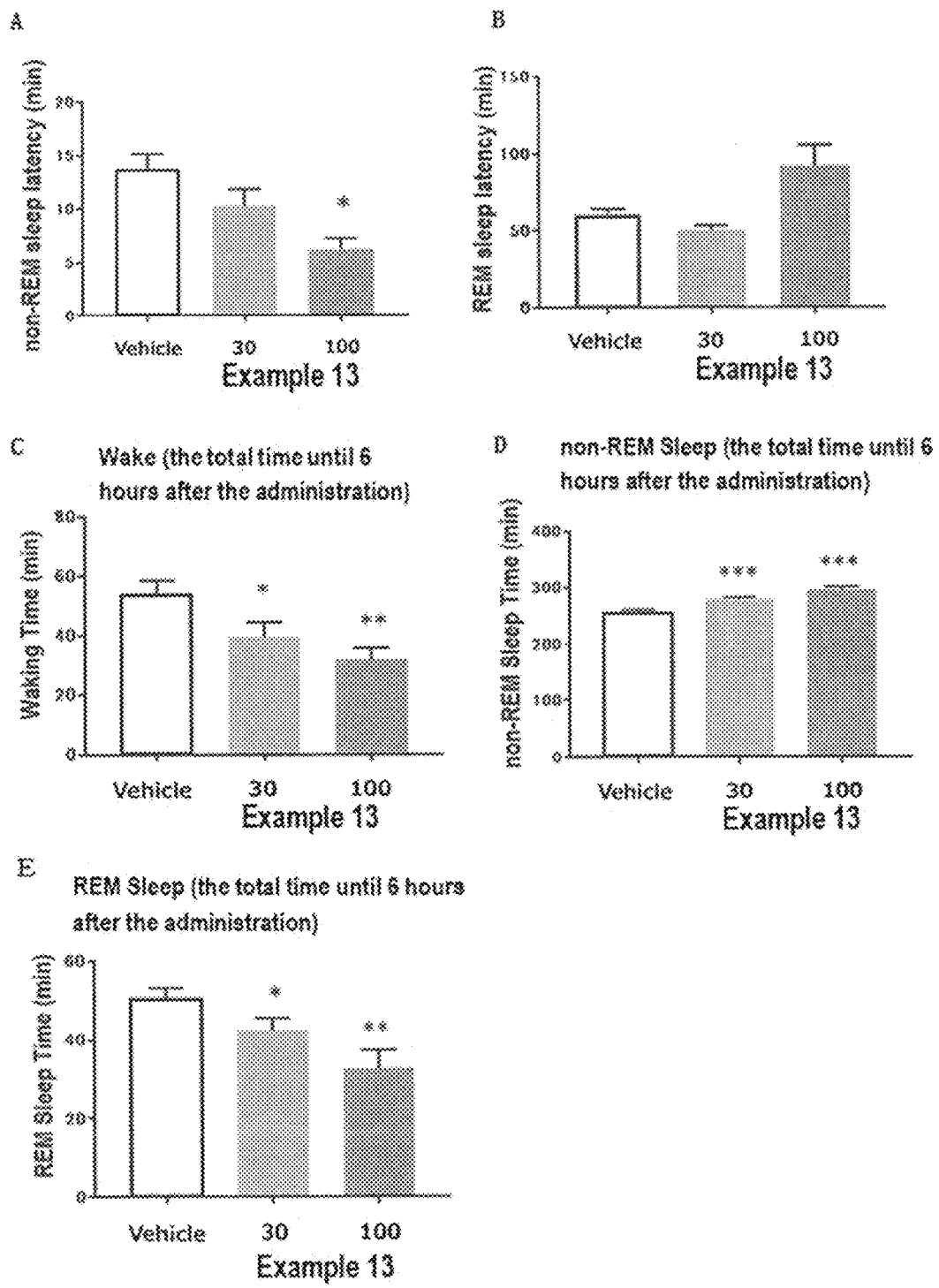
FIG. 23 shows the results of Test 13 about Example 13, which shows the effect to (A) non-REM sleep latency, (B) REM sleep latency, (C) wake duration, (D) non-REM sleep duration, and (E) REM sleep duration. The axis of ordinate denotes the total time in minutes until 6 hours after the administration. The white columns indicate the results of the vehicle administration group, and the gray columns indicate the results of Example 13 administration group, with the indication of its dose (mg/kg).

The result is shown in FIG. 23. The compound of Example 13 significantly shortened the non-REM sleep latency in a dose-dependent manner and increased the non-REM sleep time, and significantly shortened the waking time. On the other hand, the compound tended to elongate the REM sleep latency and significantly shortened the REM sleep time in a dose-dependent manner. These results suggest that the compound of Example 13 can improve sleep disorder such as difficulty falling asleep and nocturnal awakening.

In FIG. 23, N=8 in each group. *, , and * mean $p<0.05$, $p<0.01$, and $p<0.001$ in statistical comparison with vehicle administration group and Example 13 administration group (One-way ANOVA, followed by parametric Dunnett's test), respectively.

INDUSTRIAL APPLICABILITY

The present compound has T-type calcium channel inhibitory activity, thus the present compound is useful as a medicament for treating and/or preventing various nervous system diseases or psychiatric diseases. In addition, the present compound has potentiating effect of levodopa-induced hyperactivity which is different from the activity derived by MAOB inhibitory action. And, preferred compounds of the present invention have lower risk of nephrolithiasis because the action inhibiting carbonic anhydrase is attenuated. Thus, for highly safe treatment for Parkinson's disease, the present compound is useful as a drug for combination with a levodopa preparation. In addition, the present compound inhibited the onset of dyskinesia in a levodopa-induced dyskinesia model, thus the present compound is useful as a medicament for treating and/or preventing Parkinson's disease, which is highly safe compared to other existing drugs for combination with levodopa. In addition, the present compound exhibited efficacy for Parkinson's disease tremor model and essential tremor model, thus the present compound is useful as a medicament for treating and/or preventing Parkinson's disease tremor, essential tremor, as well as parkinsonism developed in nervous system diseases or psychiatric diseases. In addition, the present compound exhibited anxiolytic-like effect in elevated plus maze test, and shortening of non-REM sleep latency or shortening of wake hours in sleep electroencephalogram test, thus the present compound is useful as a medicament for treating and/or preventing non-motor symptoms of Parkinson's disease such as psychiatric symptom and sleep disorder. Furthermore, the present compound exhibited antiallodynic effect for oxaliplatin-induced pain model, thus the present compound is also useful as a medicament for treating and/or preventing neuropathic pain (in particular, pain and allodynia in chemotherapy-induced peripheral neuropathy).

The invention claimed is:

1. A compound of (1R)-1-(1,2-benzoxazol-3-yl)ethane-1-sulfonamide or a pharmaceutically acceptable salt thereof.

2. The compound of claim 1, which is a crystalline form characterized by a powder x-ray diffraction pattern having diffraction angle (2θ°) peaks of 5.7°±0.2 and 17.3°±0.2°.

3. The compound of claim 1, which is a crystalline form characterized by a powder x-ray diffraction pattern having diffraction angle (2θ°) peaks of 8.7°±0.2° and 17.6°±0.2°.

4. The compound of claim 1, which is a crystalline form characterized by a powder x-ray diffraction pattern having diffraction angle (2θ°) peaks of 11.1°±0.2° and 20.3°±0.2°.

5. A pharmaceutical composition, comprising:
the compound of claim 1 or a pharmaceutically acceptable salt thereof.

6. A pharmaceutical composition comprising:
the compound of claim 2.

7. A pharmaceutical composition comprising:
the compound of claim 3.

8. A pharmaceutical composition comprising:
the compound of claim 4.

9. A method for treating at least one of levodopa-induced dyskinesia in Parkinson's disease, essential tremor, chemotherapy-induced peripheral neuropathy, allodynia associated with neuropathic pain, Parkinson's disease, and at least one Parkinson's disease symptom of tremor, muscle stiffness/muscle rigidity, akinesia/bradykinesia, impairment of postural reflex, sleep disorder, and anxiety, comprising:
administering a therapeutically effective amount of the compound of claim 1 or a pharmaceutically acceptable salt thereof to a subject in need thereof.

10. The method of claim 9, wherein (1R)-1-(1,2-benzoxazol-3-yl)ethane-1-sulfonamide is a crystalline form characterized by a powder x-ray diffraction pattern having diffraction angle (2θ°) peaks of 5.7°±0.2 and 17.3°±0.2°.

11. The method of claim 9, wherein (1R)-1-(1,2-benzoxazol-3-yl)ethane-1-sulfonamide is a crystalline form characterized by a powder x-ray diffraction pattern having diffraction angle (2θ°) peaks of 8.7°±0.2° and 17.6°±0.2°.

12. The method of claim 9, wherein (1R)-1-(1,2-benzoxazol-3-yl)ethane-1-sulfonamide is a crystalline form characterized by a powder x-ray diffraction pattern having diffraction angle (2θ°) peaks of 11.1°±0.2° and 20.3°±0.2°.

13. The method of claim 9, wherein the disease which is treated is at least one of essential tremor, chemotherapy-induced peripheral neuropathy, Parkinson's disease, and at least one Parkinson's disease symptom of tremor, muscle stiffness/muscle rigidity, akinesia/bradykinesia, and impairment of postural reflex.

14. The method of claim 13, wherein the (1R)-1-(1,2-benzoxazol-3-yl)ethane-1-sulfonamide is a crystalline form characterized by a powder x-ray diffraction pattern having diffraction angle (2θ°) peaks of 5.7°±0.2 and 17.3°±0.2°.

15. The method of claim 13, wherein the (1R)-1-(1,2-benzoxazol-3-yl)ethane-1-sulfonamide is a crystalline form characterized by a powder x-ray diffraction pattern having diffraction angle (2θ°) peaks of 8.7°±0.2° and 17.6°±0.2°.

16. The method of claim 13, wherein the (1R)-1-(1,2-benzoxazol-3-yl)ethane-1-sulfonamide is a crystalline form characterized by a powder x-ray diffraction pattern having diffraction angle (2θ°) peaks of 11.1°±0.2° and 20.3°±0.2°.

17. The method of claim 9, wherein the disease which is treated is at least one of Parkinson's disease and at least one Parkinson's disease symptom of tremor, muscle stiffness/muscle rigidity, akinesia/bradykinesia, and impairment of postural reflex.

18. The method of claim 17, wherein the (1R)-1-(1,2-benzoxazol-3-yl)ethane-1-sulfonamide is a crystalline form characterized by a powder x-ray diffraction pattern having diffraction angle (2θ°) peaks of 5.7°±0.2 and 17.3°±0.2°.

19. The method of claim 17, wherein the (1R)-1-(1,2-benzoxazol-3-yl)ethane-1-sulfonamide is a crystalline form characterized by a powder x-ray diffraction pattern having diffraction angle (2θ°) peaks of 8.7°±0.2° and 17.6°±0.2°.

20. The method of claim 17, wherein the (1R)-1-(1,2-benzoxazol-3-yl)ethane-1-sulfonamide is a crystalline form characterized by a powder x-ray diffraction pattern having diffraction angle (2θ°) peaks of 11.1°±0.2° and 20.3°±0.2°.

21. The method of claim 9, wherein tremor as the Parkinson's disease symptom is treated.

22. The method of claim 21, wherein the (1R)-1-(1,2-benzoxazol-3-yl)ethane-1-sulfonamide is a crystalline form characterized by a powder x-ray diffraction pattern having diffraction angle (2θ°) peaks of 5.7°±0.2 and 17.3°±0.2°.

23. The method of claim 21, wherein the (1R)-1-(1,2-benzoxazol-3-yl)ethane-1-sulfonamide is a crystalline form characterized by a powder x-ray diffraction pattern having diffraction angle (2θ°) peaks of 8.7°±0.2° and 17.6°±0.2°.

24. The method of claim 21, wherein the (1R)-1-(1,2-benzoxazol-3-yl)ethane-1-sulfonamide is a crystalline form characterized by a powder x-ray diffraction pattern having diffraction angle (2θ°) peaks of 11.1°±0.2° and 20.3°±0.2°.

25. The method of claim 9, wherein the disease which is treated is essential tremor.

26. The method of claim 25, wherein the (1R)-1-(1,2-benzoxazol-3-yl)ethane-1-sulfonamide is a crystalline form characterized by a powder x-ray diffraction pattern having diffraction angle (2θ°) peaks of 5.7°±0.2 and 17.3°±0.2°.

27. The method of claim 25, wherein the (1R)-1-(1,2-benzoxazol-3-yl)ethane-1-sulfonamide is a crystalline form characterized by a powder x-ray diffraction pattern having diffraction angle (2θ°) peaks of 8.7°±0.2° and 17.6°±0.2°.

28. The method of claim 25, wherein the (1R)-1-(1,2-benzoxazol-3-yl)ethane-1-sulfonamide is a crystalline form characterized by a powder x-ray diffraction pattern having diffraction angle (2θ°) peaks of 11.1°±0.2° and 20.3°±0.2°.

* * * * *